(12) United States Patent
Zemolka et al.

(10) Patent No.: US 8,399,503 B2
(45) Date of Patent: Mar. 19, 2013

(54) SPIROCYCLIC AZAINDOLE DERIVATIVES

(75) Inventors: Saskia Zemolka, Aachen (DE); Stefan Schunk, Aachen (DE); Ellen Bergrath, Würselen (DE); Babette-Yvonne Kögel, Langerwehe-Hamich (DE); Werner Englberger, Stolberg (DE); Klaus Linz, Wachtberg (DE); Hans Schick, Berlin (DE)

(73) Assignee: Gruenenthal GmbH, Aachen (DE)

( * ) Notice: Subject to any disclaimer, the term of this patent is extended or adjusted under 35 U.S.C. 154(b) by 844 days.

(21) Appl. No.: 12/354,001

(22) Filed: Jan. 15, 2009

(65) Prior Publication Data
US 2009/0156593 A1 Jun. 18, 2009

Related U.S. Application Data

(63) Continuation of application No. PCT/EP2007/006326, filed on Jul. 17, 2007.

(30) Foreign Application Priority Data

Jul. 18, 2006 (DE) .......................... 10 2006 033 114

(51) Int. Cl.
*A61K 31/407* (2006.01)
*C07D 209/96* (2006.01)
*C07D 209/58* (2006.01)

(52) U.S. Cl. ........ 514/411; 548/407; 514/410; 514/279; 546/17; 546/18

(58) Field of Classification Search .................. 546/17, 546/18; 514/270

See application file for complete search history.

(56) References Cited

U.S. PATENT DOCUMENTS

| | | | |
|---|---|---|---|
| 4,065,573 A | 12/1977 | Lednicer | |
| 5,216,159 A | 6/1993 | Thurkauf et al. | |
| 7,872,133 B2 | 1/2011 | Ohmoto et al. | |
| 7,964,726 B2 | 6/2011 | Ohmoto et al. | |
| 2005/0187281 A1 | 8/2005 | Hinze et al. | |
| 2005/0187282 A1 | 8/2005 | Roffey et al. | |
| 2005/0192333 A1 | 9/2005 | Hinze et al. | |
| 2006/0004034 A1 | 1/2006 | Hinze et al. | |
| 2006/0154944 A1 | 7/2006 | Ohmoto et al. | |
| 2007/0213351 A1 | 9/2007 | Sundermann et al. | |
| 2008/0114012 A1 | 5/2008 | Ohmoto et al. | |
| 2008/0221141 A1 | 9/2008 | Friderichs et al. | |
| 2009/0111842 A1 | 4/2009 | Merla et al. | |
| 2009/0156593 A1 | 6/2009 | Zemolka et al. | |
| 2009/0163716 A1 | 6/2009 | Hinze et al. | |
| 2009/0247561 A1 | 10/2009 | Zemolka et al. | |
| 2010/0048553 A1 | 2/2010 | Schunk et al. | |
| 2010/0048554 A1 | 2/2010 | Schunk et al. | |
| 2010/0240897 A1 | 9/2010 | Hinze et al. | |
| 2011/0053970 A1 | 3/2011 | Friderichs et al. | |
| 2011/0207700 A1 | 8/2011 | Ohmoto et al. | |

FOREIGN PATENT DOCUMENTS

| | | |
|---|---|---|
| DE | 60112 064 T2 | 6/2006 |
| EP | 1 142 587 | 10/2001 |
| JP | 06 502147 H | 3/1994 |
| WO | 92 06094 A1 | 4/1992 |
| WO | 00 38720 A1 | 7/2000 |
| WO | 02 090317 | 11/2002 |
| WO | 2004 043967 | 5/2004 |
| WO | 2004 113300 A1 | 12/2004 |
| WO | 2005 063769 | 7/2005 |
| WO | 2005 066183 | 7/2005 |
| WO | 2006/041830 A2 | 4/2006 |
| WO | 2006 068164 A1 | 6/2006 |
| WO | 2006 108565 | 10/2006 |
| WO | 2008 009416 A1 | 1/2008 |

OTHER PUBLICATIONS

Dorwald F. A. Side Reactions in Organic Synthesis, 2005, Wiley: VCH, Weinheim p. IX of Preface.*
Molecular variations based on isosteric replacements,,, Wermuth, 1996.*
Toshiya Manabe et al., "Facilitation of long-term potentiation and memory in mice lacking nociceptin receptors", Nature, vol. 394, pp. 577-581, Aug. 6, 1998.
Miyuki Nishi et al., "Unrestrained nociceptive response and disregulation of hearing ability in mice lacking the nociceptin/orphaninFQ receptor", The EMBO Journal, vol. 16, No. 8, pp. 1858-1864, 1997.
Claudia Pütz, "Further Opioid Receptors", Chemistry and Pharmacology, pp. 455-476, 2002.
Girolamo Calo et al., "Pharmacology of nociceptin and its receptor: a novel therapeutic target", British Journal of Pharmacology, vol. 129, pp. 1261-1283, (2000).
Elmar Friderichs, "Opioids", Chemistry and Pharmacology, pp. 127-150, 2002.
Reinscheid, et al, "Orphanin FQ: A Neuropepetide that Activates an Opioidlike G Protein-Coupled Receptor", Science, vol. 270, Nov. 3, 1995, pp. 792-794.
Meunier, et al, "Isolation and structure of the endogenous agonist of opioid receptor-like ORL1 receptor", Nature, vol. 377, Oct. 12, 1995, pp. 532-535.
Mogil, et al, "Orphanin FQ is a Functional Anti-Opioid Peptide"; Neuroscience, vol. 75, No. 2, 1996, pp. 333-337.
Jenck, et al, "Orphanin FQ acts as an anxiolytic to attenuate behavioral responses to stress"; Proc. Natl. Acad. Sci. USA, vol. 94, Dec. 1997, pp. 14854-14858.
King et al, "Spinal analgesic activity of orphanin FQ/nociceptin and its fragments", Neuroscience Letters 223 (1997), pp. 113-116.
Abdulla et al, "Axotomy Reduces the Effect of Analgesic Opioids Yet Increases the Effect of Nociceptin on Dorsal Root Ganglion Neurons"; The Journal of Neuroscience, Dec. 1, 1998, 18 (23), pp. 9685-9694.
Bignan, et al.: "3-(4-Piperidinyl)indoles and 3-(4-piperidinyl)pyrrolo-[2,3-b]pyridines as ligands for the ORL-1 receptor"; Bioorganic & Medicinal Chemistry Letters 16 (2006) 3524-3528.
B. C. Bishop, I. F. Cottrell, D. Hands; "Synthesis of 3-hydroxyalkylbenzo[b]furans via the palladium-catalysed hetroannulation of silyl-protected alkynols with 2-iodophenol"; Synthesis, 1997, 1315.
C. Cheng, D. R. Lieberman, R. D. Larsen, R. A. Reamer, T. R. Verhoeven, P. J. Reider; "Synthesis of the 5-HT1D receptor agonist MK-0462 via a Pd-catalyzed coupling reaction"; Tet. Lett., vol. 35, No. 38, 1994, 6981-6984.
L. Estel, F. Marsais, G. Quéguiner, "Metalation/SRB1 coupling in heterocyclic synthesis. A convenient methodology for ring functionalization"; J. Org. Chem. 1988, 53, 2740-2744.

(Continued)

*Primary Examiner* — Rita Desai
(74) *Attorney, Agent, or Firm* — Norris McLaughlin & Marcus, P.A.

(57) ABSTRACT

The invention relates to substituted azaindole derivatives, to methods for the production thereof, to medicaments containing said compounds and to the use of substituted azaindole derivatives for producing medicaments.

11 Claims, No Drawings

OTHER PUBLICATIONS

Lednicer et al.,"4-Amino-4-arcylcyclohexanones and their derivatives, a novel class of analgesics"; J.Med.Chem., 23, 1980, 424-430.

J. Malm, B. Rehn, A.-B. Hörnfeldt, S. Gronowitz, "Synthesis and NMR spectra of the six isomeric thieno[c]-fused 1,7- and 1,8-naphthyridines"; J. Het. Chem. 1994, 31, 11-15.

J. A. Turner, "Regiospecific electrophilic substitution of aminopyriodines: Ortho lithiatiion of 2-, 3-, and 4-(pivaloylamino)pyridines"; J. Org. Chem. 1983, 48, 3401-3408.

F. Ujjainwalla, D. Warner; "Synthesis of 5-, 6- and 7-azaindoles via palladium-catalyzed heteroannulation of internal alkynes"; Tet. Lett., 39, 1998, 5355-5358.

Prezewlocki, R. et al; "Opioids in chronic pain"; Euro. J. Pharmacol. Oct. 19, 2001; 429 (1-3) : 79-91 Abstract.

D'Amour and Smith; "A method for determining loss of pain sensation"; J. Pharm. Exp. Ther. 72, 74-79 (1941).

\* cited by examiner

SPIROCYCLIC AZAINDOLE DERIVATIVES

This application is a Continuation of PCT/EP2007/006326, filed Jul. 17, 2007, which claims foreign priority benefit under 35 U.S.C. §119 of the German Patent Application No. 10 2006 033 114.1 filed Jul. 18, 2006.

The present invention relates to substituted spirocyclic azaindole derivatives, processes for their preparation, medicaments containing these compounds and the use of substituted spirocyclic azaindole derivatives for the production of medicaments.

The treatment of chronic and non-chronic pain states is extremely important in medicine. There is therefore a widespread need for highly effective pain treatments. The urgent need for a patient-friendly and targeted treatment of chronic and non-chronic pain states, which from the patient's point of view is hereinafter understood to mean the successful and satisfactory handling and treatment of pain, is well documented in the large number of scientific papers and articles that have appeared in recent years in the field of applied analgesics and in basic research on nociception.

Conventional μ-opioids such as morphine are highly effective in treating severe to extremely severe pain and are extremely important in the control and treatment of pain. It can however be advantageous if other opioid receptors apart from the μ-opioid receptor are also influenced, in particular the ORL1 receptor, since the pure μ-opioids also exhibit undesired side effects such as constipation and respiratory depression, and can also lead to dependence. Furthermore, the δ,κ and ORL1 receptors are involved in the occurrence of pain (Opioids: Introduction, pp. 127-150, Further Opioid Receptors, 455-476 in: Analgesics—From Chemistry and Pharmacology to Clinical Applications, Wiley VCH, 2002).

The ORL1 receptor is also involved in the regulation of further physiological and pathophysiological processes. These include inter alia learning and memory formation (Manabe et al., Nature, 394, 1997, pp. 577-581), hearing ability (Nishi et al., EMBO J., 16, 1997, pp. 1858-1864) as well as numerous other processes. In a review article by Calo et al. (Br. J. Pharmacol., 129, 2000, 1261-1283) a survey is given of the indications or biological processes in which the ORL1 receptor plays a role, or might with a high degree of probability play a role. The following inter alia are mentioned: analgesia, stimulation and regulation of food intake, influence on μ agonists such as morphine, treatment of withdrawal symptoms, reduction of the addictive potential of opioids, anxiolysis, modulation of motor activity, memory disturbances, epilepsy; modulation of neurotransmitter secretion, in particular of glutamate, serotonin and dopamine, and concomitant neurodegenerative diseases; influencing of the cardiovascular system, initiation of an erection, diuresis, antinatriuresis, electrolyte balance, arterial blood pressure, hydropexic disorders, intestinal motility (diarrhoea), relaxing effects on the respiratory pathways and micturition reflex (urinary incontinence). The use of agonists and antagonists as anorectics and analgesics (also in combined administration with opioids) or nootropics is furthermore discussed.

Structurally related compounds that have a high affinity for the ORL1 receptor and for the μ-opioid receptor are known from the prior art (WO 04043967). In these compounds the aromatic heterocycle is however an indole ring, in which no carbon atom can be replaced by a nitrogen atom.

The object of the present invention was to provide further medicaments that act on the opioid receptor system and are therefore suitable for medicaments in particular for the treatment of the various illnesses connected with this system and for use in the medical indications associated therewith.

The present invention accordingly provides substituted spirocyclic azaindole derivatives of the general Formula I

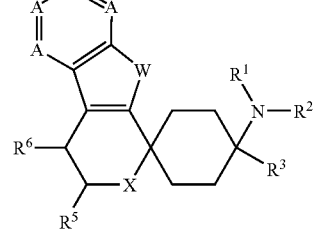

wherein
A denotes N or $CR^{7-10}$, wherein at least once and at most twice A denotes N
W denotes $NR^4$
X denotes $NR^{17}$, O or S
$R^1$ and $R^2$ independently of one another denote H; $C_{1-5}$-alkyl, in each case saturated or unsaturated, branched or unbranched, monosubstituted or polysubstituted or unsubstituted; $C_{3-8}$-cycloalkyl, in each case monosubstituted or polysubstituted or unsubstituted; or denote aryl, $C_{3-8}$-cycloalkyl or heteroaryl bonded via $C_{1-3}$-alkyl, in each case monosubstituted or polysubstituted or unsubstituted;
or the radicals $R^1$ and $R^2$ together denote $CH_2CH_2OCH_2CH_2$, $CH_2CH_2NR^{11}CH_2CH_2$ or $(CH_2)_{3-6}$,
  wherein $R^{11}$ denotes H; $C_{1-5}$-alkyl, in each case saturated or unsaturated, branched or unbranched, monosubstituted or polysubstituted or unsubstituted; $C_{3-8}$-cycloalkyl, in each case monosubstituted or polysubstituted or unsubstituted; aryl or heteroaryl, in each case monosubstituted or polysubstituted or unsubstituted; or aryl, $C_{3-8}$-cycloalkyl or heteroaryl bonded via $C_{1-3}$-alkyl, in each case monosubstituted or polysubstituted or unsubstituted; C(O)phenyl, C(O)heteroaryl, $C(O)C_{1-5}$-alkyl, in each case substituted or unsubstituted;
$R^3$ denotes $C_{1-8}$-alkyl, in each case saturated or unsaturated, branched or unbranched, monosubstituted or polysubstituted or unsubstituted; $C_{3-8}$-cycloalkyl, in each case monosubstituted or polysubstituted or unsubstituted; aryl or heteroaryl, in each case unsubstituted or monosubstituted or polysubstituted; aryl, heteroaryl or $C_{3-8}$-cycloalkyl bonded via a $C_{1-3}$-alkyl group, in each case unsubstituted or monosubstituted or polysubstituted;
$R^4$ denotes H; $C_{1-5}$-alkyl, saturated or unsaturated, branched or unbranched, unsubstituted or monosubstituted or polysubstituted; aryl or heteroaryl, in each case substituted or unsubstituted; aryl, heteroaryl or cycloalkyl bonded via a $C_{1-3}$-alkyl group, in each case monosubstituted or polysubstituted or unsubstituted; $COR^{12}$; $SO_2R^{12}$,
  wherein $R^{12}$ denotes H; $C_{1-5}$-alkyl, in each case saturated or unsaturated, branched or unbranched, monosubstituted or polysubstituted or unsubstituted; $C_{3-8}$-cycloalkyl, in each case saturated or unsaturated, monosubstituted or polysubstituted or unsubstituted; aryl or heteroaryl, in each case monosubstituted or polysubstituted or unsubstituted; or aryl, $C_{3-8}$-cycloalkyl or heteroaryl bonded via $C_{1-3}$-alkyl, in each case monosubstituted or polysubstituted or unsubstituted; $OR^{13}$; $NR^{14}R^{15}$;

$R^5$ denotes =O; H; $COOR^{13}$, $CONR^{13}$, $OR^{13}$; $C_{1-5}$-alkyl, saturated or unsaturated, branched or unbranched, unsubstituted or monosubstituted or polysubstituted; $C_{3-8}$-cycloalkyl, saturated or unsaturated, unsubstituted or monosubstituted or polysubstituted; aryl or heteroaryl, unsubstituted or monosubstituted or polysubstituted; or aryl, $C_{3-8}$-cycloalkyl or heteroaryl bonded via $C_{1-3}$-alkyl, unsubstituted or monosubstituted or polysubstituted;

$R^6$ denotes H; F, Cl, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$-alkyl, saturated or unsaturated, branched or unbranched, unsubstituted or monosubstituted or polysubstituted; $C_{3-8}$-cycloalkyl, saturated or unsaturated, unsubstituted or monosubstituted or polysubstituted; aryl or heteroaryl, unsubstituted or monosubstituted or polysubstituted; or aryl, $C_{3-8}$-cycloalkyl or heteroaryl bonded via $C_{1-3}$-alkyl, unsubstituted or monosubstituted or polysubstituted;

or $R^5$ and $R^6$ together denote $(CH_2)n$ where n=2, 3, 4, 5 or 6, wherein individual hydrogen atoms can also be replaced by F, Cl, Br, I, $NO_2$, $CF_3$, $OR^{13}$, CN or $C_{1-5}$-alkyl;

$R^7$, $R^8$, $R^9$ and $R^{10}$ independently of one another denote H, F, Cl, Br, I, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$-alkyl, $C_{3-8}$-cycloalkyl, unsubstituted or monosubstituted or polysubstituted; aryl or heteroaryl, unsubstituted or monosubstituted or polysubstituted; or aryl, $C_{3-8}$-cycloalkyl or heteroaryl bonded via $C_{1-3}$-alkyl, unsubstituted or monosubstituted or polysubstituted;

wherein $R^{13}$ denotes H; $C_{1-5}$-alkyl, in each case saturated or unsaturated, branched or unbranched, unsubstituted or monosubstituted or polysubstituted; $C_{3-8}$-cycloalkyl, in each case saturated or unsaturated, unsubstituted or monosubstituted or polysubstituted; aryl or heteroaryl, unsubstituted or monosubstituted or polysubstituted; or aryl, $C_{3-8}$-cycloalkyl or heteroaryl bonded via $C_{1-3}$-alkyl, unsubstituted or monosubstituted or polysubstituted;

$R^{14}$ and $R^{15}$ independently of one another denote H; $C_{1-5}$-alkyl, in each case saturated or unsaturated, branched or unbranched, unsubstituted or monosubstituted or polysubstituted; or $C_{3-8}$-cycloalkyl, in each case saturated or unsaturated, unsubstituted or monosubstituted or polysubstituted; aryl or heteroaryl, unsubstituted or monosubstituted or polysubstituted; or aryl, $C_{3-8}$-cycloalkyl or heteroaryl bonded via $C_{1-3}$-alkyl, unsubstituted or monosubstituted or polysubstituted;

or $R^{14}$ and $R^{15}$ together denote $CH_2CH_2OCH_2CH_2$, $CH_2CH_2NR^{16}CH_2CH_2$ or $(CH_2)_{3-6}$, wherein $R^{16}$ denotes H; $C_{1-5}$-alkyl, saturated or unsaturated, branched or unbranched, unsubstituted or monosubstituted or polysubstituted;

$R^{17}$ denotes H; $C_{1-8}$-alkyl, saturated or unsaturated, branched or unbranched; $COR^{12}$ or $SO_2R^{12}$ in the form of the racemate; in the form of the enantiomers, diastereomers, mixtures of the enantiomers or diastereomers, or of an individual enantiomer or diastereomer; in the form of the bases and/or salts of physiologically compatible acids.

The compounds according to the invention exhibit a good bonding to the μ-opioid receptor and the ORL-1 receptor.

The expressions "$C_{1-8}$-alkyl", "$C_{1-3}$-alkyl", and "$C_{1-5}$-alkyl" include in the context of the present invention acyclic saturated or unsaturated hydrocarbons, which can be branched or straight-chain as well as unsubstituted or monosubstituted or polysubstituted, with 1 to 8 C atoms or 1 to 3 C atoms or 1 to 5 C atoms, i.e. $C_{1-8}$-alkanyls, $C_{2-8}$-alkenyls and $C_{2-8}$-alkinyls or $C_{1-3}$-alkanyls, $C_{2-3}$-alkenyls and $C_{2-3}$-alkinyls or $C_{1-5}$-alkanyls, $C_{2-5}$-alkenyls and $C_{2-5}$-alkinyls. In this connection alkenyls contain at least one C—C double bond and alkinyls contain at least one C—C triple bond. Preferably alkyl is selected from the group comprising methyl, ethyl, n-propyl, 2-propyl, n-butyl, iso-butyl, sec.-butyl, tert.-butyl, n-pentyl, iso-pentyl, neo-pentyl, n-hexyl, 2-hexyl, n-heptyl, n-octyl, 1,1,3,3-tetramethylbutyl; ethylenyl (vinyl), ethinyl, propenyl (—$CH_2CH=CH_2$, —CH=CH—$CH_3$, —C(=$CH_2$)—$CH_3$), propinyl (—CH—C≡CH, —C≡C—$CH_3$), butenyl, butinyl, pentenyl, pentinyl, hexenyl, hexinyl, heptenyl, heptinyl, octenyl and octinyl. Particularly preferred are methyl, ethyl, n-propyl, n-butyl, sec-butyl, iso-butyl.

The expression "cycloalkyl" or "$C_{3-8}$-cycloalkyl" denotes for the purposes of the present invention cyclic hydrocarbons with 3, 4, 5, 6, 7 or 8 carbon atoms, wherein the hydrocarbons may be saturated or unsaturated (but not aromatic), unsubstituted or monosubstituted or polysubstituted. With regard to cycloalkyl the term also includes saturated or unsaturated (but not aromatic) cycloalkyls in which one or two carbon atoms are replaced by a heteroatom S, N or O. Advantageously $C_{3-8}$-cycloalkyl is selected from the group containing cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl. Cyclopropyl, cyclobutyl, cyclopentyl and cyclohexyl are particularly preferred.

The expression "aryl" denotes in the context of the present invention aromatic hydrocarbons, including inter alia phenyls and naphthyls. The aryl radicals can also be condensed with further saturated, (partially) unsaturated or aromatic ring systems, so that the aryl radical forms an aromatic ring system containing at most 20 C atoms. Each of these $C_{6-20}$-aryl radicals can be present unsubstituted or monosubstituted or polysubstituted, wherein the aryl substituents can be identical or different and can be in any arbitrary and possible position of the aryl. Advantageously aryl is selected from the group containing phenyl, 1-naphthyl, 2-naphthyl, which can in each case be unsubstituted or monosubstituted or polysubstituted. The phenyl radical is particularly preferred.

The expression "heteroaryl" denotes a 5-, 6- or 7-membered cyclic aromatic radical that contains at least 1 but possibly also 2, 3, 4 or 5 heteroatoms, wherein the heteroatoms are identical or different and the heterocycle can be unsubstituted or monosubstituted or polysubstituted; in the case of the substitution on the heterocycle the substituents can be identical or different and can be in any arbitrary and possible position of the heteroaryl. The heterocycle can also be part of a bicyclic or polycyclic system with a total of up to 20 ring members. Preferred heteroatoms are nitrogen, oxygen and sulphur. It is preferred if the heteroaryl radical is selected from the group containing pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phtalazinyl, pyrazolyl, imidazolyl, thiazolyl, oxazolyl, isoxazoyl, pyridyl, pyridazinyl, pyrimidinyl, pyrazinyl, pyranyl, indazolyl, purinyl, indolizinyl, chinolinyl, isochinolinyl, chinazolinyl, carbazolyl, phenazinyl, phenothiazinyl, triazolyl or oxadiazolyl, wherein the bonding to the compounds of the general structure I can take place via any arbitrary and possible ring member of the heteroaryl radical. Preferred are pyridyl, furyl, thienyl, indolyl, benzothienyl, pyrrolyl, triazolyl and isoxazolyl, particularly preferred being pyridyl, thienyl, benzothienyl and triazolyl.

The expression "aryl or heteroaryl bonded via $C_{1-3}$-alkyl" denotes for the purposes of the present invention that $C_{1-3}$-alkyl and aryl or heteroaryl have the meanings defined above and the aryl or heteroaryl radical is bonded via a $C_{1-3}$-alkyl group to the compound of the general structure 1. Particularly preferred in the context of the present invention are benzyl and phenethyl.

In connection with "alkyl" or "cyloalkyl" the term "substituted" is understood in the context of the present invention to mean the substitution of a hydrogen atom by F, Cl, Br, I, —CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, S-benzyl, $OCF_3$, O—$C_{1-6}$-alkyl, OH, O—$C_{1-6}$-alkyl-OH, =O, $C_{1-6}$-alkyl, benzyl, O-benzyl, O-phenyl, C(=O)$C_{1-6}$-alkyl, $CO_2H$, $CO_2$—$C_{1-6}$-alkyl, wherein polysubstituted radicals are understood to denote those radicals which are polysubstituted, for example disubstituted or trisubstituted, either on different atoms or on the same atom, for example trisubstituted on the same C atom as in the case of $CF_3$ or —$CH_2CF_3$, or at different sites as in the case of —CH(OH)—CH=CH—$CHCl_2$. The polysubstitution can take place with the same or with different substituents. For the purposes of the present invention "monosubstituted or polysubstituted" in connection with alkyl preferably denotes substitution with $COOCH_3$, $OCH_3$, OH, $COOC_2H_5$, F or Cl.

With regard to "aryl" and "heteroaryl" the expression "monosubstituted or polysubstituted" denotes in the context of the present invention the monosubstitution or polysubstitution, for example disubstitution, trisubstitution or tetrasubstitution, of one or more hydrogen atoms of the ring system by F, Cl, Br, I, CN, $NH_2$, NH—$C_{1-6}$-alkyl, NH—$C_{1-6}$-alkyl-OH, N($C_{1-6}$alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$alkyl-OH, C(=O)$C_{1-6}$-alkyl,

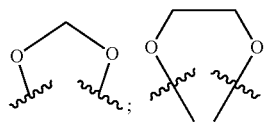

$CO_2$—$C_{1-6}$-alkyl, $CF_3$, $OCF_3$, $C_{1-6}$-alkyl, on one or possibly different atoms (wherein a substituent itself can possibly be substituted). The polysubstitution is in this connection carried out with the same or with different substituents. For "aryl" and "heteroaryl" preferred substituents are in this case —F, —Cl, —$CF_3$, —O—$CH_3$, OH, methyl, ethyl, n-propyl, nitro, tert.-butyl,

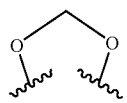

and —CN. Particularly preferred are —F and —Cl.

The expression "salt formed with a physiologically compatible acid" is understood in the context of the present invention to mean salts of the respective active substance with inorganic or organic acids that are physiologically compatible, especially when used in humans and/or mammals. The hydrochloride, the citrate, the hemicitrate and the methanesulfonate is preferred. The methanesulfonate is particularly preferred. Examples of physiologically compatible acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, malic acid, maleic acid, citric acid, glutamic acid, 1,1-dioxo-1,2-dihydro1$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric and/or aspartic acid. Citric acid, methanesulfonic acid and hydrochloric acid are preferred. Methanesulfonic acid is particularly preferred.

The term $(CH_2)_{3-6}$ and $(CH_2)_{4-5}$ is understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$—, and —$CH_2$—$CH_2$—$CH_2$—$CH_2$— and —$CH_2$—$CH_2$—$CH_2$—$CH_2$—$CH_2$—.

Preferred are compounds of the general Formula I,
in which the radicals A, W, X and $R^{1-17}$ have the meanings given above
wherein
the aforementioned $C_{1-8}$-alkyls, $C_{1-5}$-alkyls, $C_{1-3}$-alkyls and $C_{1-3}$-alkylenes and $C_{3-8}$-cycloalkyl radicals can in each case be monosubstituted or polysubstituted with F, Cl, Br, I, CN, $NH_2$, NH—$C_{1-6}$-alkyl, NH—$C_{1-6}$-alkyl-OH, N($C_{1-6}$alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, $CO_2H$, $CO_2$—$C_{1-6}$-alkyl, $CF_3$, $OCF_3$, $C_{1-6}$-alkyl,
the aforementioned aryl or heteroaryl radicals can in each case be monosubstituted or polysubstituted with F, Cl, Br, I, CN, $NH_2$, NH—$C_{1-6}$-alkyl, NH—$C_{1-6}$-alkyl-OH, N($C_{1-6}$alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, $CO_2H$, $CO_2$—$C_{1-6}$-alkyl, $CF_3$, $OCF_3$, $C_{1-6}$-alkyl,

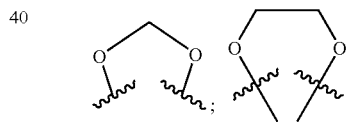

or phenoxy,
in the form of the racemate; in the form of the enantiomers, diastereomers, mixtures of the enantiomers or diastereomers, or in the form of an individual enantiomer or diastereomer; in the form of the bases and/or salts of physiologically compatible acids.

The radicals, groups and substituents described hereinafter as preferred can in the compounds according to the invention be combined in the broadest meaning of the remaining radicals, but also with preferred meanings of other radicals, groups and substituents.

In a preferred embodiment of the spirocyclic azaindole derivatives according to the invention the following applies:
$R^1$ and $R^2$ independently of one another denote H; $C_{1-5}$-alkyl, saturated or unsaturated, branched or unbranched, monosubstituted or polysubstituted or unsubstituted;
or the radicals $R^1$ and $R^2$ together form a ring and denote $CH_2CH_2OCH_2CH_2$, $CH_2CH_2NR^{11}CH_2CH_2$ or $(CH_2)_{3-6}$,
wherein $R^{11}$ denotes H; $C_{1-5}$-alkyl, saturated or unsaturated, branched or unbranched, monosubstituted or polysubstituted or unsubstituted.

Particularly preferred are spirocyclic azaindole derivatives wherein $R^1$ and $R^2$ independently of one another denote $CH_3$ or H, wherein $R^1$ and $R^2$ do not simultaneously denote H or $R^1$ and $R^2$ denote $(CH_2)_3$.

Most particularly preferred are spirocyclic azaindole derivatives wherein $R^1$ and $R^2$ denote $CH_3$.

Also preferred are spirocyclic azaindole derivatives wherein $R^3$ denotes ethyl, propyl, butyl, pentyl, hexyl, heptyl, cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or monosubstituted or polysubstituted; $C_5$- or $C_6$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl, triazolyl or pyrazinyl bonded via a saturated, unbranched $C_{1-3}$-alkyl group, in each case unsubstituted or monosubstituted or polysubstituted;

in particular $R^3$ denotes propyl, butyl, pentyl, hexyl, phenyl, furyl, thiophenyl, naphthyl, benzyl, benzofuranyl, indolyl, indanyl, benzodioxanyl, benzodioxolanyl, pyridyl, pyrimidyl, pyrazinyl, triazolyl or benzothiophenyl, in each case unsubstituted or monosubstituted or polysubstituted; phenyl, furyl or thiophenyl bonded via a saturated, unbranched $C_{1-3}$-alkyl group, in each case unsubstituted or monosubstituted or polysubstituted.

Particularly preferred are spirocyclic azaindole derivatives wherein $R^3$ denotes propyl, butyl, pentyl, hexyl, phenyl, phenethyl, thiophenyl, pyridyl, triazolyl, benzothiophenyl or benzyl, in each case substituted or unsubstituted, and particularly preferably denotes propyl, 3-methoxypropyl, butyl, pentyl, hexyl, phenyl, 3-methylphenyl, 3-fluorophenyl, benzo[1,3]-dioxolyl, thienyl, benzothiophenyl, 4-chlorobenzyl, benzyl, 3-chlorobenzyl, 4-methylbenzyl, 2-chlorobenzyl, 4-fluorobenzyl, 3-methylbenzyl, 2-methylbenzyl, 3-fluorobenzyl, 2-fluorobenzyl, 1-methyl-1,2,4-triazolyl or phenethyl.

Most particularly preferred are spirocyclic azaindole derivatives wherein $R^3$ denotes butyl, ethyl, 3-methoxypropyl, benzothiophenyl, phenyl, 3-methylphenyl, 3-fluorophenyl, benzo[1,3]-dioxolyl, benzyl, 1-methyl-1,2,4-triazolyl, thienyl or phenethyl.

$R^4$ preferably denotes H.

Also preferred are spirocyclic azaindole derivatives wherein $R^5$ denotes H, $C_{1-5}$-alkyl, branched or unbranched, unsubstituted or monosubstituted or polysubstituted, or denotes $COOR^{13}$.

Particularly preferred are spirocyclic azaindole derivatives wherein $R^5$ denotes $CH_3$, $CH_2OH$, COOH or $COOCH_3$.

Most particularly preferred are spirocyclic azaindole derivatives wherein $R^5$ denotes H.

Preferred are also spirocyclic azaindole derivatives wherein $R^6$ denotes H, $C_{1-5}$-alkyl, aryl, or aryl coupled via a $C_{1-3}$-alkyl group.

Particularly preferred are spirocyclic azaindole derivatives wherein $R^6$ denotes H, $CH_3$, phenyl or benzyl.

Most particularly preferred are spirocyclic azaindole derivatives wherein $R^6$ denotes H.

Furthermore, also preferred are spirocyclic azaindole derivatives wherein $R^7$, $R^8$, $R^9$ and $R^{10}$ independently of one another denote H; methyl, ethyl, propyl, butyl; pyridyl, O-benzyl, F, Cl, Br, I, $CF_3$, OH, $OCH_3$, $NH_2$, COOH, $COOCH_3$, $NHCH_3$ or $N(CH_3)_2$ or $NO_2$.

Particularly preferred are spirocyclic azaindole derivatives wherein $R^7$, $R^8$, $R^9$ and $R^{10}$ independently of one another denote H, F, OH, $CH_3$, Cl, $OCH_3$, Br or $NO_2$.

Most particularly preferred are spirocyclic azaindole derivatives wherein $R^7$, $R^8$, $R^9$ and $R^{10}$ denote H.

Also preferred are spirocyclic azaindole derivatives of the general Formula I, wherein A denotes N once and the remaining radicals A assume the meaning $CR^{7-9}$ or $CR^{8-10}$ or $CR^7$ and $CR^{9-10}$ or $CR^{7-8}$ and $CR^{10}$.

Particularly preferred are compounds of the general Formula Ia and Ib:

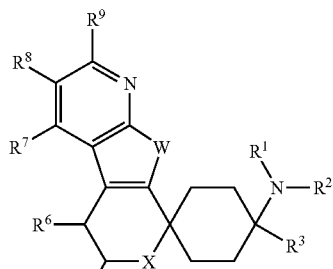

Ia

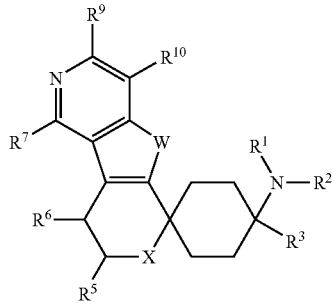

Ib wherein X, W and the radicals $R^1$-$R^{10}$ can adopt the meanings specified in the broadest definition as well as the meanings described as particularly preferred definitions.

Most particularly preferred are spirocyclic azaindole derivatives from the following group (1) 4-(dimethylamino)-4-phenyl-spiro[cyclohexane-1,8'-(5,6,8,9-tetrahydropyrano[3,4-b]-7-azaindole)]

(2) 4-(dimethylamino)-4-phenyl-spiro[cyclohexane-1,8'-(5,6,8,9-tetrahydropyrano[3,4-b]-7-azaindole)]; methansulfonate (3) 4-(dimethylamino)-4-phenyl-spiro[cyclohexane-1,6'-(5,6,8,9-tetrahydropyrano[3,4-b]-5-azaindole)]

(4) 4-(dimethylamino)-4-thiophen-2-yl-spiro[cyclohexane-1,8'-(5,6,8,9-tetrahydropyrano[3,4-b]-7-azaindole)]; methanesulfonate (5) 4-(dimethylamino)-4-thiophen-2-yl-spiro[cyclohexane-1,6'-(5,6,8,9-tetrahydropyrano[3,4-b]-5-azaindole)]

(6) 4-(dimethylamino)-4-phenyl-spiro[cyclohexane-1,8'-(5,6,8,9-tetrahydropyrano[3,4-b]-7-azaindole)]; citrate (4:3)

(7) 4-(methylamino)-4-phenyl-spiro[cyclohexane-1,8'-(5,6,8,9-tetrahydropyrano[3,4-b]-7-azaindole)]; citrate (1:1)

(8) 4-(methylamino)-4-thiophen-2-yl-spiro[cyclohexane-1,8'-(5,6,8,9-tetrahydropyrano[3,4-b]-7-azaindole)]; citrate (4:3)

(9) 4-(dimethylamino)-4-benzo[1,3-dioxol]-spiro[cyclohexane-1,8'-(5,6,8,9-tetrahydropyrano[3,4-b]-7-azaindole)]; citrate (1:1)

(10) 4-(dimethylamino)-4-(benzothiophen-2-yl)-spiro[cyclohexane-1,8'-(5,6,8,9-tetrahydropyrano[3,4-b]-7-azaindole)]; citrate (1:1)
(12) 4-(dimethylamino)-4-(3-fluorophenyl)-spiro[cyclohexane-1,8'-(5,6,8,9-tetrahydropyrano[3,4-b]-7-azaindole)]; citrate (4:3)
(13) 4-(dimethylamino)-4-(3-methylphenyl)-spiro[cyclohexane-1,8'-(5,6,8,9-tetrahydropyrano[3,4-b]-7-azaindole)]; citrate (1:1)
(14) 4-(dimethylamino)-4-(but-1-yl)-spiro[cyclohexane-1,8'-(5,6,8,9-tetrahydropyrano[3,4-b]-7-azaindole)], citrate (1:1)
(15) 4-(dimethylamino)-4-phenylethyl-spiro[cyclohexane-1,8'-(3-trifluoromethyl-5,6,8,9-tetrahydropyrano[3,4-b]-7-azaindole)]; citrate (1:1)
(17) 4-(dimethylamino)-4-ethyl-spiro[cyclohexane-1,8'-(5,6,8,9-tetrahydropyrano[3,4-b]-7-azaindole)]; citrate (2:3)
(18) 4-(dimethylamino)-4-phenylethyl-spiro[cyclohexane-1,8'-(5,6,8,9-tetrahydropyrano[3,4-b]-7-azaindole)]; citrate (2:3)
(19) 4-benzyl-4-morpholino-spiro[cyclohexane-1,8'-(5,6,8,9-tetrahydropyrano[3,4-b]-7-azaindole)]; citrate (1:1)
(20) 4-(dimethylamino)-4-(3-methoxypropyl)-spiro[cyclohexane-1,8'-(5,6,8,9-tetrahydropyrano[3,4-b]-7-azaindole)]; citrate (1:1)
(21) 4-(dimethylamino)-4-phenyl-spiro[cyclohexane-1,8'-(5,6,8,9-tetrahydropyrano[3,4-b]-7-azaindole)]; citrate (1:1)
(22) 4-(dimethylamino)-4-thiophen-2-yl-spiro[cyclohexane-1,8'-(5,6,8,9-tetrahydropyrano[3,4-b]-7-azaindole)]; citrate (1:1)
(23) 4-(dimethylamino)-4-phenyl-spiro[cyclohexane-1,6'-(5,6,8,9-tetrahydropyrano[3,4-b]-5-azaindole)], citrate (1:1)
(24) 4-(dimethylamino)-4-phenyl-spiro[cyclohexane-1,6'-(5,6,8,9-tetrahydropyrano[3,4-b]-5-azaindole)], citrate (1:1)
(25) 4-butyl-4-(dimethylamino)-spiro[cyclohexane-1,8'-(5,6,8,9-tetrahydropyrano[3,4-b]-7-azaindole)]; citrate (1:1)
(26) 4-butyl-4-(dimethylamino)-spiro[cyclohexane-1,8'-(5,6,8,9-tetrahydropyrano[3,4-b]-7-azaindole)]; citrate (1:1)
(27) 4-benzyl-4-morpholino-spiro[cyclohexane-1,8'-(3-trifluoromethyl-5,6,8,9-tetrahydropyrano[3,4-b]-7-azaindole)]; citrate (1:1)
(28) 4-(dimethylamino)-4-phenyl-spiro[cyclohexane-1,8'-(3-trifluoromethyl-5,6,8,9-tetrahydropyrano[3,4-b]-7-azaindole)]; citrate (1:1)
(29) 4-(azetidin-1-yl)-4-phenyl-spiro[cyclohexane-1,8'-(5,6,8,9-tetrahydropyrano[3,4-b]-7-azaindole)], Citrate (1:1)
(30) 4-butyl-4-(pyrrolidin-1-yl)-spiro[cyclohexane-1,8'-(5,6,8,9-tetrahydropyrano[3,4-b]-7-azaindole)]; citrate (2:1)
(31) 4-(dimethylamino)-4-phenyl-spiro[cyclohexane-1,8'-(5,6,8,9-tetrahydro-thiopyrano[3,4-b]-7-azaindole)]; citrate (1:1)
(32) 4-(dimethylamino)-4-phenyl-spiro[cyclohexane-1,6'-(5,6,8,9-tetrahydro-thiopyrano[3,4-b]-5-azaindole)], citrate (1:1)
(33) 4-(1-methyl-1H-1,2,4-triazol-5-yl)-4-(methylamino)-spiro[cyclohexane-1,8'-(5,6,8,9-tetrahydropyrano[3,4-b]-7-azaindole)], citrate (1:1)
(34) 4-(1-methyl-1H-1,2,4-triazol-5-yl)-4-(methylamino)-spiro[cyclohexane-1,8'-(5,6,8,9-tetrahydropyrano[3,4-b]-7-azaindole)], citrate (1:1)
in the form of the racemate; in the form of the enantiomers, diastereomers, mixtures of the enantiomers or diastereomers, or of an individual enantiomer or diastereomer; in the form of the bases and/or salts of physiologically compatible acids.

The substances according to the invention act for example on the µ-opioid receptor relevant in connection with various diseases and medical conditions, which means that they are suitable as a pharmaceutical active substance in a medicament. The present invention accordingly also provides medicaments containing at least one spirocyclic azaindole derivative according to the invention, as well as possibly suitable additives and/or auxiliary substances and/or optionally further active substances.

The medicaments according to the invention contain, apart from at least one spirocyclic azaindole derivative according to the invention, optionally also suitable additives and/or auxiliary substances, for example carrier materials, fillers, solvents, diluents, colorants and/or binders, and can be administered as liquid medicament forms in the form of injectable solutions, drops or syrups, as semi-solid medicament forms in the form of granules, tablets, pellets, patches, capsules, plasters/spray plasters or aerosols. The choice of the auxiliary substances, etc., as well as the amounts thereof to be used depend on whether the medicament is to be administered orally, parenterally, intravenously, intraperitoneally, intradermally, intramuscularly, intranasally, buccally, rectally or topically, for example to the skin, mucous membranes or to the eyes. For oral application preparations in the form of tablets, pills, capsules, granules, drops, syrups and juices are suitable, while for parenteral, topical and inhalative application solutions, suspensions, readily reconstitutable dry preparations as well as sprays are suitable. Spirocyclic azaindole derivatives according to the invention in depot form, in dissolved form or in a plaster, optionally with the addition of agents promoting penetration of the skin, are suitable percutaneous application preparations. Preparation forms that can be used orally or percutaneously can provide for the delayed release of the spirocyclic azaindole derivatives according to the invention. The spirocyclic azaindole derivatives according to the invention can also be employed in parenteral long-acting depot forms, such as for example implants or implanted pumps. In principle other active substances known to the person skilled in the art can be added to the medicaments according to the invention.

The amount of active substance to be administered to the patient varies depending on the patient's weight, on the mode of application, medical indications and the severity of the disease. Normally 0.00005 to 50 mg/kg, preferably 0.01 to 5 mg/kg of at least one spirocyclic azaindole derivative according to the invention are administered.

For all the above forms of the medicaments according to the invention it is particularly preferred if the medicament contains, apart from at least one spirocyclic azaindole derivative, also one further active substance, in particular an opioid, preferably a powerful opioid, in particular morphine, or an anaesthetic, preferably hexobarbital or halothane.

In a preferred form of the medicament a spirocyclic azaindole derivative according to the invention is present as pure diastereomer and/or enantiomer, as racemate, or as a non-equimolar or equimolar mixture of the diastereomers and/or enantiomers.

The ORL-1 receptor and the µ-opioid receptor have been identified in particular in the occurrence of pain. Accordingly, spirocyclic azaindole derivatives according to the invention can be used for the preparation of a medicament for treating pain, in particular acute, neuropathic or chronic pain.

The invention accordingly also provides for the use of a spirocyclic azaindole derivative according to the invention for the preparation of a medicament for treating pain, in particular acute, visceral, neuropathic or chronic pain.

The invention also provides for the use of a spirocyclic azaindole derivative according to the invention for the preparation of a medicament for treating anxiety states, stress and syndromes associated with stress, depression, epilepsy, Alzheimer's disease, senile dementia, catalepsy, general cognitive dysfunctions, learning and memory disorders (as a nootropic), withdrawal symptoms, alcohol and/or drug and/or medicament misuse and/or dependence, sexual dysfunctions, cardiovascular diseases, hypotension, hypertension, tinnitus, pruritus, migraine, impaired hearing, inadequate intestinal motility, eating disorders, anorexia, obesity, locomotor disorders, diarrhoea, cachexia, urinary incontinence, or as a muscle relaxant, anti-convulsant or anaesthetic, or for co-administration in treatment with an opioid analgesic or with an anaesthetic, for diuresis or anti-natriuresis, anxiolysis, for modulating motor activity, for modulating the release of neurotransmitters and treatment of neuro degenerative diseases associated therewith, and for the treatment of withdrawal symptoms and/or for reducing the addiction potential of opioids.

In this connection it may in one of the aforementioned uses be preferred if an employed spirocyclic azaindole derivative is present as pure diastereomer and/or enantiomer, as racemate, or as a non-equimolar or equimolar mixture of the diastereomers and/or enantiomers.

The present invention also provides a process for the treatment, in particular in one of the aforementioned medical indications, of a non-human mammal or person which/who requires treatment for pain, in particular chronic pain, by administration of a therapeutically active does of a spirocyclic azaindole derivative according to the invention or of a medicament according to the invention.

The invention also provides a process for the preparation of a spirocyclic azaindole derivative according to the invention as outlined in the following description and examples.

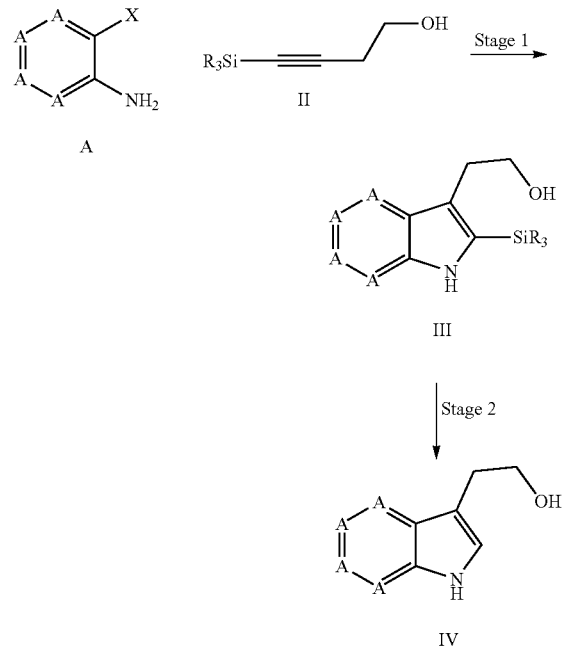

In stage 1 compounds of the general Formula A illustrated above, wherein X denotes a halogen radical or a sulfonic acid ester, particularly preferably iodine, bromine or trifluoromethanesulfonate, are reacted in the form of a Larock indole synthesis with alkynes of the general Formula II in a reaction medium preferably selected from the group consisting of methanol, ethyl acetate, ethanol, isopropanol, n-butanol, dioxane, chloroform, dichloromethane, pyridine, dimethyl sulfoxide, toluene, tetrahydrofuran, dimethylformamide, acetonitrile, diethyl ether, water and corresponding mixtures, particularly preferred selected from the group consisting of dimethylformamide, ethyl acetate, tetrahydrofuran, water and corresponding mixtures, preferably with the addition of at least one palladium catalyst preferably selected from the group consisting of palladium(II) dichloride [$PdCl_2$], bis(triphenylphosphine)-palladium(II) acetate [$Pd(PPh_3)_2(OAc)_2$], bis(triphenylphosphine)-palladium(II) chloride [$PdCl_2(PPh_3)_2$], palladium(II) acetate [$Pd(OAc)_2$; Ac=acetate], bis(acetonitrile)-palladium(II) chloride [$(CH_3CN)_2PdCl_2$], bis(benzonitrile)-palladium(II) chloride [$(PhCN)_2PdCl_2$] and tetrakis(triphenylphosphine)palladium [$(PPh_3)_4Pd$], particularly preferably selected from the group consisting of $Pd(PPh_3)_2(OAc)_2$, $(PPh_3)_4Pd$ and $PdCl_2(PPh_3)_2$, optionally in the presence of at least one phosphine, preferably a phosphine selected from the group consisting of triphenylphosphine, tri-(tert-butyl)-phosphine, triphenylarsine and tri-(ortho-toluoyl)-phosphine, particularly preferably in the presence of triphenylphosphine, optionally with the addition of at least one inorganic salt, preferably with the addition of lithium chloride or tetrabutylammonium chloride, optionally with the addition of at least one inorganic base, preferably selected from the group consisting of potassium carbonate, sodium carbonate, potassium acetate, sodium hydrogen carbonate and caesium carbonate, and/or under the addition of at least one organic base selected from the group consisting of triethylamine, diisopropylamine, diisopropylethylamine and [1,4]-diazabicyclo-[2.2.2]octane at temperatures of preferably −70° C. to 300° C., particularly preferably −70° C. to 150° C., to form compounds of the general Formula III.

Compounds of the general Formula A are commercially obtainable or are known from the literature. Syntheses to form compounds of the general Formula A are described in an exemplary manner in the example part of the specification.

In Stage 2 compounds of the general Formula III are reacted in a reaction medium preferably selected from the group consisting of methanol, ethyl acetate, ethanol, isopropanol, n-butanol, dioxane, chloroform, dichloromethane, pyridine, dimethyl sulfoxide, toluene, tetrahydrofuran, dimethylformamide, acetonitrile, diethyl ether, water and corresponding mixtures, particularly preferably selected from the group consisting of acetonitrile, tetrahydrofuran, methanol, ethanol, ethyl acetate, pyridine, water and corresponding mixtures, in the presence of fluoride selected from the group consisting of tetra-n-butylammonium fluoride, hydrofluoric acid (HF, HF-pyridine), potassium fluoride and/or sodium fluoride, caesium fluoride or in the presence of an organic or inorganic acid, preferably HCl, acetic acid, trifluoroacetic acid, boron trifluoride at temperatures of preferably −70° C. to 300° C., particularly preferably −70° C. to 150° C., to form compounds of the general Formula IV.

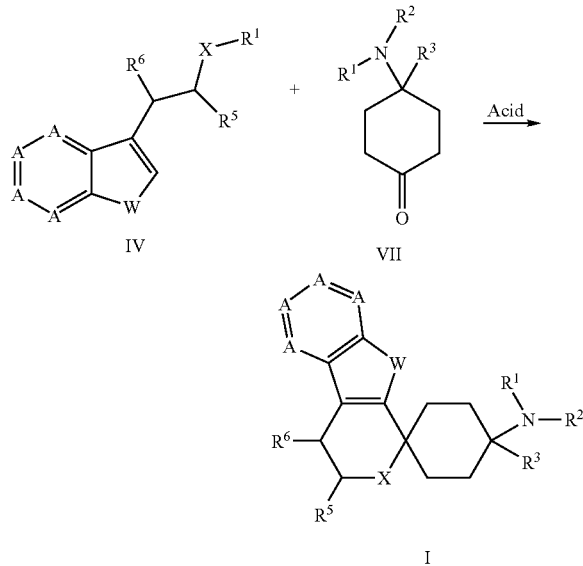

For the preparation of the spirocyclic compounds of the general Formula VIII, ketones of the general Formula VII are reacted with heteroaromatic compounds of the general Formula IV with the addition of at least one organic acid or its trimethylsilyl ester, preferably selected from the group consisting of trifluoromethanesulfonic acid trimethylsilyl ester, trifluoromethanesulfonic acid, methanesulfonic acid, trifluoroacetic acid, acetic acid, phosphoric acid, p-toluenesulfonic acid or an inorganic acid selected from the group consisting of boron trifluoride, indium(III)chloride, titanium tetrachloride, aluminium(III)chloride, or with the addition of at least one transition metal salt, preferably with the addition of at least one transition metal triflate (transition metal trifluoromethanesulfonate), particularly preferably with the addition of at least one transition metal trifluoromethansulfonate selected from the group consisting of scandium(III) trifluoromethanesulfonate, ytterbium (III)trifluoromethansulfonate and indium(III) trifluoromethansulfonate, in a suitable solvent or solvent mixture such as for example dichloromethane, dichloroethane, chloroform, acetonitrile, diethyl ether or nitroethane, at temperatures of 0 to 150° C., optionally with the use of microwaves.

The syntheses of the cyclohexanone derivatives of the general Formula VII are known in the literature (WO04043967, WO0290317, U.S. Pat. No. 4,065,573, Lednicer et al., *J. Med. Chem.*, 23, 1980, 424-430).

EXAMPLES

The following examples serve to illustrate the invention in more detail, but do not restrict the general inventive concept.

The yields of the prepared compounds are not optimised.

All temperatures are uncorrected.

Abbreviations:
d days
DCM dichloromethane
DMF N,N-dimethylformamide
Ether diethyl ether
EtOAc ethyl acetate
H$_2$O water
MeOH methanol
NEt$_3$ triethylamine
RT room temperature
TBAF tetrabutylammonium fluoride
THF tetrahydrofuran
TMEDA N,N,N',N'-tetramethylethylenediamine
Bsp Example
Microwave: Biotage Initiator, 2.45 GHz.

Ketone Structural Units (Building Blocks)

General Structural Units 8-dimethylamino-1,4-dioxa-spiro[4.5]decane-8-carbonitrile Variant 1: 8-dimethylamino-1,4-dioxa-spiro[4.5]decane-8-carbonitrile 40 percent aqueous dimethylamine solution (116 ml, 0.92 mole), cyclohexane-1,4-dione-monoethylene ketal (30 g, 0.192 mole) and potassium cyanide (30 g, 0.46 mole) were added while cooling with ice to a mixture of 4N hydrochloric acid (50 ml) and methanol (30 ml). The mixture was stirred for 74 hours at room temperature and then extracted with diethyl ether (4×100 ml) after the addition of water (80 ml). After concentration by evaporation the residue was taken up in dichloromethane (200 ml) and dried overnight with magnesium sulfate. The organic phase was concentrated by evaporation and the ketal was obtained in a yield of 97% (40 g) as a white solid with a melting point of 86°-88° C.

Variant 2: 8-dimethylamino-1,4-dioxa-spiro[4.5]decane-8-carbonitrile 40 percent aqueous dimethylamine solution (116 ml, 0.92 mole) cyclohexane-1,4-dione-monoethylene ketal (30.0 g, 0.192 mole) and potassium cyanide (30.0 g, 0.46 mole) were added while cooling with ice to a mixture of 4N hydrochloric acid (50 ml) and methanol (30 ml). The mixture was stirred for 74 hours at room temperature and then extracted with diethyl ether (4×100 ml) after the addition of water (80 ml). After concentration by evaporation the residue was taken up in dichloromethane (200 ml) and dried overnight with magnesium sulfate. The organic phase was concentrated by evaporation and the ketal was obtained as a white solid.

Yield: 38.9 g (96%)

Melting point: 86°-88° C.

$^1$H-NMR (DMSO-d$_6$): 1.57 (2H, m); 1.72 (2H; m); 1.85 (2H, m); 1.99 (2H, m); 2.25 (6H, s); 3.87 (4H, m).

$^{13}$C-NMR (DMSO-d$_6$): 30.02; 31.32; 60.66; 63.77; 106.31; 118.40.

8-methylamino-1,4-dioxa-spiro[4.5]decane-8-carbonitrile

40% aqueous methylamine solution (29.0 ml, 0.23 mole), cyclohexane-1,4-dione-monoethylene ketal (7.50 g, 0.048 mole) and potassium cyanide (7.50 g) were added while cooling with ice to a mixture of 4N hydrochloric acid (12.5 ml) and methanol (7.5 ml). The mixture was stirred for 7 days at room temperature. After adding water (20 ml) the mixture was extracted with ether (4×25 ml). After concentrating the solution by evaporation the residue was taken up in dichloromethane (50 ml) and dried overnight with MgSO$_4$. The organic phase was concentrated by evaporation and the ketal was obtained as an oil, which crystallised completely.

Yield: 7.05 g (80%)

$^1$H-NMR (DMSO-d$_6$): 1.54 (2H, m); 1.71 (4H, m); 1.95 (2H, m); 2.30 (3H, d); 2.72 (1H, q); 3.86 (4H, s).

Structural unit Ket-1

Dimethyl-(8-phenyl-1,4-dioxaspiro[4.5]dec-8-yl) amine hydrochloride 8-dimethylamino-1,4-dioxa-spiro[4.5]decane-8-carbonitrile (21 g, 0.1 mole), dissolved in THF (210 ml), was added within 15 minutes while cooling with ice and under argon to a 1.82 M phenylmagnesium chloride solution in THF (109 ml, 0.198 mole) and the mixture was then stirred for 16 hours at room temperature. To work up the reaction mixture saturated ammonium chloride solution (150 ml) was added while cooling with ice and extracted with diethyl ether (3×100 ml). The organic phase was extracted by shaking with water (100 ml) and saturated NaCl solution (100 ml) and concentrated by evaporation. A yellow oil (25.2 g) remained. The crude product was dissolved in ethyl methyl ketone (280 ml) and ClSiMe$_3$ (18.8 ml, 0.15 mole) was added while cooling with ice. After a reaction time of 6 hours dimethyl-(8-phenyl-1,4-dioxaspiro[4.5]dec-8-yl)amine hydrochloride was isolated as a white solid in a yield of 35% (10.5 g).

4-dimethylamino-4-phenylcyclohexanone (Ket-1)

Dimethyl-(8-phenyl-1,4-dioxaspiro[4.5]dec-8-yl)amine hydrochloride (10.5 g, 35.2 mmole) was dissolved in 7.5N hydrochloric acid (36 ml) and stirred for 96 hours at room temperature. After completion of the hydrolysis the reaction mixture was extracted with diethyl ether (2×50 ml). The aqueous phase was made alkaline with 5N sodium hydroxide solution while cooling with ice, extracted with dichloromethane (3×50 ml) and concentrated by evaporation. 4-dimethylamino-4-phenylcyclohexanone (Ket-1) was thus obtained as a yellow solid with a melting point of 1040-108° C. in a yield of 97% (7.4 g).

Structural Unit Ket-2

Dimethyl-(8-thiophen-2-yl-1,4-dioxaspiro[4.5]dec-8-yl)amine hydrochloride 2-iodothiophene (22.9 g, 109 mmole) was dissolved under argon in THF (80 ml) and 2M isopropylmagnesium chloride (35.7 ml, 72 mmole) in THF was added within 30 minutes at 0° C. After a reaction time of 1 hour at 3°-5° C. 8-dimethylamino-1,4-dioxa-spiro[4.5]decane-8-carbonitrile (10 g, 47.6 mmole), dissolved in tetrahydrofuran (20 ml), was added and the reaction mixture was stirred for 20 hours at room temperature. The reaction mixture was worked up by adding saturated NH$_4$Cl solution (85 ml) and extracted with diethyl ether (3×100 ml). The organic phase was extracted by shaking with water (50 ml) and saturated NaCl solution (50 ml) and concentrated by evaporation. A dark brown oil (21.3 g) was obtained. The crude product was dissolved in ethyl methyl ketone (140 ml) and ClSiMe$_3$ (9.1 ml, 71.4 mmole) was added. After a reaction time of 6 hours dimethyl-(8-thiophen-2-yl-1,4-dioxaspiro[4.5]dec-8-yl)amine hydrochloride was isolated as a white, crystalline compound in a yield of 60% (8.74 g).

4-dimethylamino-4-thiophen-2-yl-cyclohexanone (Ket-2)

Dimethyl-(8-thiophen-2-yl-1,4-dioxaspiro[4.5]dec-8-yl) amine hydrochloride (8.68 g, 28.6 hours) and after completion of hydrolysis the reaction mixture was extracted with diethyl ether (2×50 ml). The aqueous phase was made alkaline with 5N sodium hydroxide solution while cooling with ice, extracted with dichloromethane (3×50 ml) and concentrated by evaporation. Ket-2 was thus obtained as a yellow solid with a melting point of 108°-110° C. in a yield of 89% (5.66 g).

Structural Unit Ket-3

4-cyano-4-phenylheptanedioic Acid Dimethyl Ester

Phenylacetonitrile (11.7 g, 0.1 mole) and methyl acrylate (47 ml, 0.5 mole) were added to tert-butanol (60 ml) and heated to boiling point. The source of heat was then removed. Triton B (benzyltrimethylammonium hydroxide, 40% in methanol, 15.2 ml) dissolved in tert-butanol (23 ml) was added dropwise, first of all slowly and then at a faster rate. After the dropwise addition the reaction mixture was boiled under reflux for 4 hours. The reaction mixture was cooled to room temperature overnight. The reaction mixture was worked up by adding toluene (100 ml) and water (70 ml). The organic phase was separated and washed with water (1×70 ml) and saturated sodium chloride solution (1×50 ml). After drying over Na$_2$SO$_4$, the solvent was distilled off in a fume cupboard on account of the strong smell. Purification was carried out by bulb tube distillation at a pressure of 7.8×10$^{-2}$ mbar and at a temperature of 235° C. The desired 4-cyano-4-phenylheptanedioic acid dimethyl ester was obtained in a yield of 21.45 g (72%) as a colourless viscous substance.

5-cyano-2-oxo-5-phenylcyclohexanecarboxylic Acid Methyl Ester 4-cyano-4-phenylheptanedioic acid dimethyl ester (14.45 g, 0.05 mole) was dissolved in dry tetrahydrofuran (350 ml). Sodium tert-butylate (9.6 g, 0.1 mole) was then added in portions. During this addition the reaction mixture turned an orange colour. The reaction mixture was then boiled under reflux for 5 hours. During the boiling a beige-coloured pasty suspension was formed. The reaction mixture was cooled to room temperature overnight. 2.5N acetic acid (170 ml) was slowly added dropwise to the reaction mixture while cooling with ice. Toluene (100 ml) was then added to the reaction mixture. The organic phase was separated and washed with saturated sodium hydrogen carbonate solution (3×70 ml), water (3×50 ml) and sodium chloride solution (1×70 ml). After drying over Na$_2$SO$_4$, the solvent was distilled off on a rotary evaporator and the residue was recrystallised from methanol. The desired product was obtained in a yield of 10.7 g (83%) as a yellow solid with a melting point of 75°-80° C.

4-cyano-4-phenylcyclohexanone 5-cyano-2-oxo-5-phenylcyclohexanecarboxylic acid methyl ester (7.71 g, 0.03 mole) was dissolved in 10 percent H$_2$SO$_4$ and conc. acetic acid (240 ml). The reaction mixture was stirred for 24 hours at 100° C. The course of the reaction was followed by thin layer chromatography. The reaction mixture was worked up by dilution with water (400 ml) while cooling in ice and extracted with ethyl acetate (3×100 ml).

The organic phase was then thoroughly washed with water (6×100 ml), saturated sodium hydrogen carbonate solution (10×100 ml) and saturated sodium chloride solution (1×100 ml). After drying the organic phase over $Na_2SO_4$, the solvent was distilled off on a rotary evaporator. The desired product was obtained in a yield of 5.46 g (92%) with a melting point of 106°-107° C.

8-cyano-8-phenyl-1,4-dioxaspiro[4.5]decane 4-cyano-4-phenylcyclohexanone (5.97 g, 30 mmole) was taken up in toluene (200 ml) and ethylene glycol (4 ml, 71.6 mmole) was added. After addition of p-toluenesulfonic acid (86 mg, 0.5 mmole) the reaction mixture was heated to the boil in a water separator. The course of the reaction was followed by thin layer chromatography. After 20 hours no starting product could be detected any longer by thin layer chromatography. After cooling, the toluene solution was extracted by shaking with water (5×30 ml) and saturated aqueous NaCl solution (3×20 ml) and dried over $Na_2SO_4$. After removing the solvent on a rotary evaporator the desired ketal was obtained in a yield of 6.8 g (94%) as a white solid with a melting point of 108°-110° C.

8-phenyl-1,4-dioxaspiro[4.5]decane-8-carboxylic Acid (Schneider, Woldemar; Krombholz, Gottfried; ARPMAS; Arch. Pharm. (Weinheim Ger.); 313; 6; 1980; 487-498)

8-cyano-8-phenyl-1,4-dioxaspiro[4.5]decane (4.86 g, 20 mmole) was dissolved in ethylene glycol (40 ml), NaOH (4 g, 100 mmole) was added, and the reaction mixture was then boiled under reflux. The course of the reaction was followed by thin layer chromatography. After 20 hours no nitrile could be detected any longer. The reaction mixture was worked up by adding ice (ca. 100 g), was covered with ether (40 ml), and was acidified by slow addition of semi-concentrated HCl (50 ml). The aqueous phase was extracted with ether (3×30 ml). The combined organic extracts were washed with saturated $NH_4Cl$ solution (2×30 ml), dried over $Na_2SO_4$, and finally dried on a rotary evaporator. By recrystallisation of the resultant solid from toluene the desired carboxylic acid was obtained as a crystalline solid with a melting point of 134°-139° C. in a yield of 3.1 g (59%).

8-isocyanato-8-phenyl-1,4-dioxaspiro[4.5]decane 8-phenyl-1,4-dioxaspiro[4.5]decane-8-carboxylic acid (3 g, 11.5 mmole) was added to anisole (30 ml). The resultant suspension was cooled to a temperature of 0° C. in an ice-salt bath and triethylamine (2.25 ml, 16 mmole) was added. A clear solution was formed, which was stirred for a further 15 minutes at 0° C. Phosphoric acid diphenyl ester azide (2.5 ml, 11.5 mmole) was then added to the mixture within 5 minutes. The reaction mixture was stirred for 20 minutes at 0° C., left to cool to RT within a further 20 minutes, and was then heated in an oil bath for 2 hours at 100° C. (bath temperature). The reaction mixture was worked up by distilling off the anisole under an oil pump vacuum. The chromatographic purification was carried out on silica gel with toluene. The desired product was obtained as a crystalline solid with a melting point of 38°-41° C. in a yield of 2.7 g (91%).

Methyl-(8-phenyl-1,4-dioxaspiro[4.5]dec-8-yl)amine $LiAlH_4$ (535 mg, 14.08 mmole) was suspended in dry THF (4 ml) with the exclusion of atmospheric moisture. 8-isocyanato-8-phenyl-1,4-dioxaspiro[4.5]decane (2.29 g, 8.8 mmole, dissolved in 40 ml of dry THF) was then added dropwise within 20 minutes. After the end of the addition the reaction mixture was boiled under reflux for 4 hours. After cooling the reaction mixture, aqueous THF (1 ml $H_2O$ in 3 ml) was first of all carefully added, followed by 1.7 ml of 15% sodium hydroxide solution and finally 5 ml of $H_2O$. The reaction mixture was stirred for 20 minutes and then filtered through diatomaceous earth. The solvent mixture obtained by washing the filter cake several times with ethyl acetate was concentrated by evaporation to dryness on a rotary evaporator. The desired product was obtained in a yield of 2.1 g (97%) as a viscous oil.

4-methylamino-4-phenylcyclohexanone (Ket-3)

(Upjohn_Lednicer, U.S. Pat. No. 4,065,573A1, 1977)

A mixture of conc. HCl (15 ml) and water (8 ml) was poured over methyl-(8-phenyl-1,4-dioxaspiro[4.5]dec-8-yl) amine (2.1 g, 8.4 mmole) and the mixture was stirred for 5 days at RT. The reaction mixture was worked up by dilution with water (20 ml) and extraction with ether (3×30 ml). The ethereal phase was discarded. The aqueous phase was then made alkaline with 2N NaOH and extracted with dichloromethane (3×30 ml). The organic phase thereby obtained was dried over $Na_2SO_4$ and then concentrated by evaporation on a rotary evaporator. The ketone Ket-3 was obtained by chromatographic purification on silica gel with ethyl acetate/ ethanol (4:1) in a yield of 1.38 g (81%) as a solid with a melting point of 32°-38° C.

Structural Unit Ket-4

2-(chloromethyl)thiophene

Conc. HCl solution (25 ml) was added to thiophene (50 g) and the mixture was cooled to 0°-5° C. Aqueous formaldehyde solution (54.8 ml, 40%) was now added dropwise over a period of 4 hours at 0°-15° C. under a constant flow of HCl gas. The reaction mixture was stirred for 10 minutes at RT and ethyl acetate (500 ml) was then added. The organic phase was extracted with saturated $NaHCO_3$ solution (3×250 ml) and water (1×250 ml) and dried over $Na_2SO_4$. Vacuum distillation at 100°-110° C. (oil bath temperature) yielded (60° C. head temperature) the desired product (8 mm Hg).

Yield: 24 g (30%), colourless oil.

2-(thiophen-2-yl)acetonitrile

A mixture of water (90 ml) and NaCN (12.2 g) was added to a solution of 2-(chloromethyl)thiophene 22 g) in DCM (60 ml). The reaction mixture was refluxed at 35°-40° C. for 18 hours. The mixture was cooled to RT and the DCM phase was separated. Extraction was carried out with DCM (2×100 ml) and the combined organic phases were washed with saturated NaCl solution and dried over $Na_2SO_4$. The solvents were removed under reduced pressure and the residue was distilled off at 140°-150° C. (oil bath temperature) (head temperature: 115°-120° C.). Subsequent chromatographic purification ($SiO_2$, 5% EtOAc/n-hexane) yielded the desired product.

Yield: 9.2 g (45%), pale-brown oil.

Ethyl 3-bromopropionate

A solution of ethyl acrylate (200 g) in ether (400 ml) was cooled to 0°-5° C. In a separate reaction vessel bromine (278 ml) was added dropwise to tetraline (213 ml) over a period of 3 hours and the HBr gas thereby formed was passed into the ethyl acrylate solution. The reaction mixture was stirred for 12 hours. The ether was removed under reduced pressure and the residue was distilled at 70° C. (9 mm Hg).

Yield: 360 g (99%), colourless oil.

Ethyl 5-cyano-2-oxo-5-(thiophen-2-yl)cyclohexane Carboxylate

Ethyl-3-bromopropionate (33.8 g) was added to a solution of 2-(thiophen-2-yl)acetonitrile (10 g) in toluene (300 ml) and the mixture was cooled to −10° C. NaNH$_2$ (27 g) was added in portions over a period of 1 hour (the temperature was maintained below 0° C.). The reaction mixture was heated to RT and refluxed for 1 hour (111° C.). Finally the mixture was cooled to 0°-5° C. and AcOH/water (50 ml/100 ml) was added. The toluene phase was separated and the aqueous phase was extracted with toluene (3×200 ml). The combined organic extracts were washed with 5% Na$_2$CO$_3$ solution (1×50 ml) and water (1×00 ml) and dried over Na$_2$SO$_4$. The solvent was removed under reduced pressure.

Yield: 12 g (55%), dark brown oil.

4-cyano-4-(thiophen-2-yl)cyclohexanone

Conc. HCl (60 ml) was added to ethyl 5-cyano-2-oxo-5-(thiophen-2-yl)cyclohexanecarboxylate (12 g) in acetic acid (120 ml). The reaction mixture was refluxed for 3 hours (110° C.-120° C.). The mixture was cooled to 0° C. and adjusted with 2N NaOH-solution (200 ml) until it was neutral (pH ~7).

The aqueous phase was extracted with ethyl acetate (3×150 ml). The combined organic phases were washed with water (1×300 ml) and saturated NaHCO$_3$-Solution (1×300 ml) and dried over Na$_2$SO$_4$. The solvents were removed under reduced pressure and the residue was purified by means of column chromatography (SiO$_2$, 15% EtOAc/n-hexane).

Yield: 37 g (43%), pale yellow solid.

8-cyano-8-(thiophen-2-yl)-1,4-dioxaspiro[4.5]decane

Ethylene glycol (9.08 g) and p-toluenesulfonic acid (0.0139 g) were added to a solution of 4-cyano-4-(thiophen-2-yl)cyclohexanone (15 g) in benzene (120 ml) and the reaction mixture was boiled under reflux for 4 hours at 110° C. on a water separator (Dean-Stark apparatus). The reaction mixture was cooled to RT and the organic phase was washed with aqueous sodium bicarbonate solution (1×150 ml), water (1×150 ml) and saturated NaCl solution (1×150 ml). After drying over Na$_2$SO$_4$, the solvents were removed under reduced pressure.

Yield: 16.5 g (90%), pale yellow solid.

8-(thiophen-2-yl)-1,4-dioxaspiro[4.5]decane-8-carboxylic Acid

KOH (22.48 g) was added to 8-cyano-8-(thiophen-2-yl)-1,4-dioxaspiro[4.5]decane (20 g) in ethylene glycol (240 ml) and the reaction mixture was boiled under reflux for 16 hours at 140°-150° C. The mixture was cooled to RT and then covered with ether (500 ml) at 0°-5° C. Ice-cold water (250 ml) and HCl (30 ml) were added and the pH value of the aqueous phase was adjusted to pH ~2. The organic phase was separated, washed with water (1×300 ml) and saturated NaCl solution (1×300 ml) and dried over Na$_2$SO$_4$. The solvent was removed under reduced pressure.

Yield: 20.5 g (95%), yellow solid.

8-isocyanato-8-(thiophen-2-yl)-1,4-dioxaspiro[4.5]decane

TEA (14.1 ml) and DPPA (32.38 g) were added to a solution of 8-(thiophen-2-yl)-1,4-dioxaspiro[4.5]decane-8-carboxylic acid (26 g) in toluene (221 ml) and the reaction mixture was heated for 30 minutes at 60°-70° C. The toluene was then removed under reduced pressure and the residue was purified by means of column chromatography (wet SiO$_2$, 1$^{st}$ run: 10% EtOAc/n-hexane, 2$^{nd}$ run: 10% EtOAc/hexane).

Yield: 14 g (54%), pale green oil.

N-methyl-8-(thiophen-2-yl)-1,4-dioxaspiro[4.5]decan-8-amine 8-isocyanato-8-(thiophen-2-yl)-1,4-dioxaspiro[4.5]decane (4 g) was dissolved in dry THF (140 ml) and the solution was cooled to 0°-10° C. LAH (4 g) was added in portions over a period of 30 minutes and the reaction mixture was heated for a further 30 minutes at 60° C. The mixture was cooled to 0°-10° C. and saturated ammonium chloride solution (100 ml) was added. The mixture was now filtered through celite and washed with ethyl acetate (3×150 ml). After removing the solvents the crude product was taken up in ethyl acetate (200 ml) and stirred for 3 minutes at 0°-10° C. The ethyl acetate phase was separated, and aqueous phase was made alkaline (pH 10-14) with saturated NaOH solution and extracted with ethyl acetate (3×200 ml). The combined organic phases were dried over Na$_2$SO$_4$. The solvent was removed under reduced pressure.

Yield: 7.5 g (56%), colourless solid.

4-methylamino-4-thiophen-2-ylcyclohexanone (Ket-4)

A mixture of conc. HCl (15 ml) and water (8 ml) was added to N-methyl-8-(thiophen-2-yl)-1,4-dioxaspiro[4.5]decan-8-amine (2 g, 7.9 mmole) and stirred for 5 days at RT. The reaction mixture was worked up by dilution with water (30 ml) and extraction with ether. The ethereal phase was discarded. The aqueous phase was then made alkaline with 2N NaOH and extracted with dichloromethane (3×30 ml). The organic phase thereby obtained was dried over Na$_2$SO$_4$ and then concentrated by evaporation on a rotary evaporator. The residue was purified by column chromatography (silica gel 60 (50 g); 500 ml ethyl acetate/ethanol (5:1)] and Ket-4 was obtained in a yield of 1.4 g (85%) as a solid with a melting point of 72°-74° C.

Structural Unit Ket-5

(8-benzo[1,3]dioxol-5-yl-1,4-dioxa-spiro[4.5]dec-8-yl)-dimethylamine Hydrochloride 1M 3,4-(methylenedioxy)phenylmagnesium bromide solution in toluene/THF (1:1) (62.5 ml, 62.5 mmole) was added dropwise at 5°-10° C. within 15 minutes under argon and while cooling with ice to a solution of 8-dimethylamino-1,4-dioxa-spiro[4.5]decane-8-carbonitrile (5.25 g, 25 mmole) in absolute THF (75 ml) and then stirred at RT for 20 hours. The reaction mixture was worked up by adding 20% ammonium chloride solution (20 ml) and water (25 ml) while cooling with ice and the mixture was extracted with ether (3×50 ml). The organic phase was washed with water and saturated sodium chloride solution, dried over sodium sulphate, and concentrated by evaporation in vacuo. A colourless oil (11.26 g) remained, which was dissolved in ethyl methyl ketone (35 ml) and to which trimethylchlorosilane (4.75 ml, 37.5 mmole) was added while cooling with ice. The mixture was stirred in an open flask for 5 hours at RT. A colourless solid then precipitated out, which was suction filtered and dried in air.

Yield: 2.7 g (32%).

1H-NMR (DMSO-d6): 1.71 (2H, t); 1.72 (2H; d); 2.09 (2H, t); 2.43 (6H, s); 2.84 (2H, d); 3.82 (4H, m); 6.11 (2H, s); 7.07 (1H, d); 7.15 (1H, d); 7.32 (1H, s); 10.74 (1H, bs).

4-benzo[1,3]dioxol-5-yl-4-dimethylamino-cyclohexanone (Ket-5)

6N hydrochloric acid (10 ml) was added to (8-benzo[1,3]dioxol-5-yl-1,4-dioxa-spiro[4.5]dec-8-yl)-dimethylamine hydrochloride (2.70 g, 7.91 mmole) and stirred overnight at RT. After completion of the hydrolysis the reaction mixture was extracted with ether (2×20 ml), the aqueous solution was made alkaline with 5N sodium hydroxide solution while cooling with ice, the reaction mixture was extracted with dichloromethane (3×50 ml), and the organic phase was dried over sodium sulfate and concentrated by evaporation in vacuo.

Yield (Ket-5): 1.99 g (96%), colourless crystals.
Melting point: 122°-124° C.
1H-NMR (DMSO-d6): 2.01 (6H, s); 2.10 (4H, m); 2.43 (6H, m); 6.01 (2H, s); 6.88 (2H, m); 7.02 (1H, s).
13C-NMR (DMSO-d6): 32.39; 36.68; 38.88; 58.82; 100.76; 107.12; 107.67; 120.46; 131.34; 145.69; 147.03; 210.27.

Structural Unit Ket-6

2-iodobenzo[b]thiophene

Butyllithium 1.6M in hexane (112.5 ml, 180 mmole) and absolute ether (70 ml) were placed in a 500 ml three-necked flask under an argon atmosphere and cooled in an ice bath to 0° C. Benzothiophene (20.1 g, 150 mmole) dissolved in absolute ether (40 ml) was then added dropwise within 30 minutes while cooling with ice and the mixture was stirred for 2.5 hours in an ice bath. The reaction mixture was left overnight in a cold cabinet. Iodine (75.0 g) and absolute ether (50 ml) were placed in a 500 ml capacity 3-necked flask under an argon atmosphere and the solution of the lithium compound was added dropwise while cooling with ice. The reaction mixture was slowly heated to room temperature, hydrolysed with water, washed with sodium thiosulfate solution and the organic phase was dried over sodium sulfate. The reaction solution was then concentrated by evaporation in vacuo and purified by means of flash chromatography with cyclohexane.

Yield: 24.1 g (62%), semi-solid, pale brown crystals
$^1$H-NMR (DMSO-d$_6$): 7.32 (2H, m); 7.75 (1H, s); 7.81 (1H, m); 7.93 (1H, m).

(8-benzo[b]thiophen-2-yl-1,4-dioxa-spiro[4.5]dec-8-yl)-dimethylamine Hydrochloride Mg (238 mg) in absolute ether (2 ml) was placed in a 100 ml three-necked flask under argon and 2-iodo-benzo[b]thiophene (2.51 g, 9.6 mmole) in absolute ether (8 ml) was then slowly added dropwise. After adding absolute ether (10 ml) the reaction mixture was boiled for 5 hours under reflux. The reaction solution was cooled in an ice bath and 8-dimethylamino-1,4-dioxa-spiro[4.5]decane-8-carbonitrile (1.03 g, 4.9 mmole) in THF (10 ml) was then added dropwise at 10° C. The reaction mixture was stirred overnight at room temperature, NH$_4$Cl solution (5 ml) and water (7 ml) were added, and the mixture was extracted with ether (3×30 ml). The organic phase was washed with water (30 ml) and then with saturated NaCl solution (20 ml), dried over Na$_2$SO$_4$, and concentrated by evaporation in vacuo.

Yield: 1.99 g (66%)
The crude product was dissolved in ethyl methyl ketone (19 ml), trimethylchlorosilane (1.63 ml, 12.8 mmole) was added while cooling with ice, and the mixture was stirred for 5 hours at room temperature. The precipitate formed was filtered off under suction and dried in vacuo.

Yield: 600 mg (35%)
$^1$H-NMR (DMSO-d$_6$): 1.46 (2H, m); 1.79 (2H, m); 2.37 (2H, m); 2.63 (6H, s); 2.75 (2H, m); 7.47 (2H, m); 7.91 (1H, s); 7.95 (1H, m); 8.06 (1H, m); 11.40 (1H, s).
$^{13}$C-NMR (DMSO-d$_6$): 30.43; 31.13; 37.84; 63.88; 66.42; 105.84; 122.48; 124.55; 124.89; 125.71; 128.99; 135.00; 138.91; 139.58.

4-benzo[b]thiophen-2-yl-4-dimethylamino-cyclohexanone (Ket-6)

The 8-benzo[b]thiophen-2-yl-1,4-dioxa-spiro[4.5]dec-8-yl)-dimethylamine hydrochloride (0.60 g, 1.7 mmole) was dissolved in water (0.8 ml), conc. hydrochloric acid (1.04 ml, 151 mmole) was added, and the mixture was stirred for 3 days at room temperature. After completion of the hydrolysis the reaction mixture was extracted with diethyl ether (2×25 ml) and the aqueous phase was made alkaline with 5N sodium hydroxide solution, extracted with dichloromethane (3×25 ml), dried over sodium sulfate and concentrated by evaporation in vacuo.

Yield (Ket-6): 0.44 g (95%)
$^1$H-NMR (DMSO-d$_6$): 2.19 (10H, m); 2.52 (4H, m); 7.35 (3H, m); 7.84 (1H, m); 7.91 (1H, m).
$^{13}$C-NMR (DMSO-d$_6$): 33.74; 36.51; 38.05; 58.60; 121.87; 121.94; 123.35; 124.02; 124.16; 138.19; 139.17; 144.28; 209.50.

Structural Unit Ket-7

Variant 1: [8-(3-fluorophenyl)-1,4-dioxaspiro[4.5]dec-8-yl]dimethylamine Hydrochloride 0.5M 3 Fluorophenylmagnesium bromide solution in THF (3.750 ml, 375 mmole) was added under argon and while cooling with ice to a solution of 8-dimethylamino-1,4-dioxaspiro[4.5]decane-8-carbonitrile (19.8 g, 94 mmole) in THF (100 ml) and the mixture was then stirred for 16 hours at room temperature. The reaction mixture was worked up by adding saturated ammonium chloride solution (150 ml) and water (60 ml) while cooling with ice and extracted with diethyl ether (3×100 ml). The organic phase was extracted by shaking with water (50 ml) and saturated NaCl solution (50 ml) and concentrated by evaporation. A brown oil (26.5 g) remained, which apart from the phenyl compound 4 also contained the ketal 2. The crude product was dissolved in ethyl methyl ketone (156 ml) and ClSiMe$_3$ (17.8 ml, 141 mmole) was added while cooling with ice. After a reaction time of 6 hours the hydrochloride was isolated in a yield of 55% (16.3 g) as a white solid with a melting point of 275°-278° C.

Variant 2: [8-(3-fluorophenyl)-1,4-dioxa-spiro[4.5]dec-8-yl]-dimethylamine Hydrochloride A solution of 1-bromo-3-fluorobenzene (5.00 g, 28.6 mmole) in absolute ether (15 ml) was added dropwise to a suspension of magnesium (694 mg, 28.6 mmole) in absolute ether (10 ml) at such a rate that the ether boiled. After completion of the addition the reaction mixture was stirred for 10 minutes at RT, following which the magnesium had completely dissolved. The reaction solution was cooled in an ice bath and 8-dimethylamino-1,4-dioxa-spiro[4.5]decane-8-carbonitrile (3.00 g, 14.3 mmole) in absolute THF (30 ml) was added dropwise at 10° C. The reaction mixture was stirred at room temperature overnight, 20% $NH_4Cl$-solution (20 ml) and water (30 ml) were added thereto while cooling with ice, and the mixture was extracted with ether (3×50 ml). The organic phase was washed with water (50 ml) and then with saturated NaCl solution (50 ml), dried over $Na_2SO_4$ and concentrated by evaporation in vacuo. The crude product was dissolved in ethyl methyl ketone (25 ml), $ClSiMe_3$ (3.2 ml, 25 mmole) was added while cooling with ice, and the mixture was stirred at room temperature for 5 hours. The precipitate formed was filtered off and dried in vacuo.

Yield: 2.8 g (62%)

$^1$H-NMR (DMSO-$d_6$): 1.91 (8H, m); 2.54 (6H, s); 3.91 (4H, d); 7.37 (1H, m); 7.61 (3H, m).

Variant 1:
4-dimethylamino-4-(3-fluorophenyl)-cyclohexanone (Ket-7)

[8-(3-fluorophenyl)-1,4-dioxa-spiro[4.5]dec-8-yl]-dimethylamine hydrochloride (7.2 g, 22.75 mmole) was dissolved in water (9.6 ml), conc. hydrochloric acid (14 ml, 455 mmole) was added and the mixture was stirred for 4 days at room temperature. After completion of the hydrolysis the reaction mixture was extracted with diethyl ether (2×50 ml), the aqueous phase was make alkaline with 5N sodium hydroxide solution while cooling with ice, whereupon the product precipitated out. The ketone Ket-7 was isolated as a yellow solid with a melting point of 83°-88° C. and in a yield of 50% (6.05 g).

Variant 2:
4-dimethylamino-4-(3-fluorophenyl)-cyclohexanone (Ket-7)

[8-(3-fluorophenyl)-1,4-dioxa-spiro[4.5]dec-8-yl]-dimethylamine hydrochloride (2.80 g, 8.86 mmole) was dissolved in water (3.7 ml), conc. hydrochloric acid (5.5 ml) was added and the mixture was stirred for 4 days at RT. After completion of the hydrolysis the reaction mixture was extracted with ether (2×10 ml), the aqueous solution was made alkaline with 5N sodium hydroxide solution while cooling with ice, the reaction mixture was extracted with dichloromethane (3×50 ml), and the organic phase was dried over sodium sulfate and concentrated by evaporation in vacuo. The crude product was purified by flash chromatography with $CHCl_3$/MeOH (20:1).

Yield (Ket-7): 676 mg (32%), colourless solid

Melting point: 62-67° C.

$^1$H-NMR (DMSO-$d_6$): 2.02 (6H, s); 2.12 (5H, m); 2.45 (3H, m); 7.24 (3H, m); 7.43 (1H, m).

Structural Unit Ket-8

Dimethyl-(8-m-tolyl-1,4-dioxa-spiro[4.5]dec-8-yl)-amine Hydrochloride 8-dimethylamino-1,4-dioxa-spiro[4.5]decane-8-carbonitrile (8.4 g, 40 mmole) in absolute THF (150 ml) was placed in a 500 ml three-necked flask under argon and while cooling with ice. m-tolylmagnesium bromide, 1M solution in THF (100 ml, 100 mmole) was added dropwise at 0° C. within 15 minutes. The reaction mixture was then stirred for 16 hours at room temperature.

Ammonium chloride solution (20%, 37 ml) and water (50 ml) were added to the reaction mixture while cooling with ice, and the mixture was extracted with ether (3×50 ml).

The organic phase was washed with water (50 ml) and saturated NaCl-Solution, dried over sodium sulfate, and concentrated by evaporation in vacuo. The crude yield was 11.25 g (brown oil).

The crude product was dissolved in ethyl methyl ketone (60 ml) and trimethylchlorosilane (7.6 ml, 60 mmole) was added at 0° C. After stirring for 5 hours at room temperature the precipitated product was suction filtered and washed with a small amount of cold ethyl methyl ketone.

Yield: 5.64 g (45%), white solid.

Melting point: 230-234° C.

1H-NMR (DMSO-d6): 1.19 (2H, t); 1.67 (2H; d); 2.13 (2H, t); 2.44 (9H, m); 2.89 (2H, d); 3.87 (4H, m); 7.43 (4H, m); 10.82 (1H, bs).

4-dimethylamino-4-m-tolyl-cyclohexanone (Ket-8)

Dimethyl-(8-m-tolyl-1,4-dioxa-spiro[4.5]dec-8-yl)-amine hydrochloride (2.76 g, 10 mmole) was dissolved in water (4.2 ml), conc. hydrochloric acid (6.15 ml) was added and the mixture was stirred for 76 hours at RT.

The solution was extracted with ether (2×25 ml), and the ether phase was discarded. 5N NaOH was added dropwise to the aqueous solution until it was alkaline. The solution was then extracted with dichloromethane (3×25 ml), and the organic phase was washed with water (25 ml), dried over $Na_2SO_4$ and concentrated by evaporation.

Yield Ket-8: 1.69 g (73%), yellow oil

1H-NMR (DMSO-d6): 2.05 (10H, m); 2.35 (3H, s); 2.52 (2H, m); 2.62 (2H, m); 7.12 (1H, m); 7.23 (3H, m).

Structural Unit Ket-9

Variant 1: (8-butyl-1,4-dioxa-spiro[4.5]dec-8-yl)-dimethylamine Hydrochloride 8-dimethylamino-1,4-dioxa-spiro[4.5]decane-8-carbonitrile (10.5 g, 50 mmole) was added to THF (150 ml) while cooling with ice and under argon. 2M butylmagnesium chloride in THF (62.5 ml, 125 mmole) was added dropwise within 15 minutes and the mixture was stirred for 16 hours at RT. 20% ammonium chloride solution (37 ml) and water (50 ml) were added to the reaction mixture while cooling with ice, and extracted with ether (3×50 ml). The organic phase was washed with water (1×50 ml) and saturated sodium chloride solution (1×50 ml), and the organic phase was dried over $Na_2SO_4$ and concentrated by evaporation in vacuo.

The crude product (2.05 g) was dissolved in ethyl methyl ketone (75 ml), $ClSiMe_3$ (9.5 ml, 75 mmole) was added while cooling with ice, and the reaction mixture was stirred for 6 hours at RT. The precipitated white product was suction filtered and dried in vacuo.

Yield: 3.1 g (22%)

$^1$H-NMR (DMSO-$d_6$): 0.91 (3H, t); 1.31 (4H, m); 1.56 (2H, m); 1.75 (8H, m); 2.64 (6H, s); 3.87 (4H, s); 9.87 (1H, s).

Variant 1: 4-butyl-4-dimethylamino-cyclohexanone (Ket-9)

8-butyl-1,4-dioxa-spiro[4.5]dec-8-yl)-dimethylamine hydrochloride (3.10 g, 11.1 mmole) was placed in $H_2O$ (4.7 ml) and conc. HCl (7 ml) and the mixture was stirred for 24 hours at RT. The reaction mixture was extracted with ether (1×15 ml), and the aqueous phase was adjusted alkaline with 5N NaOH while cooling with ice and extracted with dichloromethane (3×20 ml). The organic phase was dried over $Na_2SO_4$ and concentrated by evaporation in vacuo.

Yield: 1.96 g (89%), oil $^1$H-NMR (DMSO-$d_6$): 0.88 (3H, t); 1.23 (4H, m); 1.40 (2H, m); 1.68 (2H, m); 1.91 (2H, m); 2.31 (2H, m); 2.22 (6H, s); 2.42 (2H, m).

$^{13}$C-NMR (DMSO-$d_6$): 13.91; 23.21; 26.06; 29.53; 31.07; 37.04; 38.88; 55.36; 210.37.

Variant 2: (8-butyl-1,4-dioxa-spiro[4.5]dec-8-yl)-dimethylamine Hydrochloride 2M n-butylmagnesium chloride solution in THF (228 ml, 0.456 mole) was slowly added under argon and while cooling with an ice/salt mixture to a solution of 8-dimethylamino-1,4-dioxa-spiro[4.5]decane-8-carbonitrile (38.3 g, 0.182 mole) in absolute tetrahydrofuran (420 ml). In this connection the reaction temperature should not rise above 10° C. The reaction mixture was then stirred for 16 hours at room temperature, a brownish clear solution being formed. The reaction mixture was worked up by the dropwise addition of saturated ammonium chloride solution (150 ml) while cooling with ice (0°-10° C.). A white solid was thereby formed, which was dissolved by adding water (approximately 250 ml). The reaction mixture was extracted with diethyl ether (4×100 ml). The organic phase was washed with water (100 ml) and saturated NaCl-Solution (100 ml), dried and concentrated by evaporation. A yellow oil (44.5 g) remained, which apart from the desired butyl compound also contained the educt nitrile. The crude product was dissolved in ethyl methyl ketone (275 ml), ClSiMe$_3$ (32 ml, 0.245 mole) was added while cooling with ice, and the mixture was stirred in an open flask at room temperature. The hydrochloride was separated by filtering several times at 2-hourly intervals. After a reaction time of 6 to 8 hours (8-butyl-1,4-dioxa-spiro[4.5]dec-8-yl)-dimethylamine hydrochloride was isolated in a yield of 82% (41.8 g) as a white solid.

Variant 2: 4-butyl-4-dimethylamino-cyclohexanone (Ket-9)

(8-butyl-1,4-dioxa-spiro[4.5]dec-8-yl)-dimethylamine hydrochloride (41.8 g, 0.15 mmole) was dissolved in water (78 ml) and 37% hydrochloric acid (100 ml, 1.2 mole) was added while stirring and cooling with ice. The clear reaction mixture was stirred for 7 days at room temperature. After completion of the hydrolysis the reaction mixture was extracted with diethyl ether (2×70 ml). The organic extracts were discarded. The aqueous phase was made alkaline with 5N sodium hydroxide solution (approximately 250 ml) while cooling with ice, and vigorously stirred. The solution was extracted with diethyl ether (3×100 ml). The combined organic extracts were washed with water (2×70 ml), dried and concentrated by evaporation. 4-butyl-4-dimethylamino-cyclohexanone (Ket-9) was obtained as a pale brown oil in a yield of 96% (28.4 g). The yield of ketone—referred to the ketal used in the first stage—was 75%.

Structural Unit Ket-10

Dimethyl-(8-phenethyl-1,4-dioxa-spiro[4.5]dec-8-yl) amine Hydrochloride 1M 2-phenylethylmagnesium chloride solution in THF (550 ml, 550 mmole) was added within 15 minutes under argon and while cooling with ice to a solution of 8-dimethylamino-1,4-dioxa-spiro[4.5]decane-8-carbonitrile (39 g, 186 mmole) in THF (300 ml) and the mixture was then stirred for 16 hours at room temperature. The reaction mixture was worked up by adding saturated ammonium chloride solution (295 ml) and water (120 ml) while cooling with ice, and was extracted with diethyl ether (3×150 ml). The organic phase was washed with water (100 ml) and saturated NaCl solution (100 ml) and then concentrated by evaporation. A brown oil remained (60.4 g). The crude product was dissolved in ethyl methyl ketone (310 ml) and ClSiMe$_3$ (35.6 ml, 282 mmole) was added while cooling with ice. After 16 hours at RT the resultant solid product was suction filtered and washed with ethyl methyl ketone.

Yield: 50 g (83%).

Melting point: 275-278° C.

Dimethylamino-4-phenethylcyclohexanone (Ket-10)

Dimethyl-(8-phenethyl-1,4-dioxa-spiro[4.5]dec-8-yl) amine hydrochloride (50 g, 154 mmole) was dissolved in water (60 ml), conc. hydrochloric acid (97.2 ml, 3.16 mole) was added, and the mixture was stirred for 4 days at room temperature. After completion of the hydrolysis the reaction mixture was extracted with diethyl ether (2×100 ml) and the aqueous phase was made alkaline with 5N sodium hydroxide solution while cooling with ice, whereupon a solid precipitated out. This was suction filtered, washed with $H_2O$ (3×20 ml) and then dried.

Yield Ket-10: 25.3 g (67%), yellow solid.

Melting point: 60° C.

Structural Unit Ket-12

This structural unit was obtained under the specified reaction conditions instead of the desired target product. It is obvious that (8-ethyl-1,4-dioxa-spiro[4.5]dec-8-yl)-dimethylamine hydrochloride can also be prepared in a targeted manner from ethylmagnesium bromide and 8-dimethylamino-1,4-dioxa-spiro[4.5]decane-8-carbonitrile.

(8-ethyl-1,4-dioxa-spiro[4.5]dec-8-yl)-dimethylamine Hydrochloride

A mixture of ethyl bromide (30.0 g, 0.3 mole) and 3-bromopyridine (16.0 g, 0.1 mole) was added dropwise to magnesium powder (10.0 g) in diethyl ether (50 ml). After the Grignard reaction had gone to completion, 8-dimethylamino-1,4-dioxa-spiro[4.5]decane-8-carbonitrile (10.5 g, 47.6 mmole) in THF (80 ml) was added within 15 minutes at 0° C. to the grey solution and the mixture was stirred overnight at RT. 20% ammonium chloride solution (50 ml) and water (50 ml) were then added to the reaction solution while cooling with ice. The reaction solution was diluted with diethyl ether (100 ml), and the organic phase was separated and the aqueous phase was extracted twice with Et$_2$O (100 ml). The combined organic phases were washed with water (50 ml) and NaCl solution (50 ml), dried over Na$_2$SO$_4$, filtered and the solvent was removed in vacuo. The residue was taken up in 2-butanone (200 ml) and Me$_3$SiCl (10 ml) was added at 0° C. The reaction solution was stirred for 5 hours under exclusion of moisture and the precipitated solid was suction filtered.

Yield: 6.8 g (64%), pale brown solid $^1$H-NMR (DMSO-$d_6$): 0.94 (3H, t); 1.51-1.60 (2H, m); 1.77-1.86 (8H, m); 2.64 (6H, 2 s); 3.83-3.89 (4H, m).

4-dimethylamino-4-ethyl-cyclohexanone (Ket-12)

(8-ethyl-1,4-dioxa-spiro[4.5]dec-8-yl)-dimethylamine hydrochloride (6.67 g, 0.026 mmole) was dissolved in 6N HCl (40 ml) and stirred overnight at room temperature. The reaction mixture was extracted twice with diethyl ether (100 ml). The reaction mixture was then made alkaline with 5N NaOH while cooling with ice and extracted a further three times with Et$_2$O (100 ml). The combined organic phases were dried over Na$_2$SO$_4$, filtered, and the solvent was removed in vacuo.

Yield: 4.16 g (92%), brown oil $^1$H-NMR (DMSO-d$_6$): 0.81 (3H, t); 1.43-1.50 (2H, q); 1.67-1.89 (2H, m); 1.83-1.89 (2H, m); 1.99-2.06 (2H, m); 2.22 (6H, 2 s); 2.39-2.43 (4H, m).

$^{13}$C-NMR (DMSO-d$_6$): 8.71; 21.99; 30.41; 36.17; 37.07; 38.66; 55.53; 210.57.

Structural Unit Ket-13

4-(8-benzyl-1,4-dioxaspiro[4.5]dec-8-yl)morpholine

In a heated flask a solution of morpholine (958 mg, 0.96 ml, 11 mmole), 1,4-dioxaspiro[4.5]dec-8-one (1.56 g, 10 mmole) and 1,2,3-triazole (829 mg, 12 mmole) in toluene (10 ml) was heated for 6 hours under reflux in a water separator. This solution was then added dropwise under argon to a 2 M solution of benzylmagnesium chloride in tetrahydrofuran (20 ml, 40 mmole) at such a rate that the internal temperature remained below 24° C. The mixture was stirred for 2 hours at room temperature and then added dropwise, while cooling with ice and water, to 20% ammonium chloride solution (25 ml). The organic phase was separated and the aqueous phase was extracted with diethyl ether (3×20 ml). The combined organic phases were washed with 2 N sodium hydroxide solution (40 ml) and water (40 ml), dried with sodium sulfate, and concentrated by evaporation in vacuo. The crude product (4 g) was purified by flash chromatography (400 g, 20×7.5 cm) with ethyl acetate/cyclohexane (1:3).

Yield: 2.87 g (90%), white crystals

Melting point: 97-101° C.

$^1$H-NMR (CDCl$_3$): 1.35-1.52 (m, 4H); 1.72-1.96 (m, 4H); 2.61-2.66 (m, 4H); 2.67 (s, 2H); 3.68-3.75 (m, 4H); 3.78-3.92 (m, 4H); 7.08-7.34 (m, 5H).

4-benzyl-4-morpholin-4-ylcyclohexanone (Ket-13)

6 M hydrochloric acid (5 ml) was added to a solution of 4-(8-benzyl-1,4-dioxaspiro[4.5]dec-8-yl)morpholine (1.00 g, 3.15 mmole) in acetone (5 ml). After 24 hours further 6 M hydrochloric acid (2.5 ml) was added to the reaction solution, which was stirred for a further 3 days at room temperature, following which it was made alkaline (pH ~9) with 25% potassium carbonate solution and extracted with diethyl ether (3×20 ml). The combined organic phases were dried with sodium sulfate and concentrated by evaporation in vacuo.

Yield: 753 mg (87%), white solid (Ket-13)

Melting point: 124-127° C.

$^1$H-NMR (CDCl$_3$): 1.47-1.72 (m, 2H); 1.98-2.14 (m, 4H); 2.48-2.68 (m, 2H); 2.70-2.77 (m, 2H); 2.78 (s, 4H); 3.72-3.81 (s, 4H); 7.12-7.36 (m, 5H).

Structural Unit Ket-14

1-chloro-3-methoxypropane (Letsinger; Schnizer; J. Org. Chem.; 16; 1951; 704, 706)

3-methoxypropan-1-ol (47.1 g, 50 ml, 0.523 mole) was dissolved in pyridine (41.3 g, 42.6 ml, 0.523 mole), cooled to 10° C., and thionyl chloride (93.3 g, 56.9 ml, 0.784 mole) was added dropwise at 10°-30° C. while stirring vigorously. A solid precipitate thereupon precipitated out, and the mixture was then stirred for 3 hours at 65° C.

The reaction mixture was poured onto a mixture of ice (130 g) and conc. HCl (26 ml). The aqueous solution was extracted with ether (2×20 ml) and the combined organic phases were washed with K$_2$CO$_3$ solution. On adding the drying agent K$_2$CO$_3$ a vigorous formation of gas was observed, and the solution was therefore left to stand overnight. The drying agent was filtered off and the organic phase was washed with K$_2$CO$_3$ solution until it was alkaline. The organic phase was separated, washed with water and dried over K$_2$CO$_3$, filtered, and distilled at normal pressure.

Boiling point: 113° C.

Yield: 41.2 g (72%), colourless liquid $^1$H-NMR (DMSO-d$_6$): 1.93 (2H, m); 3.23 (3H; s); 3.44 (2H, t); 3.66 (2H, t).

[8-(3-methoxypropyl)-1,4-dioxa-spiro[4.5]dec-8-yl]-dimethylamine

A solution of 1-chloro-3-methoxypropane (10.0 g, 92 mmole) in absolute ether (15 ml) was added dropwise under an argon atmosphere and while heating intermittently to magnesium (10.0 g, 92 mmol)e and 12 in absolute diethyl ether (30 ml). The reaction mixture was then stirred under reflux for 60 minutes, after which the magnesium had not completely dissolved.

A solution of 8-dimethylamino-1,4-dioxa-spiro[4.5]decane-8-carbonitrile (9.68 g, 46 mmole) in absolute THF (30 ml) was added dropwise while cooling with ice. A viscous precipitate thereby formed, and 100 ml of absolute THF was therefore added to achieve a better mixing. The mixture was stirred for 24 hours at room temperature. 20% NH$_4$Cl solution (100 ml) and water (120 ml) were added while cooling with ice to the reaction mixture, and the organic phase was separated and the aqueous phase was extracted with ether (3×120 ml).

The combined organic phases were washed with saturated NaCl solution (120 ml) and water (120 ml), dried over Na$_2$SO$_4$, and concentrated by evaporation in vacuo. The crude yield was 10.8 g of brown oil.

9.8 g of crude product were purified by flash chromatography with CHCl$_3$/MeOH (50:1⇒20:1⇒9:1).

Yield: 8.11 g (75%), yellow oil $^1$H-NMR (DMSO-d$_6$): 1.44 (8H, m); 1.62 (4H; m); 2.25 (6H, s); 3.21 (3H, s); 3.31 (2H, m); 3.82 (4H, s).

$^{13}$C-NMR (DMSO-d$_6$): 23.99; 26.52; 28.87; 29.88; 36.97; 55.24: 57.67; 63.40; 72.62; 108.07.

4-dimethylamino-4-(3-methoxypropyl)-cyclohexanone (Ket-14)

[8-(3-methoxypropyl)-1,4-dioxa-spiro[4.5]dec-8-yl]-dimethylamine (8.11 g, 31.5 mmole) was dissolved in water (12 ml), conc. HCl (19.5 ml) was added while cooling with ice, and the reaction mixture was stirred for 3 days at room temperature. The reaction mixture was washed with ether (2×75 ml). The solution was then made alkaline with 5N NaOH and extracted with dichloromethane (3×75 ml). The combined organic phases were washed with water (75 ml), dried over Na$_2$SO$_4$, filtered, and the solvent was removed in vacuo.

Yield: 6.03 g (90%), yellow oil $^1$H-NMR (DMSO-d$_6$): 1.44 (4H, m); 1.68 (2H; m); 1.88 (2H, m); 2.00 (1H, m); 2.05 (1H, m); 2.20 (6H, s); 2.41 (2H, m); 3.22 (3H, s); 3.28 (2H, m).

$^{13}$C-NMR (DMSO-d$_6$): 24.01; 26.34; 30.88; 36.15; 37.06; 55.26: 57.70; 72.55; 210.39.

Structural Unit Ket-15

8-azetidin-1-yl-1,4-dioxaspiro[4.5]decane-8-carbonitrile

Firstly 1,4-dioxaspiro[4,5]decan-8-one (4.84 g, 31 mmole) followed by potassium cyanide (4.85 g, 74.4 mmole) in water (15 ml) were added while cooling with ice to a mixture of 4 N hydrochloric acid (8.1 ml), methanol (4.9 ml) and azetidine (8.5 g, 10 ml, 149 mmole). The mixture was stirred for 5 days at room temperature, water (50 ml) was then added, and the mixture was extracted with diethyl ether (3×50 ml). The combined organic phases were dried with sodium sulfate and concentrated by evaporation in vacuo.

Yield: 6.77 g (98%), oil
$^1$H-NMR (DMSO-d$_6$): 1.45-1.63 (m, 4H); 1.67-1.82 (m, 4H); 1.99 (q, 2H, J=7.1 Hz); 3.21 (t, 4H, J=7.1 Hz); 3.86 (s, 4H).

1-(8-phenyl-1,4-dioxaspiro[4.5]dec-8-yl)azetidine

A solution of the just prepared nitrile (2.20 g, 9.9 mmole) in anhydrous tetrahydrofuran (12 ml, 24 mmole) was added dropwise under argon and while cooling with ice to a 2M solution of phenylmagnesium chloride in tetrahydrofuran (12 ml, 24 mmole) and was then stirred overnight at room temperature. After addition of saturated ammonium chloride solution (5 ml) and water (5 ml) the phases were separated and the aqueous phase was extracted with diethyl ether (3×50 ml). The combined organic phases were dried over sodium sulfate and concentrated by evaporation in vacuo. The crude product was purified by flash chromatography (100 g, 20×4.0 cm) with ethyl acetate/cyclohexane (1:1).

Yield: 670 mg (25%), colourless oil
$^1$H-NMR (DMSO-d$_6$): 1.27-1.40 (m, 2H); 1.55-2.00 (m, 8H); 2.86 (t, 4H, J=6.8 Hz); 3.76-3.89 (m, 4H); 7.24-7.45 (m, 5H).

4-azetidin-1-yl-4-phenylcyclohexanone (Ket-15)

6 N hydrochloric acid (2 ml) was added to a solution of the just prepared acetal (370 mg, 1.3 mmole) in acetone (30 ml) and stirred overnight at room temperature. The solution was adjusted to pH 10 by addition of 5N sodium hydroxide solution and the aqueous phase was extracted with dichloromethane (3×20 ml). The combined organic phases were dried over sodium sulfate and concentrated by evaporation in vacuo.

Yield: 274 mg (92%), white solid (Ket-15)
Melting point: not determinable
$^1$H-NMR (DMSO-d$_6$): 1.67 (td, 2H, J=13.8, 6.9 Hz); 1.95-2.13 (m, 4H); 2.20-2.33 (m, 2H); 2.40-2.47 (m, 1H); 2.52-2.57 (m, 1H); 2.94 (t, 4H; J=6.9 Hz); 7.28-7.47 (m, 5H).

Structural Unit Ket-16

1-(8-pyrrolidin-1-yl-1,4-dioxaspiro[4.5]dec-8-yl)-1H-[1,2,3]triazole

Pyrrolidine (1.95 g, 2.29 ml, 27.5 mmole), 1,2,3-triazole (2.07 g, 30 mmole) and molecular sieve 4 Å (7.14 g) were added to a solution of 1,4-dioxaspiro[4.5]decan-8-one (3.9 g, 25 mmole) in toluene (40 ml). The mixture was stirred for 7 days at 90° C. The solution was then decanted and immediately reacted further.

1-(8-butyl-1,4-dioxaspiro[4.5]dec-8-yl)pyrrolidine

The reaction solution of the just prepared triazole derivative (ca. 6.9 g, 25 mmole) in toluene (38 ml) was added dropwise under argon and while cooling with ice to a 2 M solution of n-butylmagnesium chloride (25 ml, 50 mmole) in tetrahydrofuran. The reaction mixture was stirred overnight at room temperature and then poured into saturated ammonium chloride solution (60 ml). The phases were separated and the aqueous phase was extracted with diethyl ether (3×70 ml). The combined organic phases were dried with sodium sulfate, concentrated by evaporation in vacuo and the residue (12 g) was purified by flash chromatography (400 g, 20×7.6 cm) with ethyl acetate/methanol (9:1).

Yield: 2.70 g (40% over two stages), brown oil
$^1$H-NMR (DMSO-d$_6$): 0.87 (t, 3H, J=7.1 Hz); 1.12-1.29 (m, 4H); 1.30-1.45 (m, 4H); 1.46-1.60 (m, 4H); 1.61-1.75 (m, 6H); 1.93 (t, 1H, J=7.1 Hz); 2.36 (t, 1H, J=7.0 Hz), 2.58 (br s, 2H), 3.83 (s, 4H).

4-butyl-4-pyrrolidin-1-yl-cyclohexanone (Ket-16)

Water (10.0 ml) and 37% hydrochloric acid (14.0 ml) were added to a solution of the just obtained acetal (2.70 g, 10.1 mmole) in acetone (100 ml) and the mixture was stirred overnight at room temperature. 4 M sodium hydroxide solution was then slowly added dropwise to the mixture until the pH was 10. The mixture was extracted with diethyl ether (4×40 ml) and the combined organic phases were dried with sodium sulfate and concentrated by evaporation in vacuo. The crude product (2.6 g) was purified by flash chromatography (260 g, 30×5.6 cm) with ethyl acetate/methanol (9:1).

Yield: 1.06 g (47%), brown oil (Ket-16)
$^1$H-NMR (DMSO-d$_6$): 0.88 (t, 3H, J=6.7 Hz); 1.14-1.34 (m, 4H); 1.40-1.50 (m, 2H); 1.62-1.88 (m, 8H); 2.04 (dt, 2H, J=15.0, 3.9 Hz); 2.42 (ddd, 2H, J=6.3, 11.8, 15.5 Hz); 2.63 (t, 4H, J=6.0 Hz).

Structural Unit Ket-17

Methyl-[8-(2-methyl-2H-[1,2,4]triazol-3-yl)-1,4-dioxa-spiro[4.5]dec-8-yl]-amine

Butyllithium (2.5 M in hexane, 9.2 ml, 23.0 mmole) was added to a reaction vessel under an argon atmosphere and cooled to −78° C. 1-methyl-1,2,4-triazole (1.30 ml, 23 mmole) was dissolved in absolute tetrahydrofuran (60.0 ml) and added dropwise at −78° C. while cooling with ice. The reaction mixture was then stirred for 10 minutes at this temperature. 8-methylamino-1,4-dioxa-spiro[4.5]decane-8-carbonitrile (2.12 g, 10.8 mmole) in absolute tetrahydrofuran (15 ml) in a cooling bath maintained at −78° C. was then quickly added dropwise to the formed solution. After the addition the reaction solution was stirred for 1 hour in the cooling bath and was then slowly heated to 0° C. The reaction mixture was stirred overnight at room temperature. The mixture was then hydrolysed at 0° C. with water (10 ml), the aqueous phase was extracted with chloroform (3×50 ml), and the organic phase was washed with water (50 ml) and saturated NaCl solution (50 ml), dried over Na$_2$SO$_4$ and concentrated by evaporation in vacuo. The product was purified by means of flash chromatography with chloroform/methanol (15:1).

Yield: 1.93 g (71%)
$^1$H-NMR (DMSO-d$_6$): 1.54 (2H, m); 1.72 (2H, m); 1.91 (5H, m); 2.10 (2H, m); 3.84 (4H, m); 4.01 (3H, s); 7.74 (1H, s).

4-methylamino-4-(2-methyl-2H-[1,2,4]triazol-3-yl)-cyclohexanone (Ket-17)

5% hydrochloric acid (330 ml) was added at room temperature to methyl-[8-(2-methyl-2H-[1,2,4]triazol-3-yl)-1,4-dioxaspiro[4.5]dec-8-yl]-amine (4.2 g, 16.646 mmole) and the mixture was stirred for 3 days at room temperature. Ether (120 ml) was added to the reaction mixture. The phases were separated. The aqueous phase was made alkaline with 5N NaOH and extracted with dichloromethane (4×50 ml). The organic phase was dried over sodium sulfate and concentrated by evaporation to dryness in vacuo. The product was obtained as a colourless crystalline solid in a yield of 83% (2.89 g, 13.862 mmole).

Indole Structural Units

Structural Unit Synthesis:
The syntheses of the iodopyridinamines are known in the literature and can be implemented by orthometallation of the corresponding pivaloyl-protected aminopyridines in a three-stage sequence: J. A. Turner, *J. Org. Chem.* 1983, 48, 3401; L. Estel, F. Marsais, G. Quéguiner, *J. Org. Chem.* 1988, 53, 2740; J. Malm, B. Rehn, A.-B. Hörnfeldt, S. Gronowitz, *J. Het. Chem.* 1994, 31, 11.

The synthesis of 4-(triethylsilyl)but-3-in-1-ol is described in the literature and has been carried out in a similar manner to the following procedures: B. C. Bishop, I. F. Cottrell, D. Hands *Synthesis*, 1997, 1315; C. Cheng, D. R. Lieberman, R. D. Larsen, R. A. Reamer, T. R. Verhoeven, P. J. Reider *Tet. Lett.*, 1994, 6981.

The azatryptophols were prepared by palladium-mediated Larock heteroannelation; the triethylsilyl-protected precursors are known in the literature: F. Ujjainwalla, D. Warner *Tet. Lett.*, 1998, 5355.

General Structural Units

Triethyl(4-(triethylsilyl)but-3-inyloxy)silane 3-butin-1-ol (34.99 g, 0.50 mole) was dissolved in THF (1.2 l) under nitrogen and cooled to −30° C. n-BuLi (640 ml, 1.02 mole, 1.6 M solution in n-hexane) was added dropwise to this solution within 15 minutes at such a rate that the temperature did not exceed −20° C. After 1 hour at −20° C. a solution of triethylchlorosilane (171.4 ml, 1.02 mole) in THF (300 ml) was added dropwise within 30 minutes. The cooling bath was removed and the reaction solution was stirred for 15 hours at RT. The reaction mixture was quenched with aqueous Na$_2$CO$_3$ solution (1%) while cooling in an ice bath and was extracted with hexane (2×500 ml). The combined organic phases were washed with saturated NaCl-Solution (300 ml) and dried over MgSO$_4$. After filtering off the drying agent the solvents were removed on a rotary evaporator and the residue was purified by distillation (p=0.05 mbar, head temperature=115°-110° C.), triethyl(4-(triethylsilyl)but-3-inyloxy) silane (88.9 g, 60%) being obtained.

4-(triethylsilyl)but-3-in-1-ol

Triethyl(4-(triethylsilyl)but-3-inyloxy)silane (32.99 g, 110.66 mmole) was dissolved in MeOH (336 ml), 2N HCl (62 ml) was added, and the mixture was stirred for 4 hours at RT. Hexane (250 ml) and H$_2$O (200 ml) were then added to the solution and the aqueous phase was extracted with hexane (3×100 ml). The combined organic phases were washed with H$_2$O (100 ml) and then with saturated NaCl-Solution (50 ml) and dried over MgSO$_4$. After filtering off the drying agent the solvents were removed on a rotary evaporator. Column chromatography of the residue (hexane/ether=4:1, then ether) yielded 4-(triethylsilyl)but-3-in-1-ol (19.6 g, 96%) as a colourless oil.

Structural Unit Ind-1

N-(pyridin-2-yl)pivalamide

2-Aminopyridine (25.00 g, 265.6 mmole) was taken up under nitrogen in DCM (425 ml) and NEt$_3$ (46.00 ml, 332 mmole) was added. The solution was cooled to −5° C., a solution of trimethyl acetyl chloride (35.95 ml, 292.20 mmole) in DCM (50 ml) was added dropwise and the mixture was stirred for a further 15 minutes at −5° C. The mixture was then stirred for 2 hours at RT. The suspension was washed with H$_2$O (200 ml), then with dilute NaHCO$_3$ solution, and the organic phase was dried over MgSO$_4$. After filtering off the drying agent and removing the solvent on a rotary evaporator, the residue (48.30 g) was recrystallised from hexane (100 ml) at boiling heat. N-(pyridin-2-yl)pivalamide (42.80 g, 91%) was obtained in the form of colourless crystals.

N-(3-iodopyridin-2-yl)pivalamide

N-(pyridin-2-yl)pivalamide (14.25 g, 80 mmole) and TMEDA (29.80 ml, 200 mmole) were dissolved in THF (400 ml) under nitrogen and n-BuLi (125 ml, 200 mmole; 1.6 M solution in n-hexane) was added dropwise at −75° C. The mixture was stirred for 15 minutes at −75° C. and then for 2 hours at −10° C. After renewed cooling to −75° C. a solution of iodine (50.76 g, 200 mmole) in THF (200 ml) was added dropwise and the reaction mixture was stirred for 2 hours. The mixture was heated to 0° C. and quenched with saturated aqueous sodium thiosulfate solution. The aqueous phase was extracted with DCM (2×150 ml) and the combined organic phases were dried over MgSO$_4$. After filtering off the drying agent and removing the solvent on a rotary evaporator, the residue was purified by column chromatography (ether:cyclohexane=3:1) and N-(3-iodopyridin-2-yl)pivalamide (14.80 g, 61%) was thereby obtained.

3-Iodopyridin-2-amine

N-(3-iodopyridin-2-yl)pivalamide (13.80 g, 45.36 mmole) was taken up in H$_2$SO$_4$ (24 wt. %, 394 ml) and the mixture was stirred for 60 minutes under reflux. After cooling to RT the mixture was neutralised with 4 N NaOH and solid NaHCO$_3$, the aqueous phase was extracted with DCM (3×200 ml), and the combined organic phases were dried over MgSO$_4$. After filtration, the solvent was removed on a rotary evaporator. 3-iodpyridin-2-amine (9.70 g, 97%) was obtained as a cream-coloured solid.

2-(2-(triethylsilyl)-1H-pyrrolo[2,3-b]pyridin-3-yl)ethanol

A mixture of 3-iodopyridin-2-amine (0.46 g, 2.09 mmole), 4-(triethylsilyl)but-3-in-1-ol (0.58 g, 3.14 mmole), 1,1'-bis(diphenylphosphino)ferrocene-palladium(II)dichloride dichloromethane (0.083 g, 0.105 mmole), lithium chloride (0.086 g, 2.09 mmole) and sodium carbonate (0.44 g, 4.18 mmole) in DMF (21 ml) was stirred under nitrogen for 15 hours at 100° C. The reaction mixture was cooled to RT, EtOAc/ether (1:1) was added and the mixture was poured into $H_2O$. The two-phase suspension was filtered through filter earth. After separating the phases the aqueous phase was extracted with EtOAc (2×). The organic phases were combined and washed with $H_2O$ and with saturated NaCl solution and dried over $MgSO_4$. After filtering off the drying agent the solvents were removed on a rotary evaporator. Column chromatography of the residue (n-hexane/EtOAc=2:1, then n-hexane/EtOAc=1:1) yielded 2-(2-(triethylsilyl)-1H-pyrrolo[2,3-b]pyridin-3-yl)ethanol (0.46 g, 80%).

2-(1H-pyrrolo[2,3-b]pyridin-3-yl)ethanol (Ind-1)

2-(2-(triethylsilyl)-1H-pyrrolo[2,3-b]pyridin-3-yl)ethanol (1.00 g, 3.62 mmole) was stirred with TBAF (10.86 ml, 10.86 mmole; 1M solution in THF) for 6 hours at 50° C. and then for 10 hours at RT. The solvent was removed on a rotary evaporator and the residue was purified by column chromatography (DCM/MeOH=9:1, then 1:1). 2-(1H-pyrrolo[2,3-b]pyridin-3-yl)ethanol (0.46 g, 79%) was formed as a white solid.

Structural unit Ind-2

2-(1H-pyrrolo[2,3-c]pyridin-3-yl)ethanol (Ind-2)

2-(2-(triethylsilyl)-1H-pyrrolo[2,3-c]pyridin-3-yl)ethanol (1.99 g, 7.24 mmole) was dissolved in THF (17 ml) and TBAF (7.96 ml, 7.96 mmole; 1 M solution in THF) was added at 0° C. The mixture was stirred for 1 hour at 0° C. and then heated to RT. Further TBAF (7.96 ml, 7.96 mmole, 1 M solution in THF) and $H_2O$ (5 drops) were added. After 2 days at RT 20 ml of $H_2O$ were added and the aqueous phase was extracted with DCM (3×60 ml). The organic phases were combined and washed with saturated NaCl solution (2×20 ml) and dried over $MgSO_4$. After filtering off the drying agent the solvents were removed on a rotary evaporator and the residue was purified by column chromatography (DCM/MeOH=4:1). 2-(1H-pyrrolo[2,3-c]pyridin-3-yl)ethanol (0.60 g, 51%) was formed as a colourless oil, which solidified over time.

Structural Unit Ind-3

N-(5-(trifluoromethyl)pyridin-2-yl)pivalamide 5-(trifluoromethyl)pyridin-2-amine (15 g, 92.5 mmole) was taken up in DCM (190 ml) under nitrogen and $NEt_3$ (16 ml, 115.7 mmole) was added. The solution was cooled to −5° C., a solution of trimethyl acetyl chloride (12.5 ml, 101.8 mmole) in DCM (65 ml) was added dropwise, and the mixture was stirred for a further 15 minutes in an ice bath. The mixture was then stirred for 2 hours at RT. The suspension was washed with $H_2O$ (150 ml), then with dilute $NaHCO_3$ solution, and the organic phase was dried over $MgSO_4$. After filtering off the drying agent and removing the solvent on a rotary evaporator the residue was crystallised. N-(5-(trifluoromethyl)pyridin-2-yl)pivalamide (20.8 g, 91) was obtained.

N-(3-iodo-5-(trifluoromethyl)pyridin-2-yl)pivalamide

N-(5-(trifluoromethyl)pyridin-2-yl)pivalamide (22 g, 89.4 mmole) and TMEDA (33.3 ml, 223.4 mmole) were dissolved in THF (400 ml) under nitrogen and n-BuLi (139.6 ml, 223.4 mmole; 1.6 M solution in n-hexane) was added dropwise at −75° C. The mixture was stirred for 2 hours at −75° C. While maintaining this temperature a solution of iodine (56.7 g, 223.4 mmole) in THF (280 ml) was added dropwise and the reaction mixture was stirred for 2 hours. The reaction mixture was heated to 0° C. and quenched with saturated aqueous sodium thiosulfate solution. The aqueous phase was extracted with DCM (2×150 ml) and the combined organic phases were dried over $MgSO_4$. After filtering off the drying agent and removing the solvent on a rotary evaporator the residue was purified by means of column chromatography (ether: cyclohexane=1:1) and N-(3-iodo-5-(trifluoromethyl)pyridin-2-yl)pivalamide (13 g, 39.1%) was thereby obtained.

3-iodo-5-(trifluoromethyl)pyridin-2-amine

N-(3-iodo-5-(trifluoromethyl)pyridin-2-yl)pivalamide (16.8 g, 45.1 mmole) was taken up in $H_2SO_4$ (24 wt. %, 392 ml) and the mixture was stirred for 60 minutes under reflux. After cooling to RT the mixture was neutralised with 4 N NaOH and solid $NaHCO_3$, the aqueous phase was extracted with DCM (3×200 ml) and the combined organic phases were dried over $MgSO_4$. After filtration the solvent was removed on a rotary evaporator. 3-iodo-5-(trifluoromethyl)pyridin-2-amine (13 g, 100%) was obtained as a cream-coloured solid.

2-(2-(triethylsilyl)-5-(trifluoromethyl)-1H-pyrrolo[2,3-b]pyridin-3-yl)ethanol

A mixture of 3-iodo-5-(trifluoromethyl)pyridin-2-amine (13 g, 45.1 mmole), 4-(triethylsilyl)but-3-in-1-ol (12.4 g, 67.7 mmole), 1,1′-bis(diphenylphosphino)ferrocene-palladium(II) dichloride dichloromethane (1.78 g, 2.26 mmole), lithium chloride (1.86 g, 45.1 mmole) and sodium carbonate (9.54 g, 90.3 mmole) in DMF (460 ml) was stirred under nitrogen for 15 hours at 100° C. The reaction mixture was cooled to RT, 2 l of EtOAc/ether (1:1) were added, and the mixture was poured into 2 l of $H_2O$. The two-phase suspension was filtered through filter earth. After separating the phases the aqueous phase was extracted with EtOAc (2×1 l). The organic phases were combined and washed with $H_2O$ and with saturated NaCl solution and dried over MgSO4. After filtering the drying agent the solvents were removed on a rotary evaporator. The residue was purified by column chromatography (tert.-butyl methyl ether/n-hexane=2:3). The mixed fraction thereby obtained was taken up 4 times, each time with 20 ml of dichloromethane and suction filtered from the white crystalline solid. The first three fractionated precipitates were combined: 2-(2-(triethylsilyl)-5-(trifluoromethyl)-1H-pyrrolo[2,3-b]pyridin-3-yl)ethanol was obtained (3.8 g, 24.4%).

2-(5-(trifluoromethyl)-1H-pyrrolo[2,3-b]pyridin-3-yl)ethanol (Ind-3)

2-(2-(triethylsilyl)-5-(trifluoromethyl)-1H-pyrrolo[2,3-b]pyridin-3-yl)ethanol (3.8 g, 11.0 mmole) was stirred with TBAF (33.1 ml, 33.1 mmole; 1M solution in THF) for 6 hours at 50° C. and then for 10 hours at RT. The solvent was removed on a rotary evaporator. 2-(5-(trifluoromethyl)-1H-pyrrolo[2,3-b]pyridin-3-yl)ethanol (2.4 g, 94.5%) was obtained.

Structural Unit Ind-4

S-2-(1H-Pyrrolo[2,3-b]pyridin-3-yl)ethyl Ethanethioate

Triphenylphosphine (3.56 g, 13.57 mmole) was dissolved in absolute THF (20 ml) under a protective gas. The clear solution was cooled to −5° C. Diisopropyl azodicarboxylate (2.75 g, 13.6 mmole) dissolved in THF (20 ml) was added dropwise within 15 minutes while stirring. A white precipitate was thereby formed. The suspension was stirred for 30 minutes at −5° C. A mixture of Ind-1 (1100 mg, 6.78 mmole) and thioacetic acid (965 µl, 13.57 mmole), dissolved in THF (20 ml), was then added dropwise within 30 minutes. The reaction was slightly exothermic. The temperature was then held for a further hour at −5° C. On slowly heating to room temperature the suspension changed to a clear solution. After stirring for 18 hours at 23° C. the THF had largely distilled off. The substance mixture thereby obtained (8.5 g, brown oil) was diluted with ethyl acetate (30 ml) and extracted with 1N hydrochloric acid (1×10 ml, 3×5 ml). Saturated sodium hydrogen carbonate solution (25 ml) was carefully added to the combined aqueous phases. The mixture was extracted with dichloromethane (3×10 ml). The combined organic phases were dried over sodium sulfate, filtered, and the solvent was distilled off in vacuo. S-2-(1H-pyrrolo[2,3-b]pyridin-3-yl)ethyl ethanethioate was obtained as an almost white solid (1.12 g, 75%).

2-(1H-pyrrolo[2,3-b]pyridin-3-yl)ethanethiol hydrochloride (Ind-4)

Methanol (20 ml) was cooled to below 0° C. under argon. Acetyl chloride (3 ml, 42 mmole) was then slowly added dropwise. The reaction was exothermic. The temperature was maintained below 15° C. during the dropwise addition. The reaction mixture was stirred for 1 hour at room temperature. S-2-(1H-pyrrolo[2,3-b]pyridin-3-yl)ethyl ethanethioate (600 mg, 2.724 mmole) was dissolved in methanol/dichloromethane 1:1 (10 ml) and then added dropwise within 10 minutes. The reaction mixture was stirred for 18 hours at 23° C. The solvent was distilled off. The orange residue was suspended in cyclohexane (5 ml), filtered and washed with cyclohexane (3×1 ml). The beige-coloured Ind-4 was presumably obtained as hydrochloride (578 mg, 99%, melting point 138-150° C.).

Structural unit Ind-5

S-2-(1H-pyrrolo[3,2-c]pyridin-3-yl)ethyl Ethanethioate

Triphenylphosphine (3.83 g, 14.6 mmole) was dissolved in absolute THF (20 ml) under a protective gas. The clear solution was cooled to −5° C. Diisopropyl azodicarboxylate (2.18 g, 10.78 mmole) dissolved in THF (20 ml) was added dropwise within 15 minutes while stirring. A white precipitate was thereby formed. The suspension was stirred for 30 minutes at −5° C.

A mixture of Ind-2 (1700 mg, 5.38 mmole, purity ca. 51% (g/g)) and thioacetic acid (765 µl, 10.75 mmole), dissolved in THF (20 ml), was then added dropwise within 30 minutes. The reaction was slightly exothermic. The temperature was then held for a further hour at −5° C. On slowly heating to room temperature the suspension changed to a clear solution. After stirring for 65 hours at 23° C. the THF had largely distilled off. The substance mixture thereby obtained (7.3 g, brown oil) was diluted with ethyl acetate (30 ml) and extracted with 1N hydrochloric acid (1×10 ml, 3×5 ml). Saturated sodium hydrogen carbonate solution (60 ml) was carefully added to the combined aqueous phases. The mixture was extracted with dichloromethane (3×10 ml). The combined organic phases were dried over sodium sulfate. After filtration, the solvent was distilled off in vacuo. S-2-(1H-pyrrolo[3,2-c]pyridin-3-yl)ethyl ethanethioate was obtained as a brown oil (1.05 g, 82%).

2-(1H-pyrrolo[3,2-c]pyridin-3-yl)ethanethiol Hydrochloride (Ind-5)

Methanol (30 ml) was cooled to below 0° C. under argon. Acetyl chloride (3 ml, 42 mmole) was then slowly added dropwise. The reaction was exothermic. The temperature was maintained below 15° C. during the dropwise addition. The reaction mixture was stirred for 1 hour at room temperature. S-2-(1H-pyrrolo[3,2-c]pyridin-3-yl)ethyl ethanethioate (1.05 g, 4.77 mmole) was dissolved in methanol (10 ml) and then added dropwise within 10 minutes. The reaction mixture was stirred for 18 hours at 23° C. The solvent was distilled off. The orange residue was suspended in diethyl ether (10 ml), filtered, and washed with diethyl ether (3×1 ml). The beige-coloured Ind-5 was presumably obtained as hydrochloride (975 mg, 95%, melting point 182°-195° C.).

Examples

Example 1

4-(dimethylamino)-4-phenyl-spiro[cyclohexane-1,8'-(5,6,8,9-tetrahydropyrano[3,4-b]-7-azaindole)], 1 Diastereomer Ketone Ket-1 (0.13 g, 0.62 mmole) was added together with Ind-1 (0.10 g, 0.62 mmole) to dichloromethane (4 ml, extra-dry). The microwave vessel was closed with a septum and flushed with nitrogen. Trimethylsilyl trifluoromethanesulfonate (0.47 ml, 2.47 mmole) was then quickly added. The mixture was heated for 2×20 minutes at 120° C. in the microwave vessel. 2N NaOH was then added to the reaction mixture and the whole was stirred for 20 minutes. The organic phase was separated and the aqueous phase was extracted with dichloromethane (3×). The combined organic extracts were washed with water and dried over $MgSO_4$. After filtering the drying agent the solvent was removed on a rotary evaporator. Methanol (7 ml) was added to the solid obtained (0.71 g) and the mixture was stirred for 2 hours at room temperature. The solid was suction filtered, washed with a small amount of methanol, and dried.

Yield (Ex. 1): 0.17 g (78%), cream-coloured solid.

$^1$H NMR (600 MHz, $D_6$-DMSO) δ ppm: 1.65-2.8 (m, 16H), 3.17 (s, 1H), 3.96 (m, 2H), 6.93-6.8 (m, 1H), 7.40-7.70 (bm, 4H), 7.76 (d, 1H), 8.06 (d, 1H), 11.40 (s, 1H)

Example 2

4-(dimethylamino)-4-phenyl-spiro[cyclohexane-1,8'-(5,6,8,9-tetrahydropyrano[3,4-b]-7-azaindole)]; Methanesulfonate, Diastereomer Mixture Ketone Ket-1 (0.13 g, 0.62 mmole) was added together with Ind-1 (0.10 g, 0.62 mmole) to dichloromethane (4 ml, extra-dry). The microwave vessel was closed with a septum and flushed with nitrogen. Trimethylsilyl trifluoromethanesulfonate (0.26 ml, 1.36 mmole) was then quickly added. The mixture was heated for 2×10 minutes at 90° C. in the microwave vessel. Further trimethylsilyl trifluoromethanesulfonate (0.26 ml, 1.36 mmole) was then added and the mixture was heated for 1×10 min, then 1×20 min at 120° C. in the microwave vessel. Finally 2N NaOH was added to the reaction mixture, which was stirred for 20 minutes. The organic phase was separated and the aqueous phase was extracted with dichloromethane (3×). The combined organic extracts were washed with water and dried over MgSO$_4$. After filtering the drying agent the solvent was removed on a rotary evaporator. Methanol (7 ml) was added to the solid obtained and the mixture was stirred for 2 hours at room temperature. The solid was suction filtered, washed with a small amount of methanol, and dried (0.14 g, 63%). To precipitate the methanesulfonate the solid (0.14 g, 0.39 mmole) was made into a paste in dichloromethane (2 ml) and methanesulfonic acid (0.028 ml) was added. After 1 minute acetone (0.5 ml) was added to the now clear solution, followed by the dropwise addition of ether until a stirrable mixture was formed. The mixture was then stirred for 30 minutes at room temperature. The precipitate was next suction filtered under exclusion of air, washed with portions of ether, and dried at 50° C. under a high vacuum.

Yield (Ex. 2): 0.16 g (90%), diastereomer mixture (ca. 6:1).

Example 3

4-(dimethylamino)-4-phenyl-spiro[cyclohexane-1,6'-(5,6,8,9-tetrahydropyrano[3,4-b]-5-azaindole)], Diastereomer Mixture Ketone Ket-1 (0.13 g, 0.62 mmole) was added together with Ind-2 (0.10 g, 0.62 mmole) to dichloromethane (4 ml, extra-dry). The microwave vessel was closed with a septum and flushed with nitrogen. Trimethylsilyl trifluoromethanesulfonate (0.47 ml, 2.47 mmole) was then quickly added. The mixture was heated for 40 minutes at 120° C. in the microwave vessel. 2N NaOH was then added to the reaction mixture and the whole was stirred for 20 minutes. The organic phase was separated and the aqueous phase was extracted with dichloromethane (3×). The combined organic extracts were washed with water and dried over MgSO$_4$. After filtering the drying agent the solvent was removed on a rotary evaporator. Methanol (7 ml) was added to the solid obtained and the mixture was stirred for 48 hours at room temperature. The solid was suction filtered, washed with a small amount of methanol, and dried.

Yield (Ex. 3): 0.06 g (28%), cream-coloured solid (diastereomer mixture: ca. 5:1).

$^1$H NMR (600 MHz, D$_6$-DMSO) δ ppm: diastereomer 1:1.63 (t, 2H), 2.13 (bd, 2H), 2.16 (t, 2H), 2.27 (s, 6H) 2.11 (bd, 2H), 2.77 (m, 2H), 3.98 (m, 2H), 7.26 (d, 1H), 7.37 (d, 1H), 7.5 (m, 1H) 7.56 (t, 2H), 7.63 (m. 2H), 8.12 (d, 1H), 8.76 (s, 1H) 11.33 (bs, 1H), additional peaks diastereomer 2: 1.74-1.80 (bt, 4H), 2.06 (s, 6H), 3.91 (m, 2H), 7.43-7.48 (m, 1H), 8.19 (d, 1H), 8.84 (s, 1H), 11.8 (bs, 1H)

Example 4

4-(dimethylamino)-4-thiophen-2-yl-spiro[cyclohexane-1,8'-(5,6,8,9-tetrahydropyrano[3,4-b]-7-azaindole)]; Methanesulfonate, 1 Diastereomer Ketone Ket-2 (0.13 g, 0.62 mmole) and 2-(1H-pyrrolo[2,3-b]pyridin-3-yl)ethanol Ind-1 (0.10 g, 0.62 mmole) were added under nitrogen to dichloromethane (4 ml, ultra-dry). Trimethylsilyl trifluoromethanesulfonate (0.48 ml, 2.47 mmole) was then quickly added. The mixture was stirred for 5 days at room temperature. After addition of tetrahydrofuran the mixture was adjusted alkaline (pH=11) with 1M aqueous Na$_2$CO$_3$ solution and stirred for 20 minutes at room temperature. The organic phase was separated and the aqueous phase was extracted with tetrahydrofuran (2×). The combined organic phases were washed with saturated NaCl solution and dried over MgSO$_4$. After filtering the drying agent the solvents were removed on a rotary evaporator. Methanol (3 ml) was added to the solid obtained and the mixture was stirred for 18 hours at room temperature. The solid was suction filtered, washed with a small amount of methanol, and dried at 50° C. under an oil pump vacuum (0.09 g, 43%). To precipitate the methanesulfonate the solid (0.07 g, 0.19 mmole) was made into a paste with dichloromethane (2 ml), and methanesulfonic acid (0.014 ml) was added at room temperature. After 5 minutes ether (10 ml) was added to the suspension. After stirring for 30 minutes at room temperature the solid was suction filtered under exclusion of air, washed with ether, and dried at 50° C. in an oil pump vacuum.

Yield (Ex. 4): 0.07 g (79%)

$^1$H NMR (600 MHz, D$_6$-DMSO) δ ppm: 1.87-1.98 (m, 4H), 2.26-2.35 (m, 5H), 2.59-2.65 (m, 8H), 2.71 (t, 2H), 3.97 (t, 2H), 6.98-7.04 (m, 1H), 7.32 (t, 1H), 7.55 (d, 1H), 7.83 (d, 1H), 7.92 (d, 1H), 8.11 (d, 1H), 9.55 (bs, 1H), 11.60 (s, 1H)

Example 5

4-(dimethylamino)-4-thiophen-2-yl-spiro[cyclohexane-1,6'-(5,6,8,9-tetrahydropyrano[3,4-b]-5-azaindole)], 1 Diastereomer Ketone Ket-2 (0.13 g, 0.62 mmole) and Ind-2 (0.10 g, 0.62 mmole) were added under nitrogen to dichloromethane (4 ml, ultra-dry). Trimethylsilyl trifluoromethanesulfonate (0.48 ml, 2.47 mmole) was then quickly added. The mixture was stirred for 6 days at room temperature. After addition of tetrahydrofuran the mixture was made alkaline (pH=11) with 1M aqueous Na$_2$CO$_3$ solution and stirred for 20 minutes at room temperature. The organic phase was separated and the aqueous phase was extracted with ethyl acetate (2×). The combined organic phases were washed with saturated NaCl solution and dried over MgSO$_4$. After filtering the drying agent the solvents were removed on a rotary evaporator.

Column chromatography purification of the residue (dichloromethane:methanol=19:1) yielded Example 5 (0.05 g, 22%).

$^1$H NMR (600 MHz, D$_6$-DMSO) δ ppm: 1.84 (bt, 2H), 2.01 (bd, 2H), 2.29 (bt, 2H), 2.5 (s, 6H superimposed with DMSO), 2.60 (bd, 2H), 2.85 (t, 2H), 4.01 (t, 2H), 7.30-7.34 (m, 1H), 7.48-7.53 (m, 1H), 7.63 (d, 1H), 7.86-7.91 (m, 1H), 8.29 (d, 1H), 9.09 (s, 1H), 12.37 (bs, 1H)

Example 6

4-(dimethylamino)-4-phenyl-spiro[cyclohexane-1,8'-(5,6,8,9-tetrahydropyrano[3,4-b]-7-azaindole)]; Citrate (4:3), 1 Diastereomer Ket-1 (0.27 g, 1.23 mmole) was added together with Ind-1 (0.20 g, 1.23 mmole) to dichloromethane (4 ml, ultra-dry). The microwave vessel was closed with a septum and flushed with nitrogen. Trimethylsilyl trifluoromethanesulfonate (1.1 ml, 4.9 mmole) was then quickly added. The mixture was heated for 40 minutes at 120° C. in a microwave vessel. Finally, 1M Na$_2$CO$_3$ solution (pH=11) was added to the reaction mixture and the whole was stirred for 20 minutes. The organic phase was separated and the aqueous phase was extracted with dichloromethane (3×). The combined organic extracts were washed with water and dried over MgSO$_4$. After filtering the drying agent the solvent was removed in a rotary evaporator. Methanol (7 ml) was added to the solid obtained and the mixture was stirred for 2 hours at room temperature. The solid was suction filtered, washed with a small amount of methanol, and dried (0.257 g, 57%). In order to precipitate the citrate the solid (0.1 g, 0.27 mmole) was made into a paste in hot ethanol (6 ml) and a hot solution of citric acid (0.053 g) in ethanol (1.4 ml) was also added. The solution was stirred for 3 days at room temperature. The precipitate was then suction filtered, washed with portions of ether, and dried under a high vacuum at 60° C.

Yield (Ex. 6): 0.109 g (71%).

$^1$H NMR (600 MHz, D$_6$-DMSO) δ ppm: 1.68-1.89 (m, 4H), 2.1-2.3 (m, 8H), 2.50-2.58 (q, 3H), 2.68 (m, 4H), 3.96 (m, 2H), 6.93-6.99 (m, 1H), 7.43-7.64 (m, 5H), 7.75 (d, 1H), 8.06 (d, 1H), 11.40 (s, 1H)

Example 7

4-(methylamino)-4-phenyl-spiro[cyclohexane-1,8'-(5,6,8,9-tetrahydropyrano[3,4-b]-7-azaindole)]; Citrate (1:1), 1 Diastereomer Ketone Ket-3 (0.125 g, 0.62 mmole) was added together with Ind-1 (0.10 g, 0.62 mmole) to dichloromethane (4 ml, ultra-dry). The microwave vessel was closed with a septum and flushed with nitrogen. Trimethylsilyl trifluoromethanesulfonate (0.48 ml, 2.5 mmole) was then quickly added. The mixture was heated for 30 minutes at 120° C. in the microwave vessel. Finally 2N NaOH solution was added to the reaction mixture and the whole was stirred for 20 minutes. The organic phase was separated and the aqueous phase was extracted with dichloromethane (3×). The combined organic extracts were washed with water and dried over MgSO$_4$. After filtering the drying agent the solvent was removed on a rotary evaporator. Column chromatography purification of the residue (dichloromethane:methanol=4:1) yielded 4-(methylamino)-4-phenyl-spiro[cyclohexane-1,8'-(5,6,8,9-tetrahydropyrano[3,4-b]-7-azaindole)] (0.06 g, 28%). To precipitate the citrate, 4-(methylamino)-4-phenyl-spiro[cyclohexane-1,8'-(5,6,8,9-tetrahydropyrano[3,4-b]-7-azaindole)] (0.053 g, 0.15 mmole) was made into a paste in hot ethanol (4 ml) and a hot solution of citric acid (0.032 g) in ethanol (1 ml) was also added. The solution was stirred for 3 hours at room temperature. The precipitate was then suction filtered, washed with portions of ether, and dried at 60° C. under a high vacuum.

Yield (Ex. 7): 0.07 g (85%).

$^1$H NMR (600 MHz, D$_6$-DMSO) δ ppm: 1.76-1.83 (bt, 2H), 1.87-1.93 (bd, 2H), 2.08 (s, 3H), 2.16-2.25 (bt, 2H), 2.47 (d, 2H), 2.54 (d, 2H), 2.55-2.60 (m, 2H), 2.70 (bt, 2H), 3.98 (bt, 2H), 6.95-6.99 (m, 1H), 7.49 (t, 1H), 7.56 (t, 2H), 7.66 (d, 2H), 7.77 (d, 1H) 8.08 (d, 1H), 11.46 (s, 1H) broad signal at 8.5-12.0

Example 8

4-(methylamino)-4-thiophen-2-yl-spiro[cyclohexane-1,8'-(5,6,8,9-tetrahydropyrano[3,4-b]-7-azaindole)]; Citrate (4:3), 1 Diastereomer Ketone Ket-4 (0.13 g, 0.62 mmole) was added together with Ind-1 (0.10 g, 0.62 mmole) under nitrogen to dichloromethane (4 ml, ultra-dry). Trimethylsilyl trifluoromethanesulfonate (0.48 ml, 2.5 mmole) was then quickly added. The mixture was stirred for 15 days at room temperature. After adding tetrahydrofuran the mixture was made alkaline with 1M Na$_2$CO$_3$ solution and stirred for 20 minutes. The organic phase was separated and the aqueous phase was extracted with tetrahydrofuran (2×). The combined organic extracts were washed with saturated NaCl solution and dried over MgSO$_4$. After filtering the drying agent the solvent was removed on a rotary evaporator. Methanol (5 ml) was added to the solid obtained and the mixture was stirred for 18 hours at room temperature. The solid was suction filtered, washed with a small amount of methanol and dried in an oil pump vacuum (0.118 g, 54%). In order to precipitate the citrate the solid (0.112 g, 0.32 mmole) was made into a paste in hot ethanol (4 ml) and a hot solution of citric acid (0.066 g) in ethanol (1.5 ml) was also added. The solution was stirred for 3 hours at room temperature. The precipitate was then suction filtered, washed with portions of ether and dried at 60° C. in a high vacuum.

Yield (Ex. 8): 0.117 g (68%).

$^1$H NMR (600 MHz, D$_6$-DMSO) δ ppm: 1.86-1.99 (m, 4H), 2.14 (s, 3H) 2.18 (bd, 2H), 2.31 (bd, 2H), 2.47 (d, 1.4H), 2.54 (d, 1.4H), 2.69 (t, 2H), 3.95 (t, 2H), 6.96-6.99 (m, 1H), 7.16 (m, 1H), 7.30 (m, 1H), 7.66 (d, 1H), 7.77 (d, 1H), 8.09 (d, 1H), 11.51 (s, 1H) broad signal at 8.0-12.0

Example 9

4-(dimethylamino)-4-benzo[1,3-dioxol]-spiro[cyclohexane-1,8'-(5,6,8,9-tetrahydropyrano[3,4-b]-7-azaindole)]; Citrate (1:1), 1 Diastereomer

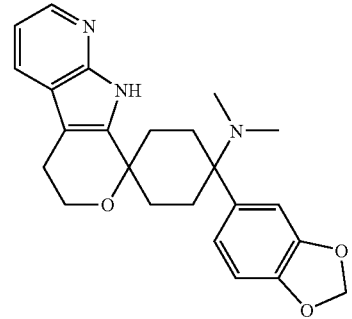 [SMILES: CN(C)C1(c2ccc3c(c2)OCO3)CCC2(CC1)OCCc1c2[nH]c2ncccc12]

Ketone Ket-5 (0.16 g, 0.62 mmole) was added together with Ind-1 (0.10 g, 0.62 mmole) under nitrogen to dichloromethane (4 ml, ultra-dry). Trimethylsilyl trifluoromethanesulfonate (0.48 ml, 2.5 mmole) was then quickly added. The mixture was stirred for 15 days at room temperature. After addition of tetrahydrofuran the mixture was made alkaline with 1M Na$_2$CO$_3$ solution and stirred for 20 minutes. The organic phase was separated and the aqueous phase was extracted with tetrahydrofuran (2×). The combined organic extracts were washed with saturated NaCl solution and dried over MgSO$_4$. After filtering the drying agent the solvent was removed on a rotary evaporator. Methanol (5 ml) was added to the solid obtained and the mixture was stirred for 2 hours at room temperature. The solid was suction filtered, washed with a small amount of methanol and dried at 50° C. in an oil pump vacuum (0.052 g, 21%).

In order to precipitate the citrate the solid (0.047 g, 0.11 mmole) was made into a paste in hot ethanol (4 ml) and a hot solution of citric acid (0.024 g) in ethanol (1 ml) was also added. The solution was stirred for 3 hours at room temperature. The precipitate was then suction filtered, washed with portions of ether, and dried at 60° C. in a high vacuum.

Yield (Ex. 9): 0.061 g (88%).

$^1$H NMR (600 MHz, D$_6$-DMSO) δ ppm: 1.7-1.78 (t, 2H), 1.83-1.90 (d, 2H), 2.09-2.17 (m, 2H), 2.32-2.41 (m, 6H) 2.53 (d, 2H), 2.58 (d, 2H), 2.68 (t, 4H), 3.96 (t, 2H), 6.13 (s, 2H), 6.95-6.99 (m, 1H), 7.05-7.10 (m, 1H), 7.10-7.17 (m, 1H), 7.25 (m, 1H), 7.76 (d, 1H), 8.08 (d, 1H), 11.42 (bs, 1H)

Example 10

4-(dimethylamino)-4-(benzothiophen-2-yl)-spiro[cyclohexane-1,8'-(5,6,8,9-tetrahydropyrano[3,4-b]-7-azaindole)]; Citrate (1:1), 1 Diastereomer Ketone Ket-6 (0.17 g, 0.62 mmole) was added together with Ind-1 (0.10 g, 0.62 mmole) under nitrogen to dichloromethane (4 ml, ultra-dry). Trimethylsilyl trifluoromethanesulfonate (0.48 ml, 2.5 mmole) was then quickly added. The mixture was stirred for 7 days at room temperature. After adding tetrahydrofuran the mixture was made alkaline with 1M Na$_2$CO$_3$ solution and stirred for 20 minutes. The organic phase was separated and the aqueous phase was extracted with dichloromethane (3×). The combined organic extracts were washed with saturated NaCl solution and dried over MgSO$_4$. After filtering the drying agent the solvent was removed on a rotary evaporator. Methanol (5 ml) was added to the solid obtained and the mixture was stirred for 2 hours at room temperature. The solid was suction filtered, washed with a small amount of methanol and dried at 50° C. in an oil pump vacuum (0.158 g, 61%). In order to precipitate the citrate the solid (0.154 g, 0.37 mmole) was made into a paste in hot ethanol (4 ml) and a hot solution of citric acid (0.071 g) in ethanol (2.5 ml) was also added. The solution was stirred for 3 hours at room temperature. The precipitate was then suction filtered, washed with portions of ether and dried at 60° C. in a high vacuum.

Yield (Ex. 10): 0.193 g (85%).

$^1$H NMR (600 MHz, D$_6$-DMSO) δ ppm: 1.89-2.03 (m, 4H), 2.19-2.28 (m, 2H), 2.39 (bs, 6H), 2.56-2.62 (m, 3H), 2.65-2.71 (m, 5H); 3.96 (m, 2H), 6.94-6.98 (m, 1H), 7.38-7.46 (m, 2H), 7.63 (bs, 1H), 7.76 (d, 1H), 7.93 (d, 1H), 8.02 (d, 1H), 8.05 (d, 1H), 11.43 (bs, 1H)

Example 12

4-(dimethylamino)-4-(3-fluorophenyl)-spiro[cyclohexane-1,8'-(5,6,8,9-tetrahydropyrano[3,4-b]-7-azaindole)]; Citrate (4:3), 1 Diastereomer Ketone Ket-7 (0.145 g, 0.62 mmole) was added together with Ind-1 (0.10 g, 0.62 mmole) under nitrogen to dichloromethane (4 ml, ultra-dry). Trimethylsilyl trifluoromethanesulfonate (0.48 ml, 2.5 mmole) was then quickly added. The mixture was stirred for 7 days at room temperature. After addition of dichloromethane the mixture was made alkaline with 1M Na$_2$CO$_3$ solution and stirred for 20 minutes. The organic phase was separated and the aqueous phase was extracted with dichloromethane (3×). The combined organic extracts were washed with saturated NaCl solution and dried over MgSO$_4$. After filtering the drying agent the solvent was removed on a rotary evaporator. Methanol (5 ml) was added to the solid obtained and the mixture was stirred for 2 hours at room temperature. The solid was suction filtered, washed with a small amount of methanol and dried at 50° C. in an oil pump vacuum (0.054 g, 23%).

In order to precipitate the citrate the solid (0.054 g, 0.14 mmole) was made into a paste in hot ethanol (3 ml) and a hot solution of citric acid (0.027 g) in ethanol (1 ml) was also added. The solution was stirred for 3 hours at room temperature. The precipitate was then suction filtered, washed with portions of ether and dried at 60° C. in a high vacuum.

Yield (Ex. 12): 0.048 g (59%).

$^1$H NMR (600 MHz, D$_6$-DMSO) δ ppm: 1.69 (bt, 2H), 1.85 (bd, 2H), 2.09 (bt, 2H), 2.20 (bs, 6H), 2.51-2.55 (d, 1.5H), 2.56-2.62 (d, 1.5H), 2.63 (m, 2H) 2.67 (t, 2H), 3.95 (t, 2H), 6.94-6.97 (m, 1H), 7.25-7.31 (m, 1H), 7.35-7.42 (m, 2H), 7.52-7.58 (m, 1H), 7.76 (d, 1H), 8.07 (d, 1H), 11.37 (s, 1H)

Example 13

4-(dimethylamino)-4-(3-methylphenyl)-spiro[cyclohexane-1,8'-(5,6,8,9-tetrahydropyrano[3,4-b]-7-azaindole)]; Citrate (1:1), 1 Diastereomer Ketone Ket-8 (0.142 g, 0.62 mmole) was added together with Ind-1 (0.10 g, 0.62 mmole) under nitrogen to dichloromethane (4 ml, ultra-dry). Trimethylsilyl trifluoromethanesulfonate (0.48 ml, 2.5 mmole) was then quickly added. The mixture was stirred for 7 days at room temperature. After adding dichloromethane the mixture was made alkaline with 1M Na$_2$CO$_3$ solution and stirred for 20 minutes. The organic phase was separated and the aqueous phase was extracted with dichloromethane (3×). The combined organic extracts were washed with saturated NaCl solution and dried over MgSO$_4$. After filtering the drying agent the solvent was removed on a rotary evaporator. Methanol (5 ml) was added to the solid obtained and the mixture was stirred for 2 hours at room temperature. The solid was suction filtered, washed with a small amount of methanol, and dried at 50° C. in an oil pump vacuum (0.117 g, 50%).

In order to precipitate the citrate the solid (0.112 g, 0.30 mmole) was made into a paste in hot ethanol (4 ml) and a hot solution of citric acid (0.057 g) in ethanol (2 ml) was also added. The solution was stirred for 3 hours at room temperature. The precipitate was then suction filtered, washed with portions of ether and dried at 60° C. in a high vacuum.

Yield (Ex. 13): 0.118 g (70%).

$^1$H NMR (600 MHz, D$_6$-DMSO) δ ppm: 1.73 (m, 2H), 2.15 (m, 2H), 2.3 (bs, 6H), 2.43 (s, 3H), 2.56-2.58 (m, 3H), 2.67-2.69 (m, 4H), 3.96 (m, 2H), 6.95-6.97 (m, 1H), 7.32 (bm, 1), 7.42-7.44 (m, 3H), 7.77 (d, 1H), 8.07 (d, 1H), 11.41 (s, 1H).

Example 14

4-(dimethylamino)-4-(but-1-yl)-spiro[cyclohexane-1,8'-(5,6,8,9-tetrahydropyrano[3,4-b]-7-azaindole)], Citrate (1:1), 1 Diastereomer Ketone Ket-9 (0.3 g, 0.185 mmole) was added together with Ind-1 (0.10 g, 0.62 mmole) under nitrogen to dichloromethane (4 ml, ultra-dry). Trimethylsilyl trifluoromethanesulfonate (0.48 ml, 2.5 mmole) was then quickly added. The mixture was stirred for 5 days at room temperature. After adding dichloromethane the mixture was made alkaline with 1M Na$_2$CO$_3$ solution and stirred for 20 minutes. The organic phase was separated and the aqueous phase was extracted with dichloromethane (3×). The combined organic extracts were washed with saturated NaCl solution and dried over MgSO$_4$. After filtering the drying agent the solvent was removed on a rotary evaporator. Column chromatography purification of the residue (dichloromethane methanol=4:1)

yielded 4-(dimethylamino)-4-(but-1-yl)-spiro[cyclohexane-1,8'-(5,6,8,9-tetrahydropyrano[3,4-b]-7-azaindole)] (0.026 g, 12%).

In order to precipitate the citrate the solid (0.02 g, 0.06 mmole) was made into a paste in hot ethanol (2 ml) and a hot solution of citric acid (0.012 g) in ethanol (1 ml) was also added. The solution was stirred for 3 hours at room temperature. The precipitate was then suction filtered, washed with portions of ether and dried at 60° C. in a high vacuum.

Yield (Ex. 14): 0.021 g (67%).

Example 15

4-(dimethylamino)-4-phenylethyl-spiro[cyclohexane-1,8'-(3-trifluoromethyl-5,6,8,9-tetrahydropyrano[3,4-b]-7-azaindole)]; Citrate (1:1), 1 Diastereomer Ketone Ket-10 (0.319 g, 1.30 mmole) was added together with Ind-3 (0.3 g, 1.30 mmole) to dichloromethane (3.4 ml, ultra-dry). The microwave vessel was closed with a septum and flushed with nitrogen. Trimethylsilyl trifluoromethanesulfonate (1.01 ml, 5.2 mmole) was then quickly added. The reaction mixture was heated for 10 minutes at 120° C. in the microwave vessel. 1M aqueous $Na_2CO_3$ solution was then added to the reaction mixture and the whole was stirred for 20 minutes. The organic phase was separated and the aqueous phase was extracted with dichloromethane (3×). The combined organic extracts were washed with water and saturated NaCl solution and dried over $MgSO_4$. After filtering the drying agent the solvent was removed on a rotary evaporator. The foamy solid obtained was purified by means of column chromatography (silica gel KG 60; dichloromethane:methanol 9:1). 4-(dimethylamino)-4-phenylethyl-spiro[cyclohexane-1,8'-(3-trifluoromethyl-5,6,8,9-tetrahydropyrano[3,4-b]-7-azaindole)] (0.14 g, 23.5%) was obtained.

In order to precipitate the citrate the solid (0.140 g, 0.306 mmole) was dissolved in hot ethanol (2 ml) and citric acid (0.058 g) and diethyl ether (10 ml) were added. The solution was stirred at room temperature. The solid was suction filtered and dried at 60° C. in a high vacuum.

Yield (Ex. 15): 0.173 g (87%).

Example 17

4-(dimethylamino)-4-ethyl-spiro[cyclohexane-1,8'-(5,6,8,9-tetrahydropyrano[3,4-b]-7-azaindole)]; Citrate (2:3), Diastereomer Mixture Ket-12 (0.25 g, 1.48 mmole) was added together with Ind-1 (0.24 g, 1.48 mmole) to dichloromethane (3.3 ml). The microwave vessel was closed with a septum and flushed with nitrogen. Trimethylsilyl trifluoromethanesulfonate (1.14 ml, 5.92 mmole) was then quickly added. The reaction mixture was heated for 20 minutes at 120° C. in a microwave vessel. 1M aqueous $Na_2CO_3$ solution was then added to the reaction mixture and the whole was stirred for 20 minutes. The organic phase was separated and the aqueous phase was extracted with dichloromethane (3×). The combined organic extracts were washed with water and saturated NaCl solution and dried over $MgSO_4$. After filtering the drying agent the solvent was removed on a rotary evaporator. Methanol (5 ml) was added to the solid obtained and the mixture was stirred for 2 hours at room temperature. The solid was suction filtered, washed with a small amount of methanol and dried at 50° C. in a high vacuum. A cream-coloured solid (0.07 g, 15.1%) was formed.

The solid (0.07 g, 0.22 mmole) was made into a paste in hot ethanol (2 ml) and a hot solution of citric acid (0.043 g) in ethanol (1 ml) was also added. The solution was stirred for 3 hours at room temperature. The clear solution was concentrated by evaporation to dryness and dried at 60° C. in a high vacuum.

Yield (Ex. 17): 0.083 g (62%).

Example 18

4-(dimethylamino)-4-phenylethyl-spiro[cyclohexane-1,8'-(5,6,8,9-tetrahydropyrano[3,4-b]-7-azaindole)]; Citrate (2:3), 1 Diastereomer Ket-10 (0.227 g, 0.925 mmole) was added together with Ind-1 (0.15 g, 0.925 mmole) to dichloromethane (3.6 ml, ultra-dry). The microwave vessel was closed with a septum and flushed with nitrogen. Trimethylsilyl trifluoromethanesulfonate (0.715 ml, 3.70 mmole) was then quickly added. The reaction mixture was stirred for 10 days at RT. On account of the incomplete conversion the mixture was heated twice, 15 minutes each time, at 120° C. in a microwave vessel. 1M aqueous $Na_2CO_3$ solution was then added to the reaction mixture and the whole was stirred for 20 minutes. The organic phase was separated and the aqueous phase was extracted with dichloromethane (3×). The combined organic extracts were washed with water and dried over $MgSO_4$. After filtering the drying agent the solvent was removed on a rotary evaporator. Methanol (7 ml) was added to the solid obtained and the mixture was stirred for 1 hour at room temperature. The solid was suction filtered, washed with a small amount of methanol and dried. A cream-coloured solid (0.15 g, 41.4%) was obtained.

The solid (0.144 g, 0.37 mmole) was made into a paste in hot ethanol (3 ml) and a hot solution of citric acid (0.071 g) in ethanol (2 ml) was also added. The solution was stirred for 3 hours at room temperature. The precipitate was then suction filtered, washed with a small amount of ethanol and twice with ether, and dried at 60° C. in a high vacuum.

Yield (Ex. 18): 0.184 g (73%).

$^1$H NMR (600 MHz, $D_6$-DMSO) δ ppm: 1.74-1.83 (m, 2H), 1.90-1.96 (m, 2H), 2.02-2.10 (m, 4H), 2.22-2.30 (m, 2H), 2.52-2.58 (d, 3H), 2.58-2.65 (d, 3H), 2.65-2.75 (m, 5H), 2.79 (bs, 5H), 3.94 (t, 2H), 6.99-7.04 (m, 1H), 7.18-7.32 (m, 2H), 7.34-7.43 (m, 3H), 7.82 (d, 1H), 8.14 (d, 1H), 11.70 (s, 1H)

Example 19

4-benzyl-4-morpholino-spiro[cyclohexane-1,8'-(5,6,8,9-tetrahydropyrano[3,4-b]-7-azaindole)]; Citrate (1:1), 1 Diastereomer Ket-13 (0.252 g, 0.925 mmole) was added together with Ind-1 (0.15 g, 0.925 mmole) to dichloromethane (3.6 ml, ultra-dry). The microwave vessel was closed with a septum and flushed with nitrogen. Trimethylsilyl trifluoromethanesulfonate (0.715 ml, 3.70 mmole) was then quickly added. The reaction mixture was stirred for 10 days at RT. 1M aqueous $Na_2CO_3$ solution was then added to the reaction mixture and the whole was stirred for 20 minutes. The organic phase was separated and the aqueous phase was extracted with dichloromethane (3×). The combined organic extracts were washed with water and dried over $MgSO_4$. After filtering the drying agent the solvent was removed on a rotary evaporator. Methanol (7 ml) was added to the solid obtained and the mixture was stirred for 2 hours at room temperature. The solid was suction filtered, washed with a small amount of methanol and dried at 50° C. in a high vacuum (0.248 g, 64.2%, cream-coloured solid).

The solid (0.234 g, 0.56 mmole) was made into a paste in hot ethanol (5 ml) and a hot solution of citric acid (0.108 g) in ethanol (3 ml) was also added. The precipitate was then suction filtered, washed with a small amount of ethanol and twice with ether, and dried at 60° C. in a high vacuum.

Yield (Ex. 19): 0.280 g (82%).

$^1$H NMR (600 MHz, D$_6$-DMSO) δ ppm: 1.35-1.55 (bs, 2H), 1.87 (bm, 4H), 2.20 (m, 2H), 2.62-2.74 (m, 10H), 3.13 (bm, 2H), 3.58 (bm, 4H), 3.92 (m, 2H), 7.00 (m, 1H), 7.17 (m, 1H), 7.32 (m, 1H), 7.46 (d, 1H), 7.80 (d, 1H), 8.16 (d, 1H), 11.66 (s, 1H).

Example 20

4-(dimethylamino)-4-(3-methoxypropyl)-spiro[cyclohexane-1,8'-(5,6,8,9-tetrahydropyrano[3,4-b]-7-azaindole)]; Citrate (1:1), 1 Diastereomer Ket-14 (0.197 g, 0.925 mmole) was added together with Ind-1 (0.15 g, 0.925 mmole) to dichloromethane (3.6 ml, ultra-dry). The microwave vessel was closed with a septum and flushed with nitrogen. Trimethylsilyl trifluoromethanesulfonate (0.715 ml, 3.70 mmole) was then quickly added. The reaction mixture was stirred for 13 days at RT. The reaction mixture was heated twice, each time for 15 minutes, at 120° C. in the microwave vessel. 1M aqueous Na$_2$CO$_3$ solution was then added to the reaction mixture and the whole was stirred for 20 minutes. The organic phase was separated and the aqueous phase was extracted with dichloromethane (3×). The combined organic extracts were washed with water and dried over MgSO$_4$. After filtering the drying agent the solvent was removed on a rotary evaporator. Methanol (7 ml) was added to the solid obtained and the mixture was stirred for 2 hours at room temperature. The oil obtained was purified by column chromatography (silica gel KG 60; dichloromethane:methanol 4:1) (0.1 g, 30.2%, cream-coloured solid). In order to precipitate the citrate the solid (0.095 g, 0.27 mmole) was suspended in hot ethanol (2 ml) and a hot solution of citric acid (0.051 g) in ethanol (2 ml) was also added. The solution was stirred overnight at room temperature. The precipitate was then suction filtered, washed with a small amount of ethanol and twice with ether, and dried at 60° C. in a high vacuum.

Yield (Ex. 20): 0.111 g (76%).

Example 21

4-(dimethylamino)-4-phenyl-spiro[cyclohexane-1,8'-(5,6,8,9-tetrahydropyrano[3,4-b]-7-azaindole)]; Citrate (1:1), 1 Diastereomer The ketone Ket-1 (247 mg, 1.1 mmole) was dissolved together with Ind-1 (184 mg, 1.1 mmole) in dichloromethane (20 ml). Trifluoromethanesulfonic acid (363 mg, 0.215 ml, 2.42 mmole) was then added, following which the reaction mixture turned a dark colour. The mixture was stirred for 20 hours at RT. The reaction mixture was worked up by adding 1N NaOH (8 ml) and stirred for 10 minutes. As a result the colour changed from dark red to pale brown. A colourless solid precipitated out. The solid (126 mg) was suction filtered and washed with dichloromethane (5 ml). The phases of the filtrate were separated. The aqueous phase was extracted with dichloromethane (2×10 ml). The combined organic phases were dried with sodium sulfate, filtered, and concentrated by evaporation in vacuo. A pale brown solid (491 mg) was obtained. Ethyl acetate (10 ml) was added to the crude product, a colourless solid thereupon precipitating out. This was suction filtered (119 mg) and washed with ethyl acetate (10 ml). The two solids were identical and were combined (245 mg, 62%) and had a melting point of 266°-274° C.

The solid (215 mg, 0.59 mmole) was heated to the boil in ethanol (70 ml). Citric acid (274 mg, 1.43 mmole), dissolved in hot ethanol (5 ml), was added to the cloudy solution. The solution then became clear. The colourless precipitate formed after stirring for 20 hours at RT was suction filtered and washed with ethanol (10 ml). Example 21 was thus obtained in a yield of 88% (288 mg)

$^1$H NMR (400 MHz, CD$_3$OD) δ ppm: 1.01 (t, J=7.01 Hz, 1.5H), 1.53-1.78 (m, 2H), 1.78-1.93 (m, 2H), 2.00-2.41 (m, 8H), 2.42-2.61 (m, 5H), 2.61-2.82 (m, 3H), 3.40 (d, J=6.83 Hz, 1H), 3.85-4.02 (m, 2H), 6.87-7.02 (m, 1H), 7.41-7.58 (m, 3H), 7.58-7.69 (m, 2H), 7.73 (d, J=7.74 Hz, 1H), 8.03 (d, J=4.57 Hz, 1H), 11.40 (s, 1H)

$^{13}$C NMR (101 MHz, CD$_3$OD) δ ppm: 18.5, 21.6, 26.2, 31.1, 37.4, 44.0, 56.0, 59.0, 70.8, 71.3, 104.3, 114.9, 118.6, 125.5, 128.6, 128.8, 129.1, 138.7, 141.8, 148.5, 171.1, 176.4

Example 22

4-(dimethylamino)-4-thiophen-2-yl-spiro[cyclohexane-1,8'-(5,6,8,9-tetrahydropyrano[3,4-b]-7-azaindole)]; Citrate (1:1), 1 Diastereomer The ketone Ket-2 (268 mg, 1.2 mmole) was dissolved together with the azatryptophol Ind-1 (195 mg, 1.2 mmole) in 1,2-dichloroethane (20 ml). Trifluoromethanesulfonic acid (397 mg, 0.235 ml, 2.64 mmole) was then added, whereupon the reaction mixture turned a dark lilac colour. The reaction mixture was stirred for a total of 40 hours at RT. To work up the reaction mixture the mixture was adjusted to pH 11 with 1N NaOH (8 ml) and stirred for 15 minutes. The colour thereupon changed to pale brown, and a pale brown solid precipitated out. The solid (140 mg) was suction filtered and washed with methanol (15 ml). As a result the product became colourless. The phases of the filtrate were separated. The aqueous phase was extracted with dichloromethane (2×10 ml). The combined organic phases were dried with sodium sulfate, filtered, and concentrated by evaporation in vacuo. The solid brown residue was stirred for 10 minutes with methanol (10 ml), then suction filtered (58 mg) and washed with methanol (10 ml). The two solids were identical and were combined (198 mg, 45%).

The solid (123 mg, 0.33 mmole) was heated to the boil in ethanol (90 ml). Citric acid (152 mg, 0.79 mmole), dissolved in hot ethanol (5 ml), was added to the cloudy solution. The solution then became clear. The solution was boiled for a further 5 minutes, then cooled to room temperature, and concentrated to about half its volume by evaporation in vacuo. The solution was then stirred for 20 hours at room temperature, a colourless precipitate being formed. The precipitate was suction filtered and washed with ethanol (10 ml). Example 22 was obtained in a yield of 54% (100 mg) with a melting point of 278°-283° C.

$^1$H NMR (400 MHz, CD$_3$OD) δ ppm: 1.75-1.99 (m, 4H), 2.03-2.36 (m, 8H), 2.36-2.78 (m, 8H), 3.85-4.05 (m, 2H), 6.91-7.04 (m, 1H), 7.16-7.34 (m, 2H), 7.63-7.73 (m, 1H), 7.73-7.84 (m, 1H), 8.04-8.15 (m, 1H), 11.51 (s, 1H)

Example 23

4-(dimethylamino)-4-phenyl-spiro[cyclohexane-1,6'-(5,6,8,9-tetrahydropyrano[3,4-b]-5-azaindole)], Citrate (1:1), Non-Polar Diastereomer

Example 24

4-(dimethylamino)-4-phenyl-spiro[cyclohexane-1,6'-(5,6,8,9-tetrahydropyrano[3,4-b]-5-azaindole)], Citrate (1:1), Polar Diastereomer 4-(dimethylamino)-4-phenyl-spiro[cyclohexane-1,6'-(5,6,8,9-tetrahydropyrano[3,4-b]-5-azaindole)] (Non-Polar and Polar Diastereomer)

The ketone Ket-1 (267 mg, 1.23 mmole) and the 5-azatryptophol (Ind-2) (200 mg, 1.23 mmole) were dissolved in absolute 1,2-dichloroethane (40 ml), trifluoromethanesulfonic acid (0.12 ml, 204 mg, 1.36 mmole) was added, and the whole was stirred for 16 hours at room temperature. A pale oil settled out in the reaction flask. Further trifluoromethanesulfonic acid (0.12 ml, 204 mg, 1.36 mmole) was added and the mixture was heated under reflux for 5 hours. Water (30 ml) and 1N sodium hydroxide solution (10 ml) were added at room temperature to the reaction mixture and the whole was stirred for 30 minutes. The phases were separated. The aqueous phase was extracted with 1,2-dichloroethane (3×30 ml). The organic phases were combined, dried with sodium sulfate and concentrated by evaporation. The residue was a beige-coloured solid (455 mg), which was separated chromatographically [silica gel 60 (120 g); ethyl acetate/methanol 4:1 (500 ml), ethyl acetate/methanol 1:1 (500 ml), methanol (300 ml)]. 4-(dimethylamino)-4-phenyl-spiro[cyclohexane-1,6'-(5,6,8,9-tetrahydropyrano[3,4-b]-5-azaindole)] (non-polar diastereomer) was obtained as a colourless solid in a yield of 30% (133 mg). The polar diastereomer was impure (158 mg, 35%).

4-(dimethylamino)-4-phenyl-spiro[cyclohexane-1,6'-(5,6,8,9-tetrahydropyrano[3,4-b]-5-azaindole)], Citrate (1:1), Non-Polar diastereomer (Ex. 23)

4-(dimethylamino)-4-phenyl-spiro[cyclohexane-1,6'-(5,6,8,9-tetrahydropyrano[3,4-b]-5-azaindole)] (non-polar diastereomer) (120 mg, 0.332 mmole) was dissolved at 60° C. in ethanol (15 ml) and an ethanolic solution (2 ml) of citric acid (140 mg, 0.73 mmole) was added. After 22 hours diethyl ether (20 ml) was then added. After 30 minutes the colourless solid was separated by filtration and washed with ethanol/ethyl acetate 1:1 (3 ml) and diethyl ether (2 ml). Ex. 23 was obtained in a yield of 56% (102 mg) with a melting point of 273°-277° C.

$^1$H NMR (300 MHz, DMSO-$d_6$) δ ppm: 1.80-2.04 (m, 2H), 2.18-2.4 (m, 4H), 2.48 (s, 6H), 2.57 (dd, 4H), 2.79 (t, 2H), 3.91 (t, 2H), 7.15-7.3 (m, 6H), 8.24 (d, 1H), 8.94 (s, 1H) 12.17 (s, 1H)

4-(dimethylamino)-4-phenyl-spiro[cyclohexane-1,6'-(5,6,8,9-tetrahydropyrano[3,4-b]-5-azaindole)], Citrate (1:1), Polar Diastereomer (Ex. 24)

4-(dimethylamino)-4-phenyl-spiro[cyclohexane-1,6'-(5,6,8,9-tetrahydropyrano[3,4-b]-5-azaindole)] (polar diastereomer, impure (140 mg, 0.38 mmole) was dissolved in ethanol (7 ml) and citric acid (163 mg, 0.85 mmole), dissolved in ethanol (2 ml), was added. Precipitation occurred immediately. After 2 hours a colourless solid (103 mg) was separated by filtration and washed with ethanol (2×2 ml) and diethyl ether (2 ml). Diethyl ether (10 ml) was added to the filtrate, and the precipitate formed was separated and washed with diethyl ether (2×2 ml) (38 mg). The two solid fractions were combined and sodium hydroxide solution and trichloromethane were added (107 mg). The resultant solid was taken up in ethanol (30 ml) and citric acid (124 mg, 0.65 mmole), dissolved in ethanol (3 ml), was added. After 20 minutes a solid was separated and washed with ethanol (2×3 ml) and diethyl ether (2×2 ml) (59 mg). Diethyl ether (30 ml) was added to the filtrate and the whole was stirred for 16 hours at room temperature. A colourless solid was isolated by filtration and washed with diethyl ether (2×2 ml).

Yield (Ex. 24): 0.040 g (25%), melting point of 122°-127° C.

$^1$H NMR (300 MHz, DMSO-$d_6$) δ ppm: 1.63 (t, 2H), 1.92 (d, 2H), 2.13-2.27 (m, 2H), 2.36 (s, 6H), 2.57 (dd, 4H), 2.68-2.83 (m, 4H), 3.99 (t, 2H), 7.32 (d, 1H), 7.49-7.63 (m, 3H), 7.66-7.73 (m, 2H), 8.15 (d, 1H), 8.83 (s, 1H), 11.50 (s, 1H)

Example 25

4-butyl-4-(dimethylamino)-spiro[cyclohexane-1,8'-(5,6,8,9-tetrahydropyrano[3,4-b]-7-azaindole)]; Citrate (1:1), Non-Polar Diastereomer

Example 26

4-butyl-4-(dimethylamino)-spiro[cyclohexane-1,8'-(5,6,8,9-tetrahydropyrano[3,4-b]-7-azaindole)]; Citrate (1:1), Polar Diastereomer 4-butyl-4-(dimethylamino)-spiro[cyclohexane-1,8'-(5,6,8,9-tetrahydropyrano[3,4-b]-7-azaindole)] (Non-Polar and Polar Diastereomer)

The ketone Ket-9 (462 mg, 2.34 mmole) was dissolved together with the azatryptophol Ind-1 (380 mg, 2.34 mmole) in 1,2-dichloroethane (40 ml). Trifluoromethanesulfonic acid (773 mg, 0.457 ml, 5.15 mmole) was then added, following which the reaction mixture became coloured. The mixture was stirred for a total of 4 days at RT. The reaction mixture was worked up by adding water (10 ml), and then adjusted to pH 11 with 1N NaOH (10 ml) and stirred for 15 minutes. The phases were then separated. The aqueous phase was extracted with dichloromethane (2×10 ml). The combined organic extracts were dried with sodium sulfate, filtered and concentrated by evaporation in vacuo. Methanol (10 ml) was added to the brown oily residue, whereupon a colourless solid formed. This was suction filtered and washed with methanol (10 ml). The solid was 4-butyl-4-(dimethylamino)-spiro[cyclohexane-1,8'-(5,6,8,9-tetrahydropyrano[3,4-b]-7-azaindole)] (non-polar diastereomer) (39 mg, 5%, slightly impure). The mother liquor was concentrated by evaporation and separated chromatographically [silica gel 60 (50 g); ethyl acetate (1200 ml), ethyl acetate/methanol 4:1 (500 ml), 1:1 (500 ml)]. A yellow solid (239 mg) was obtained, which was vigorously stirred for 30 minutes with chloroform (25 ml), 1N NaOH (5 ml) and water (10 ml). The phases were then separated. The aqueous phase was extracted with chloroform (2×10 ml). The combined organic extracts were dried with sodium sulfate, filtered and concentrated by evaporation in vacuo. The yellow semi-solid residue (230 mg, 30%) was the polar diastereomer, which contained ca. 24% of the non-polar product. The separation was carried out via citrate formation.

4-butyl-4-(dimethylamino)-spiro[cyclohexane-1,8'-(5,6,8,9-tetrahydropyrano[3,4-b]-7-azaindole)]; Ditrate (1:1), Non-Polar Diastereomer (Ex. 25)

4-butyl-4-(dimethylamino)-spiro[cyclohexane-1,8'-(5,6,8,9-tetrahydropyrano[3,4-b]-7-azaindole)] (non-polar diastereomer) (27 mg, 0.08 mmole) was dissolved in ethanol (20 ml) by gentle heating, and citric acid (37 mg, 0.192 mmole), dissolved in hot ethanol (5 ml), was added. After stirring for 20 hours at RT the clear solution was almost completely concentrated, and diethyl ether (5 ml) was then added. A colourless solid began to precipitate out. This was suction filtered.

Yield (Ex. 25): 38 mg (88%).
Melting point: 86°-92° C.

4-butyl-4-(dimethylamino)-spiro[cyclohexane-1,8'-(5,6,8,9-tetrahydropyrano[3,4-b]-7-azaindole)]; Citrate (1:1), Polar Diastereomer (Ex. 26)

4-butyl-4-(dimethylamino)-spiro[cyclohexane-1,8'-(5,6,8,9-tetrahydropyrano[3,4-b]-7-azaindole)] (non-polar diastereomer) (contaminated with non-polar diastereomer, 230 mg, 0.67 mmole) was dissolved in ethanol (20 ml) by gentle heating, and citric acid (310 mg, 1.62 mmole), dissolved in hot ethanol (5 ml), was then added. After stirring for 1 hour at RT the clear solution had been reduced to about a third of its original volume, and diethyl ether (10 ml) was then added. A colourless solid began to precipitate out. This was suction filtered.

Yield (Ex. 26): 91 mg, (25%)
Melting point: 95°-103° C.

Example 27

4-benzyl-4-morpholino-spiro[cyclohexane-1,8'-(3-trifluoromethyl-5,6,8,9-tetrahydropyrano[3,4-b]-7-azaindole)]; Citrate (1:1), 1 Diastereomer Ket-13 (0.593 g, 2.17 mmole) was added together with Ind-3 (0.5 g, 2.17 mmole) to dichloromethane (11 ml, ultra-dry). The microwave vessel was closed with a septum and flushed with nitrogen. Trimethylsilyl trifluoromethanesulfonate (1.68 ml, 8.69 mmole) was then quickly added. The reaction mixture was heated for 10 minutes at 120° C. in the microwave vessel. 1M aqueous $Na_2CO_3$ solution was then added to the reaction mixture and the whole was stirred for 20 minutes. The organic phase was separated and the aqueous phase was extracted with dichloromethane (3×). The combined organic extracts were washed with water and saturated NaCl solution and dried over $MgSO_4$. After filtering the drying agent the solvent was removed on a rotary evaporator. The foamy solid obtained was purified by means of column chromatography (silica gel KG 60; dichloromethane:ethyl acetate 9:1). 4-benzyl-4-morpholino-spiro[cyclohexane-1,8'-(3-trifluoromethyl-5,6,8,9-tetrahydropyrano[3,4-b]-7-azaindole)] (0.12 g, 8.2%) was obtained as a cream-coloured solid.

The solid (0.120 g, 0.25 mmole) was dissolved in hot ethanol (15 ml) and citric acid (0.051 g) and diethyl ether (10 ml) were added. The solution was stirred overnight at room temperature. The solvent was removed on a rotary evaporator. The residue was crystallised with n-hexane/ethanol (10 ml; 9.5:0.5). The solid was suction filtered and dried at 60° C. in a high vacuum.

Yield (Ex. 27): 0.173 g (100%).

Example 28

4-(dimethylamino)-4-phenyl-spiro[cyclohexane-1,8'-(3-trifluoromethyl-5,6,8,9-tetrahydropyrano[3,4-b]-7-azaindole)]; Citrate (1:1), 1 Diastereomer Ket-1 (0.283 g, 1.30 mmole) was added together with Ind-3 (0.3 g, 1.30 mmole) to dichloromethane (3.4 ml, ultra-dry). The microwave vessel was closed with a septum and flushed with nitrogen. Trimethylsilyl trifluoromethanesulfonate (1.01 ml, 5.2 mmole) was then quickly added. The reaction mixture was heated for 10 minutes at 120° C. in the microwave vessel. 1M aqueous $Na_2CO_3$ solution was then added to the reaction mixture and the whole was stirred for 20 minutes. The organic phase was separated and the aqueous phase was extracted with dichloromethane (3×). The combined organic extracts were washed with water and saturated NaCl solution and dried over $MgSO_4$. After filtering the drying agent the solvent was removed on a rotary evaporator. The foamy solid obtained was purified by means of column chromatography (silica gel KG 60; dichloromethane:methanol 9:1) (0.116 g, 20.7%).

To precipitate the citrate the solid (0.100 g, 0.23 mmole) was dissolved in hot ethanol (2 ml) and citric acid (0.058 g) and diethyl ether (45 ml) were added. The reaction mixture was stirred for 1 hour at room temperature. The solid was suction filtered and dried at 60° C. in a high vacuum.

Yield (Ex. 28): 0.108 g (75%).

Example 29

4-(azetidin-1-yl)-4-phenyl-spiro[cyclohexane-1,8'-(5,6,8,9-tetrahydropyrano[3,4-b]-7-azaindole)], Citrate (1:1), 1 Diastereomer The ketone Ket-15 (275 mg, 1.2 mmole) was dissolved together with the azatryptophol Ind-1 (195 mg, 1.2 mmole) in dichloromethane (30 ml). Trifluoromethanesulfonic acid (397 mg, 0.235 ml, 2.64 mmole) was then added, whereupon the reaction mixture became dark. The mixture was stirred for 20 hours at RT. The reaction mixture was worked up by adding 1N NaOH (10 ml) and water (10 ml) and stirred for 10 minutes. The colour thereupon changed from dark red to pale brown. The phases of the filtrate were separated. The aqueous phase was extracted with dichloromethane (2×10 ml). The combined organic phases were dried with sodium sulfate, filtered and concentrated by evaporation in vacuo. A yellow solid was obtained, which was stirred for 10 minutes with dichloromethane (5 ml), then suction filtered and washed with dichloromethane (5 ml) (116 mg, 26%, diastereomer-pure, melting point: 269°-274° C.).

The solid (101 mg, 0.27 mmole) was heated to the boil in ethanol (60 ml). Citric acid (125 mg, 0.65 mmole), dissolved in hot ethanol (5 ml), was added to the cloudy solution. The solution became clear. After stirring for 20 hours at RT the solution was concentrated by evaporation to ca. 3 ml and diethyl ether (5 ml) was added until crystallisation occurred. The precipitated colourless precipitate was suction filtered and washed with diethyl ether (5 ml).

Yield (Ex. 29): 80 mg, (53%)
Melting point: 208°-212° C.

¹H NMR (300 MHz, DMSO-d₆) δ ppm: 1.50-1.81 (m, 2H), 1.81-2.04 (m, 4H), 2.04-2.25 (m, 2H), 2.30-2.50 (m, 2H), 2.56 (dd, J=26.01, 15.16 Hz, 4H), 2.64-2.77 (m, 2H), 3.47-3.77 (m, 4H), 3.97 (t, J=5.08 Hz, 2H), 6.89-7.07 (m, 1H), 7.46-7.89 (m, 6H), 8.00-8.16 (m, 1H), 11.44 (s, 1H)
¹³C NMR (101 MHz, DMSO-d₆) δ ppm: 15.3, 21.6, 24.2, 30.6, 44.0, 47.6, 59.0, 62.8, 71.1, 71.3, 104.2, 114.9, 118.6, 125.5, 128.5, 128.9, 132.3, 138.8, 141.8, 148.5, 171.1, 176.5

Example 30

4-butyl-4-(pyrrolidin-1-yl)-spiro[cyclohexane-1,8'-(5,6,8,9-tetrahydropyrano[3,4-b]-7-azaindole)]; Citrate (2:1), 1 Diastereomer The ketone Ket-16 (268 mg, 1.2 mmole) and the 7-azatryptophol (Ind-1, 195 mg, 1.2 mmole) were dissolved in absolute 1,2-dichloroethane (40 ml) and trifluoromethanesulfonic acid (0.117 ml, 198 mg, 1.32 mmole) was added and the whole was stirred for 3 days at room temperature. The reaction mixture was heated for 7 hours at 80° C. (bath temperature), following which trifluoromethanesulfonic acid (0.117 ml, 198 mg, 1.32 mmole) was added and the whole was stirred for 8 hours at 80° C. The mixture was stirred for a further 5 days at room temperature. Water (15 ml) and 1N sodium hydroxide solution (5 ml) were added to the reaction mixture and the whole was stirred for 15 minutes. The phases were separated. The aqueous phase was extracted with 1,2-dichloroethane (2×20 ml). The organic phases were combined, dried with sodium sulfate and concentrated by evaporation. The residue was a beige-coloured solid (424 mg), which was taken up in ethyl acetate/methanol 4:1 (3 ml). Following this a colourless solid began to precipitate out. Ethyl acetate (5 ml) was added and the solid was separated by filtration. 4-butyl-4-(pyrrolidin-1-yl)-spiro[cyclohexane-1,8'-(5,6,8,9-tetrahydropyrano[3,4-b]-7-azaindole)] (diastereomer-pure) was obtained in a yield of 12% (52 mg) with a melting point of 246°250° C.

The filtrate was concentrated by evaporation and separated chromatographically [silica gel 60 (50 g); ethyl acetate/methanol 4:1 (500 ml), methanol (200 ml)] and in this way further product was obtained (107 mg, 24%).

The solid (91 mg, 0.247 mmole) was dissolved at 30° C. in ethanol (7 ml) and an ethanolic solution of citric acid (105 mg, 0.545 mmole, 3 ml) was added. After 2 hours ethyl ether (50 ml) was added to the solution and the whole was stirred for 2 days at room temperature. During this time a pale brown precipitate formed, which was separated by filtration (50 mg). The filtrate was concentrated by evaporation, taken up in ethanol (1 ml), diethyl ether (20 ml) was added, and the whole was stirred for 30 minutes. A colourless solid was thereby formed, which was filtered and washed with diethyl ether (2×2 ml) (50 mg). Both solids were identical.

Yield (Ex. 30): 0.100 g (54%).
¹H NMR (300 MHz, DMSO-d₆) δ ppm: 1.02 (t 3H), 1.25-1.53 (m, 5H), 1.63-1.75 (m, 2H), 1.79-2.08 (m 15H), 2.58-2.74 (m 6H), 3.93 (t 2H), 6.99-7.07 (m 1H), 7.79-7.86 (m 1H), 8.13-8.18 (m 1H).

Example 31

4-(dimethylamino)-4-phenyl-spiro[cyclohexane-1,8'-(5,6,8,9-tetrahydro-thiopyrano[3,4-b]-7-azaindole)]; Citrate (1:1), 1 Diastereomer Ind-4 (258 mg, 1.2 mmole) was dissolved together with the ketone Ket-1 (261 mg, 1.2 mmole) in absolute 1,2-dichloroethane (24 ml) under argon and trifluoromethanesulfonic acid (0.44 ml, 4.96 mmole) was added. The reaction mixture was stirred for 1 hour at 150° C. in the microwave vessel. The reaction solution was worked up by adding saturated sodium carbonate solution (10 ml). The mixture was stirred for a further 15 minutes. After separating the phases the aqueous phase was extracted with dichloromethane (3×10 ml). The combined organic extracts were dried over Na₂SO₄ and then concentrated by evaporation. The crude product obtained (346 mg, yellow foam) was purified by column chromatography [silica gel 60 (20 g); cyclohexane/ethyl acetate 4:1 (500 ml), cyclohexane/ethyl acetate 1:1 (1000 ml)]. 4-(dimethylamino)-4-phenyl-spiro[cyclohexane-1,8'-(5,6,8,9-tetrahydro-thiopyrano[3,4-b]-7-azaindole)] was obtained as a beige-coloured solid (87 mg, 19%, melting point: 246°-253° C., diastereoisomer-pure). Further product precipitated out from the aqueous phase overnight. The solid was filtered and washed with water (3×0.5 ml) and with methanol (2×0.5 ml) (51 mg, 11% beige-coloured solid, melting point 262°-267° C.).

4-(dimethylamino)-4-phenyl-spiro[cyclohexane-1,8'-(5,6,8,9-tetrahydro-thiopyrano[3,4-b]-7-azaindole)] (135 mg, 0.358 mmole, diastereoisomer-pure) was dissolved in dichloromethane (6 ml) and citric acid (78 mg, 0.406 mmole), dissolved in ethyl acetate (12 ml), was added. During the addition of the acid a precipitate formed. Next the mixture was stirred for 17 hours at 23° C., and was then filtered and the precipitate was washed with ethyl acetate (3×0.5 ml).

Yield (Ex. 31): 188 mg (92%), white solid.
Melting point: 130°-136° C.
¹H NMR (400 MHz, CD₃OD) δ ppm: 2.01-2.15 (m, 4H), 2.52-2.71 (m, 7H), 2.71-2.90 (m, 5H), 2.90-3.05 (m, 6H), 7.02 (dd, J=7.79, 4.86 Hz, 1H), 7.59-7.72 (m, 3H), 7.74-7.81 (m, 2H), 7.81-7.88 (m, 1H), 8.08 (d, J=4.40 Hz, 1H)
¹³C NMR (101 MHz, CD₃OD) δ ppm: 24.4, 25.2, 28.4, 34.9, 38.4, 44.7, 45.4, 70.5, 74.2, 110.0, 116.4, 121.9, 127.9, 130.7, 130.8, 130.9, 131.5, 138.8, 143.1, 148.6, 174.7, 179.0

Example 32

4-(dimethylamino)-4-phenyl-spiro[cyclohexane-1,6'-(5,6,8,9-tetrahydro-thiopyrano[3,4-b]-5-azaindole)], Citrate (1:1), 1 Diastereomer Ind-5 (430 mg, 2.0 mmole) was dissolved together with the ketone Ket-1 (435 mg, 2.0 mmole) in absolute 1,2-dichloroethane (25 ml) under argon and trifluoromethanesulfonic acid (0.533 ml, 6.0 mmole) was added. The reaction mixture was stirred for 1 hour at 150° C. in the microwave vessel. The reaction solution was worked up by adding 1N sodium hydroxide solution (20 ml). The mixture was stirred for a further 15 minutes. After separating the phases the aqueous phase was extracted with dichloromethane (3×20 ml). The combined organic extracts were dried over Na₂SO₄ and then concentrated by evaporation. The crude product obtained (715 mg, brown solid) was purified by column chromatography [silica gel 60 (30 g); cyclohexane/ethyl acetate 4:1 (500 ml), cyclohexane/ethyl acetate 2:1 (600 ml), ethyl acetate/methanol 100:1 (1000 ml), ethyl acetate/methanol 5:1 (600 ml)]. 4-(dimethylamino)-4-phenyl-spiro[cyclohexane-1,6'-(5,6,8,9-tetrahydro-thiopyrano[3,4-b]-5-azaindole)] was obtained as an almost white solid (320 mg, 42%, melting point: 163°-168° C., diastereoisomer-pure).

The solid (233 mg, 0.617 mmole) was dissolved in hot isopropanol (10 ml) and citric acid (130 mg, 0.677 mmole), dissolved in hot isopropanol (10 ml), was added. During the addition of the acid a precipitate formed. The mixture was next stirred for 2 hours at 5° C., and then filtered and the precipitate was washed with isopropanol (2×0.5 ml) and acetone (3×0.5 ml).

Yield (Ex. 32): 350 mg (97%), white solid.

Melting point: 132°-140° C.

$^1$H NMR (400 MHz, DMSO-$d_6$) δ ppm: 1.04 (d, J=5.87 Hz, 1.5H), 1.82-2.03 (m, 4H), 2.16-2.39 (m, 7H), 2.49-2.70 (m, 5H), 2.75-2.91 (m, 2H), 2.91-3.14 (m, 4H), 3.68-3.86 (m, 0.25H), 7.24-7.44 (m, 1H), 7.44-7.84 (m, 5H), 8.07-8.27 (m, 1H), 8.74-8.94 (m, 1H), 11.47 (s, broad, 1H)

$^{13}$C NMR (101 MHz, DMSO-$d_6$) δ ppm: 23.3, 23.5, 25.4, 27.4, 33.4, 37.5, 44.0, 44.6, 62.0, 65.3, 71.5, 107.1, 109.8, 123.8, 126.6, 127.5, 128.6, 128.7, 131.9, 136.7, 138.1, 139.3, 140.4, 171.3, 176.5

Example 33

4-(1-methyl-1H-1,2,4-triazol-5-yl)-4-(methylamino)-spiro[cyclohexane-1,8'-(5,6,8,9-tetrahydropyrano[3,4-b]-7-azaindole)], Citrate (1:1), Polar Diastereomer Example 34

4-(1-methyl-1H-1,2,4-triazol-5-yl)-4-(methylamino)-spiro[cyclohexane-1,8'-(5,6,8,9-tetrahydropyrano[3,4-b]-7-azaindole)], Citrate (1:1), Non-Polar Diastereomer 4-(1-methyl-1H-1,2,4-triazol-5-yl)-4-(methylamino)-spiro[cyclohexane-1,8'-(5,6,8,9-tetrahydropyrano[3,4-b]-7-azaindole)] (Non-Polar and Polar Diastereomer)

The ketone Ket-17 (250 mg, 1.2 mmole) and the 7-azatryptophol (Ind-1, 195 mg, 1.2 mmole) were dissolved in absolute 1,2-dichloroethane (30 ml) and methanesulfonic acid (0.467 ml, 692 mg, 7.2 mmole) was added under argon. After 17 hours the reaction mixture was stirred for 7 hours at a bath temperature of 90° C. and for 15 hours at 75° C. 1N sodium hydroxide solution (15 ml) and water (10 ml) were added to the reaction mixture and the whole was stirred for 15 minutes. The phases were separated. The aqueous phase was extracted with 1,2-dichloroethane (2×20 ml). The organic phases were combined, dried with sodium sulfate and concentrated by evaporation. The residue was a beige-coloured solid, which was taken up in ethyl acetate (5 ml). At the same time a colourless solid began to precipitate out, which was separated by filtration and washed with ethyl acetate (2 ml).

4-(1-methyl-1H-1,2,4-triazol-5-yl)-4-(methylamino)-spiro[cyclohexane-1,8'-(5,6,8,9-tetrahydropyrano[3,4-b]-7-azaindole)] was obtained as a diastereoisomer mixture (130 mg). The filtrate was concentrated by evaporation and separated chromatographically [silica gel 60 (30 g); ethyl acetate/methanol 6:1 (700 ml)] (220 mg, colourless solid, diastereoisomer mixture).

The two fractions were re-chromatographed [silica gel 60 (20 g); chloroform/methanol 30:1 (500 ml)] and in this way 4-(1-methyl-1H-1,2,4-triazol-5-yl)-4-(methylamino)-spiro[cyclohexane-1,8'-(5,6,8,9-tetrahydropyrano[3,4-b]-7-azaindole)] (non-polar diastereoisomer) was obtained in a yield of 40% (164 mg) as a colourless solid with a melting point of 282°-287° C. The polar diastereoisomer was obtained in a yield of 11% (48 mg) with a melting point of 285°-289° C.

4-(1-methyl-1H-1,2,4-triazol-5-yl)-4-(methylamino)-spiro[cyclohexane-1,8'-(5,6,8,9-tetrahydropyrano[3,4-b]-7-azaindole)], Citrate (1:1), Polar Diastereomer (Ex. 33)

4-(1-methyl-1H-1,2,4-triazol-5-yl)-4-(methylamino)-spiro[cyclohexane-1,8'-(5,6,8,9-tetrahydropyrano[3,4-b]-7-azaindole)] (polar diastereomer) (48 mg, 0.136 mmole) was dissolved in ethanol (20 ml) by heating and citric acid (58 mg, 0.3 mmole), dissolved in ethanol (2 ml), was added. After stirring for 3 days at room temperature the clear solution had been almost completely concentrated and diethyl ether (5 ml) was added to the residue until crystallisation occurred.

Yield (Ex. 33): 71 mg (96%), colourless solid.

Melting point: 90°-93° C.

$^1$H NMR (300 MHz, DMSO-$d_6$) δ ppm: 1.72-1.92 (m, 2H), 1.92-2.02 (m, 2H), 2.04 (s, 3H), 2.07-2.19 (m, 4H), 2.56-2.83 (m, 10H), 3.91 (t, J=5.17 Hz, 2H), 4.10 (s, 3H), 6.94-7.09 (m, 1H), 7.78 (s, 1H), 7.79-7.86 (m, 1H), 8.10-8.22 (m, 1H), 11.35 (s, 1H)

$^{13}$C NMR (101 MHz, DMSO-$d_6$) δ ppm: 21.7, 27.0, 28.9, 29.0, 37.2, 42.8, 55.4, 59.1, 70.7, 72.3, 104.1, 115.0, 118.7, 125.7, 139.8, 141.8, 148.2, 148.9, 158.1, 171.2, 174.7

4-(1-methyl-1H-1,2,4-triazol-5-yl)-4-(methylamino)-spiro[cyclohexane-1,8'-(5,6,8,9-tetrahydropyrano[3,4-b]-7-azaindole)], Non-Polar Diastereomer (Ex. 34)

4-(1-methyl-1H-1,2,4-triazol-5-yl)-4-(methylamino)-spiro[cyclohexane-1,8'-(5,6,8,9-tetrahydropyrano[3,4-b]-7-azaindole)] (non-polar diastereomer) (149 mg, 0.423 mmole) was dissolved in ethanol (20 ml) and citric acid (179 mg, 0.93 mmole), dissolved in ethanol (2 ml), was added. After stirring for 3 days at room temperature the citrate 8K/9K was obtained as a colourless solid by suction filtration.

Yield (Ex. 34): 74 mg, (91%).

Melting point: 1920-193° C.

$^1$H NMR (300 MHz, DMSO-$d_6$) δ ppm: 1.80-2.10 (m, 6H), 2.11 (s, 3H), 2.52-2.77 (m, 8H), 3.95 (t, J=5.27 Hz, 2H), 4.08 (s, 3H), 6.93-7.04 (m, 1H), 7.73-7.83 (m, 1H), 7.99 (s, 1H), 8.06-8.16 (m, 1H), 11.41 (s, 1H)

$^{13}$C NMR (101 MHz, DMSO-$d_6$) δ ppm: 21.7, 27.7, 29.0, 31.2, 38.0, 38.9, 43.4, 57.0, 59.0, 71.2, 71.8, 104.1, 114.9, 118.6, 125.5, 139.2, 141.8, 148.5, 149.3, 152.4, 171.2, 175.7

Investigations on the Efficacy of the Compounds According to the Invention:

Measurements of the ORL1 Bonding

The cyclohexane derivatives of the general Formula I were investigated in a receptor binding assay with $^3$H-nociceptin/orphanin FQ using membranes of recombinant CHO-ORL1 cells. This test system was implemented according to the method proposed by Ardati et al. (Mol. Pharmacol., 51, 1997, pp. 816-824). The concentration of $^3$H-nociceptin/orphanin FQ in these tests was 0.5 nM. The binding assays were carried out with 20 μg of membrane protein per 200 μl of reaction batch in 50 mM Hepes, pH 7, 4, 10 mM $MgCl_2$ and 1 mM EDTA. The binding to the ORL1 receptor was determined using in each case 1 mg of WGA-SPA Beads (Amersham-Pharmacia, Freiburg), by incubating the reaction batch for 1 hour at RT followed by measurement in a Trilux scintillation counter (Wallac, Finland). The affinity is specified in Table 1 as nanomolar $K_i$ value in or % inhibition at c=1 μM.

Measurement of the μ Binding

The receptor affinity for the human μ-opiate receptor was determined in a homogeneous batch in microtitre plates. For this purpose dilution series of the substituted cyclohexyl-1,4-diamine derivative to be tested in each case were incubated with a receptor membrane preparation (15-40 μg protein per 250 μl incubation batch) of CHO-K1 cells which express the human μ-opiate receptor (RB-HOM receptor membrane preparation from the NEN company, Zaventem, Belgium), in the presence of 1 nmole/l of the radioactive ligand [³H]-naloxone (NET719, NEN company, Zaventem, Belgium) as well as 1 mg WGA-SPA beads (wheat germ agglutinin SPA beads from the company Amersham/Pharmacia, Freiburg, Germany), in a total volume of 250 μl for 90 minutes at room temperature. 50 mmole/l of tris-HCl supplemented with 0.05 wt. % of sodium azide and with 0.06 wt. % of bovine serum albumin was used as incubation buffer. To determine the non-specific binding, 25 μmol/l of naloxone was added in addition. After the end of the 90-minute incubation period the microtitre plates were centrifuged for 20 minutes at 1000 g and the radioactivity was measured in a B counter (Microbeta-Trilux, PerkinElmer Wallac, Freiburg, Germany). The percentage displacement of the radioactive ligand from its binding to the human μ-opiate receptor was determined at a concentration of the test substances of 1 μmole/l and given as percentage inhibition (% inhibition) of the specific binding. In some cases $IC_{50}$ inhibition concentrations that produce a 50% displacement of the radioactive ligand were calculated on the basis of the percentage displacement by different concentrations of the compounds of the general Formula I to be tested. Ki values for the test substances were obtained by conversion by means of the Cheng-Prusoff relationship.

Analgesia Testing in the Tail-Flick Test in Mice

The mice were in each case placed in individual test cages and the base of the tail was exposed to a focussed beam of heat from an electric lamp (Tail-flick type 50/08/1.bc, Labtec, Dr. Hess). The lamp intensity was adjusted so that the time from switching on the lamp to the sudden withdrawal of the tail (pain latency) was 3 to 5 seconds in untreated mice. Before the administration of the solutions containing the compound according to the invention or the respective comparison solutions, the mice were pretested twice within 5 minutes and the mean value of these measurements was calculated as a pre-test mean value.

The solutions of the compound according to the invention of the general Formula I as well as the comparison solutions were then administered intravenously. The pain measurement was carried out in each case 10, 20, 40 and 60 minutes after the intravenous administration. The analgesic effect was calculated as the increase in the pain latency (% of the maximum possible antinociceptive effect) according to the following formula:

$$[(T_1-T_0)/(T_2-T_0)]\times 100$$

Here the time $T_0$ is the latency time before the application, time $T_1$ is the latency time after the application of the active substance combination and time $T_2$ is the maximum exposure duration (12 seconds).

Analgesia Testing in the Tail-Flick Test in Rats

The analgesic efficacy of the test compounds was investigated in the focussed beam (tail-flick) test in rats according to the method of D'Amour and Smith (J. Pharm. Exp. Ther. 72, 74 79 (1941). For this purpose female Sprague Dawley rats weighing between 134 and 189 g were used. The animals were placed in special individual test cages and the base of the tail was exposed to a focussed beam of heat from a lamp (Tail-flick type 50/08/1.bc, Labtec, Dr. Hess). The lamp intensity was adjusted so that the time from switching on the lamp to the sudden withdrawal of the tail (pain latency) was 2.5-5 seconds in untreated animals. Before administering a test compound the animals were pretested twice within a period of 30 minutes and the mean value of these measurements was calculated as a pre-test mean value. The pain measurement was carried out 20, 40 and 60 minutes after intravenous administration. The analgesic effect was calculated as the increase in the pain latency (% MPE) according to the following formula:

$$[(T_1-T_0)/(T_2-T_0)]\times 100$$

Here $T_0$ is the latency time before and $T_1$ is the latency time after administration of the substance, and $T_2$ is the maximum exposure time (12 seconds).

In order to determine the dose dependence the respective compound was administered in 3-5 logarithmically increasing doses, including in each case the threshold dose and the maximum effect dose, and the $ED_{50}$ values were determined by means of regression analysis. The $ED_{50}$ calculation was carried out at the effect maximum, 20 minutes after intravenous administration of the substance.

The following table shows the example compounds in the form of the base without specifying which diastereomer is involved; in the cases in which the example compound was formed as a salt or was isolated as a polar and non-polar diastereomer, this can be inferred from the respective synthesis description.

The determined Ki values are given in the following table. Ki values were not determined for all compounds. As an example two compounds were investigated in the Tail-flick test.

| Example | Structure (possibly without counterion and indication of the diastereomer) | ORL1 Receptor, Ki value [μM] | μ-Opioid receptor, Ki value [μM] | Tail-flick |
|---|---|---|---|---|
| 1 | 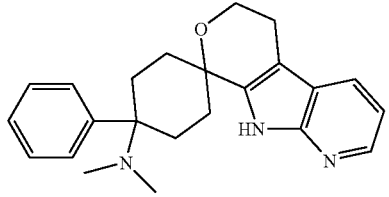 [SMILES: CN(C)C1(c2ccccc2)CCC2(CC1)OCCc1c2[nH]c2ncccc12] | 0.0147 | 0.0123 | |

-continued

| Example | Structure (possibly without counterion and indication of the diastereomer) | ORL1 Receptor, Ki value [μM] | μ-Opioid receptor, Ki value [μM] | Tail-flick |
|---|---|---|---|---|
| 2 | | 0.0053 | 0.0044 | Rat, i. v. $ED_{50}$: 15 μg/kg |
| 3 | | 0.0197 | 0.0147 | |
| 4 | | 0.0060 | 0.0118 | Mouse, i. v. 72% MPE at 464 μg/kg |
| 5 | | 0.1800 | 0.3033 | |
| 6 | | 0.0237 | 0.0250 | |
| 7 | | 2.3950 | 0.6367 | |

-continued

| Example | Structure (possibly without counterion and indication of the diastereomer) | ORL1 Receptor, Ki value [μM] | μ-Opioid receptor, Ki value [μM] | Tail-flick |
| --- | --- | --- | --- | --- |
| 8 | | 0.0657 | 0.0483 | |
| 9 | | 0.1533 | 0.0773 | |
| 10 | | | 0.0567 | |
| 12 | | 0.0683 | 0.0317 | |
| 13 | | 0.2800 | 0.0817 | |

-continued

| Example | Structure (possibly without counterion and indication of the diastereomer) | ORL1 Receptor, Ki value [µM] | µ-Opioid receptor, Ki value [µM] | Tail-flick |
|---|---|---|---|---|
| 14 | | | | |
| 15 | | | 0.0380 | |
| 17 | | 0.0870 | 0.0010 | |
| 18 | | 0.6633 | 0.0014 | |
| 19 | | | 2.9067 | |
| 20 | | | 0.0835 | |

-continued

| Example | Structure (possibly without counterion and indication of the diastereomer) | ORL1 Receptor, Ki value [μM] | μ-Opioid receptor, Ki value [μM] | Tail-flick |
|---|---|---|---|---|
| 21 | | 0.0280 | 0.0190 | |
| 22 | | 0.0167 | 0.0337 | |
| 23 | | 0.0023 | 0.0019 | |
| 24 | | | | |
| 25 | | | 0.0006 | |
| 26 | | | 0.0061 | |

-continued

| Example | Structure (possibly without counterion and indication of the diastereomer) | ORL1 Receptor, Ki value [μM] | μ-Opioid receptor, Ki value [μM] | Tail-flick |
|---------|---|---|---|---|
| 27 | | | | |
| 28 | | 2.6367 | 0.6375 | |
| 29 | | | | |
| 30 | | | | |
| 31 | | | | |
| 32 | | | | |

| Example | Structure (possibly without counterion and indication of the diastereomer) | ORL1 Receptor, Ki value [μM] | μ-Opioid receptor, Ki value [μM] | Tail-flick |
|---|---|---|---|---|
| 33 | 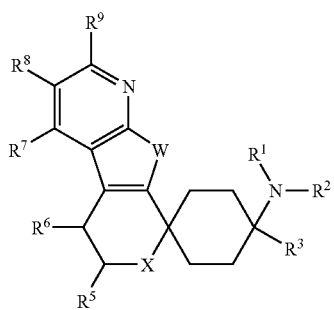 | | | |
| 34 | 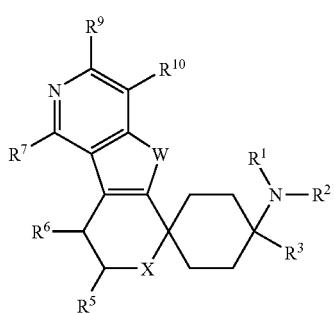 | | | |

Parenteral Solution of a Spirocyclic Azaindole Derivative According to the Invention 3 g of one of the spirocyclic azaindole derivatives according to the invention, in this case Example 1, is dissolved at room temperature in 1 l of water for injection purposes and then adjusted to isotonic conditions by adding anhydrous glucose for injection purposes.

The invention claimed is:

1. Spirocyclic azaindole derivatives of the Formulae Ia or Ib:

Ia

Ib wherein
W denotes $NR^4$;
X denotes O or S;
$R^1$ and $R^2$ independently of one another denote H; $C_{1-5}$-alkyl, saturated or unsaturated, branched or unbranched, unsubstituted or monosubstituted or polysubstituted; or the radicals $R^1$ and $R^2$ together form a ring and denote $CH_2CH_2OCH_2CH_2$, $CH_2CH_2NR^{11}CH_2CH_2$ or $(CH_2)_{3-6}$;
wherein $R^{11}$ denotes H; $C_{1-5}$-alkyl, saturated or unsaturated, branched or unbranched, unsubstituted or monosubstituted or polysubstituted;
$R^3$ denotes $C_{1-8}$-alkyl, in each case saturated or unsaturated, branched or unbranched, unsubstituted or monosubstituted or polysubstituted; $C_{3-8}$-cycloalkyl, in each case unsubstituted or monosubstituted or polysubstituted; aryl or heteroaryl, in each case unsubstituted or monosubstituted or polysubstituted; aryl, heteroaryl or $C_{3-8}$-cycloalkyl bonded via a $C_{1-3}$-alkyl group, in each case unsubstituted or monosubstituted or polysubstituted;
$R^4$ denotes H; $C_{1-5}$-alkyl, saturated or unsaturated, branched or unbranched, unsubstituted or monosubstituted or polysubstituted;
$R^5$ denotes H, $C_{1-5}$-alkyl, branched or unbranched, unsubstituted or monosubstituted or polysubstituted, or denotes $COOR^{13}$;
wherein $R^{13}$ denotes H; $C_{1-5}$-alkyl, in each case saturated or unsaturated, branched or unbranched, unsubstituted or monosubstituted or polysubstituted; $C_{3-8}$-cycloalkyl, in each case saturated or unsaturated, unsubstituted or monosubstituted or polysubstituted; aryl or heteroaryl, unsubstituted or monosubstituted or polysubstituted; or aryl, $C_{3-8}$-cycloalkyl or heteroaryl bonded via $C_{1-3}$-alkyl, unsubstituted or monosubstituted or polysubstituted;
$R^6$ denotes H; $C_{1-5}$-alkyl; aryl, unsubstituted or monosubstituted or polysubstituted; or aryl coupled via a $C_{1-3}$-alkyl group, which coupled aryl is unsubstituted or monosubstituted or polysubstituted; and $R^7$, $R^8$, $R^9$ and $R^{10}$ independently of one another denote H; methyl, ethyl, propyl, butyl; pyridyl, O-benzyl, F, Cl, Br, I, $CF_3$, OH, $OCH_3$, $NH_2$, COOH, $COOCH_3$, $NHCH_3$ or $N(CH_3)_2$ or $NO_2$;

wherein monosubstituted or polysubstituted in connection with "alkyl" or "cycloalkyl" means the substitution of one or more hydrogen atoms, respectively, independently by F, Cl, Br, I, —CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, S-benzyl, $OCF_3$, O—$C_{1-6}$-alkyl, OH, O—$C_{1-6}$-alkyl-OH, =O, $C_{1-6}$alkyl, benzyl, O-benzyl, O-phenyl, C(=O)$C_{1-6}$-alkyl, $CO_2H$, or $CO_2$—$C_{1-6}$-alkyl; and wherein monosubstituted or polysubstituted in connection with "aryl" and "heteroaryl" means the substitution of one or more hydrogen atoms of the ring system, respectively, independently by F, Cl, Br, I, CN, $NH_2$, NH—$C_{1-6}$-alkyl, NH—$C_{1-6}$-alkyl-OH, $N(C_{1-6}$alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$alkyl-OH, C(=O)$C_{1-6}$alkyl,

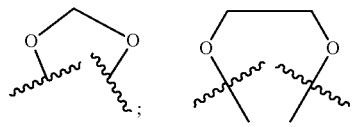 [SMILES: *OCO* ; *OCCO*]

$CO_2H$, $CO_2$—$C_{1-6}$-alkyl, $CF_3$, $OCF_3$, $C_{1-6}$-alkyl, on one or possibly different atoms (wherein a substituent itself can possibly be substituted);

said spirocyclic azaindole derivatives optionally being in the form of the racemate; in the form of the enantiomers, diastereomers, mixtures of the enantiomers or diastereomers, or of an individual enantiomer or diastereomer; or in the form of the bases and/or salts of physiologically compatible acids.

2. Spirocyclic azaindole derivatives according to claim 1, wherein monosubstituted or polysubstituted in connection with "alkyl" or "cycloalkyl" means the substitution of one or more hydrogen atoms, respectively, independently by F, Cl, Br, I, CN, $NH_2$, NH—$C_{1-6}$-alkyl, NH—$C_{1-6}$-alkyl-OH, $N(C_{1-6}$alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, $CO_2H$, $CO_2$—$C_{1-6}$-alkyl, $CF_3$, $OCF_3$, $C_{1-6}$-alkyl, and monosubstituted or polysubstituted in connection with "aryl" and "heteroaryl" means the substitution of one or more hydrogen atoms of the ring system, respectively, independently by F, Cl, Br, I, CN, $NH_2$, NH—$C_{1-6}$-alkyl, NH—$C_{1-6}$-alkyl-OH, $N(C_{1-6}$alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, $CO_2H$, $CO_2$—$C_{1-6}$-alkyl, $CF_3$, $OCF_3$, $C_{1-6}$-alkyl,

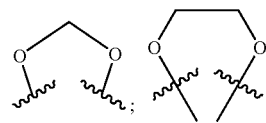

or phenoxy.

3. Spirocyclic azaindole derivatives according to claim 1, wherein $R^1$ and $R^2$ denote $CH_3$.

4. Spirocyclic azaindole derivatives according to claim 1, wherein $R^3$ denotes propyl, butyl, pentyl, hexyl, phenyl, furyl, thiophenyl, naphthyl, benzyl, benzofuranyl, indolyl, indanyl, benzodioxanyl, benzodioxolanyl, pyridyl, pyrimidyl, pyrazinyl, triazolyl or benzothiophenyl, in each case unsubstituted or monosubstituted or polysubstituted; phenyl, furyl or thiophenyl bonded via a saturated, unbranched $C_{1-3}$-alkyl group, in each case unsubstituted or monosubstituted or polysubstituted.

5. Spirocyclic azaindole derivatives according to claim 4, wherein $R^3$ denotes butyl, ethyl, 3-methoxypropyl, benzothiophenyl, phenyl, 3-methylphenyl, 3-fluorophenyl, benzo[1,3]-dioxolyl, benzyl, 1-methyl-1,2,4-triazolyl, thienyl or phenethyl.

6. Spirocyclic azaindole derivatives according to claim 1, wherein $R^5$ denotes H.

7. Spirocyclic azaindole derivatives according to claim 1, wherein $R^6$ denotes H.

8. Spirocyclic azaindole derivatives according to claim 1, wherein $R^7$, $R^8$, $R^9$ and $R^{10}$ denote H.

9. Spirocyclic azaindole derivatives according to claim 1, which are selected from the group consisting of:
(1) 4-(dimethylamino)-4-phenyl-spiro[cyclohexane-1,8'-(5,6,8,9-tetrahydropyrano[3,4-b]-7-azaindole)];
(2) 4-(dimethylamino)-4-phenyl-spiro[cyclohexane-1,8'-(5,6,8,9-tetrahydropyrano[3,4-b]-7-azaindole)]; methansulfonate;
(3) 4-(dimethylamino)-4-phenyl-spiro[cyclohexane-1,6'-(5,6,8,9-tetrahydropyrano[3,4-b]-5-azaindole)];
(4) 4-(dimethylamino)-4-thiophen-2-yl-spiro[cyclohexane-1,8'-(5,6,8,9-tetrahydropyrano[3,4-b]-7-azaindole)]; methanesulfonate;
(5) 4-(dimethylamino)-4-thiophen-2-yl-spiro[cyclohexane-1,6'-(5,6,8,9-tetrahydropyrano[3,4-b]-5-azaindole)];
(6) 4-(dimethylamino)-4-phenyl-spiro[cyclohexane-1,8'-(5,6,8,9-tetrahydropyrano[3,4-b]-7-azaindole)]; citrate (4:3);
(7) 4-(methylamino)-4-phenyl-spiro[cyclohexane-1,8'-(5,6,8,9-tetrahydropyrano[3,4-b]-7-azaindole)]; citrate (1:1);
(8) 4-(methylamino)-4-thiophen-2-yl-spiro[cyclohexane-1,8'-(5,6,8,9-tetrahydropyrano[3,4-b]-7-azaindole)]; citrate (4:3);
(9) 4-(dimethylamino)-4-benzo[1,3-dioxol]-spiro[cyclohexane-1,8'-(5,6,8,9-tetrahydropyrano[3,4-b]-7-azaindole)]; citrate (1:1);
(10) 4-(dimethylamino)-4-(benzothiophen-2-yl)-spiro[cyclohexane-1,8'-(5,6,8,9-tetrahydropyrano[3,4-b]-7-azaindole)]; citrate (1:1);
(12) 4-(dimethylamino)-4-(3-fluorophenyl)-spiro[cyclohexane-1,8'-(5,6,8,9-tetrahydropyrano[3,4-b]-7-azaindole)]; citrate (4:3);
(13) 4-(dimethylamino)-4-(3-methylphenyl)-spiro[cyclohexane-1,8'-(5,6,8,9-tetrahydropyrano[3,4-b]-7-azaindole)]; citrate (1:1);
(14) 4-(dimethylamino)-4-(but-1-yl)-spiro[cyclohexane-1,8'-(5,6,8,9-tetrahydropyrano[3,4-b]-7-azaindole)], citrate (1:1);
(15) 4-(dimethylamino)-4-phenylethyl-spiro[cyclohexane-1,8'-(3-trifluoromethyl-5,6,8,9-tetrahydropyrano[3,4-b]-7-azaindole)]; citrate (1:1);
(17) 4-(dimethylamino)-4-ethyl-spiro[cyclohexane-1,8'-(5,6,8,9-tetrahydropyrano[3,4-b]-7-azaindole)]; citrate (2:3);

(18) 4-(dimethylamino)-4-phenylethyl-spiro[cyclohexane-1,8'-(5,6,8,9-tetrahydropyrano[3,4-b]-7-azaindole)]; citrate (2:3);
(19) 4-benzyl-4-morpholino-spiro[cyclohexane-1,8'-(5,6,8,9-tetrahydropyrano[3,4-b]-7-azaindole)]; citrate (1:1);
(20) 4-(dimethylamino)-4-(3-methoxypropyl)-spiro[cyclohexane-1,8'-(5,6,8,9-tetrahydropyrano[3,4-b]-7-azaindole)]; citrate (1:1);
(21) 4-(dimethylamino)-4-phenyl-spiro[cyclohexane-1,8'-(5,6,8,9-tetrahydropyrano[3,4-b]-7-azaindole)]; citrate (1:1);
(22) 4-(dimethylamino)-4-thiophen-2-yl-spiro[cyclohexane-1,8'-(5,6,8,9-tetrahydropyrano[3,4-b]-7-azaindole)]; citrate (1:1);
(23) 4-(dimethylamino)-4-phenyl-spiro[cyclohexane-1,6'-(5,6,8,9-tetrahydropyrano[3,4-b]-5-azaindole)], citrate (1:1);
(24) 4-(dimethylamino)-4-phenyl-spiro[cyclohexane-1,6'-(5,6,8,9-tetrahydropyrano[3,4-b]-5-azaindole)], citrate (1:1);
(25) 4-butyl-4-(dimethylamino)-spiro[cyclohexane-1,8'-(5,6,8,9-tetrahydropyrano[3,4-b]-7-azaindole)]; citrate (1:1);
(26) 4-butyl-4-(dimethylamino)-spiro[cyclohexane-1,8'-(5,6,8,9-tetrahydropyrano[3,4-b]-7-azaindole)]; citrate (1:1);
(27) 4-benzyl-4-morpholino-spiro[cyclohexane-1,8'-(3-trifluoromethyl-5,6,8,9-tetrahydropyrano[3,4-b]-7-azaindole)]; citrate (1:1);
(28) 4-(dimethylamino)-4-phenyl-spiro[cyclohexane-1,8'-(3-trifluoromethyl-5,6,8,9-tetrahydropyrano[3,4-b]-7-azaindole)]; citrate (1:1);
(29) 4-(azetidin-1-yl)-4-phenyl-spiro[cyclohexane-1,8'-(5,6,8,9-tetrahydropyrano[3,4-b]-7-azaindole)], Citrate (1:1);
(30) 4-butyl-4-(pyrrolidin-1-yl)-spiro[cyclohexane-1,8'-(5,6,8,9-tetrahydropyrano[3,4-b]-7-azaindole)]; citrate (2:1);
(31) 4-(dimethylamino)-4-phenyl-spiro[cyclohexane-1,8'-(5,6,8,9-tetrahydro-thiopyrano[3,4-b]-7-azaindole)]; citrate (1:1);
(32) 4-(dimethylamino)-4-phenyl-spiro[cyclohexane-1,6'-(5,6,8,9-tetrahydro-thiopyrano[3,4-b]-5-azaindole)], citrate (1:1);
(33) 4-(1-methyl-1H-1,2,4-triazol-5-yl)-4-(methylamino)-spiro[cyclohexane-1,8'-(5,6,8,9-tetrahydropyrano[3,4-b]-7-azaindole)], citrate (1:1); and
(34) 4-(1-methyl-1H-1,2,4-triazol-5-yl)-4-(methylamino)-spiro[cyclohexane-1,8'-(5,6,8,9-tetrahydropyrano[3,4-b]-7-azaindole)], citrate (1:1);

in the form of the racemate; in the form of the enantiomers, diastereomers, mixtures of the enantiomers or diastereomers, or of an individual enantiomer or diastereomer; in the form of the bases and/or salts of physiologically compatible acids.

10. A pharmaceutical composition comprising at least one substituted azaindole derivative according to claim 1, optionally in the form of its racemate, in the form of the pure stereoisomers, in the form of a mixture of multiple stereoisomers in an arbitrary mixture ratio; in the form of its acids or its bases or in the form of its salts, and also optionally containing suitable additives and/or auxiliary substances and/or optionally further active substances.

11. A method of treating pain in a patient in need of such treatment, said method comprising administering to said patient an effective amount therefor of a substituted azaindole derivative according to claim 1, optionally in the form of its racemate, in the form of the pure stereoisomers, in the form of a mixture of multiple stereoisomers in an arbitrary mixture ratio; in the form of its acids or its bases or in the form of its salts.

* * * * *